(12) United States Patent
Ruelle et al.

(10) Patent No.: US 7,521,549 B2
(45) Date of Patent: Apr. 21, 2009

(54) COMPOUNDS

(75) Inventors: Jean-Louis Ruelle, Rixensart (BE); Vincent George Christian Louis Verlant, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 602 days.

(21) Appl. No.: 10/755,115

(22) Filed: Jan. 9, 2004

(65) Prior Publication Data

US 2004/0147474 A1    Jul. 29, 2004

Related U.S. Application Data

(62) Division of application No. 09/857,716, filed as application No. PCT/IB99/02014 on Dec. 7, 1999, now Pat. No. 6,706,270.

(30) Foreign Application Priority Data

| Dec. 8, 1998 | (GB) | ................................. 9826979.8 |
| Dec. 8, 1998 | (GB) | ................................. 9826980.6 |
| Dec. 17, 1998 | (GB) | ................................. 9828015.9 |
| Jan. 5, 1999 | (GB) | ................................. 9900090.3 |

(51) Int. Cl.
| C07H 21/04 | (2006.01) |
| C12P 21/04 | (2006.01) |
| C07K 14/22 | (2006.01) |
| A61K 39/095 | (2006.01) |
| A61K 39/02 | (2006.01) |
| C12N 1/20 | (2006.01) |

(52) U.S. Cl. .................. 536/23.7; 536/24.1; 536/24.32; 435/69.3; 435/69.7; 530/300; 530/350; 424/184.1; 424/190.1; 424/249.1; 424/250.1

(58) Field of Classification Search .............. 424/250.1, 424/184.1, 185.1, 190.1, 249, 249.1; 435/69.7, 435/69.3, 300, 350; 536/23.7, 24.1, 24.32; 530/300, 350
See application file for complete search history.

(56) References Cited

U.S. PATENT DOCUMENTS 6,835,384 B1    12/2004  Aujame et al.

FOREIGN PATENT DOCUMENTS

| EP | 1475441 A2 | 11/2004 |
| WO | WO 92/01460 | 2/1992 |
| WO | WO 94/08013 | 4/1994 |
| WO | WO 99/57280 | 11/1999 |
| WO | WO 0022430 A3 | 4/2000 |
| WO | WO 0026375 | 5/2000 |

OTHER PUBLICATIONS

Snyder et al, Molecular Genetics of Bacteria, American Society for Microbiology 1997.*
Martin, et al. 1997; J.Ex.Med. vol. 185, No. 7 (Apr. 7, 1997) pp. 1173-1184.
Frazer, et al. 1999 AAY 74695.
PCT International Search Report for PCT/IB99/02014 dated Jul. 7, 2000.
Lissolo et al., 1995, Infection and Immunity, 63:884-890.
Biotechnologia Aplicada, 1996, 13:1-7.
PCT International Preliminary Examination Report for PCT/IB99/02014 dated Mar. 14, 2001.

* cited by examiner

Primary Examiner—Shanon A. Foley
Assistant Examiner—Padma v Baskar
(74) Attorney, Agent, or Firm—RatnerPrestia

(57) ABSTRACT

The invention provides BASB041, 43, 44 and 48 polypeptides and polynucleotides encoding BASB041, 43, 44 and 48 polypeptides and methods for producing such polypeptides by recombinant techniques. Also provided are diagnostic, prophylactic and therapeutic uses.

12 Claims, 27 Drawing Sheets

Figure 1A

Identity to SeqID No:1 is indicated by a dot, and a dash ("-") indicates a missing nucleotide.

```
                        *         20         *
Seqid1  :  ATGAAAACCGTTTCCACCGCCGTTGTCCTT  :  30
Seqid3  :  ..............................  :  30
Seqid5  :  ..............................  :  30

40              *         60
Seqid1  :  GCCGCCGCTGCCGTTTCACTGACCGGCTGT  :  60
Seqid3  :  ..............................  :  60
Seqid5  :  ..............................  :  60

*         80         *
Seqid1  :  GCGACCGAATCCTCACGCAGTCTCGAGGTA  :  90
Seqid3  :  ..............................  :  90
Seqid5  :  ..............................  :  90

100              *        120
Seqid1  :  GAGAAAGTCGCCTCCTACAATACGCAATAC  :  120
Seqid3  :  ..............................  :  120
Seqid5  :  .............................T  :  120

*        140         *
Seqid1  :  CACGGCGTGCGTACCCCGATTTCCGTCGGA  :  150
Seqid3  :  ..............................  :  150
Seqid5  :  .....T..T.....................  :  150

160              *        180
Seqid1  :  ACATTCGACAACCGCTCCAGCTTCCAAAAA  :  180
Seqid3  :  ..............................  :  180
```

Figure 1B

Identity to SeqID No:1 is indicated by a dot, and a dash ("-") indicates a missing nucleotide.

```
Seqid5   : .............................. : 180

*         200         *
Seqid1   : GGCATTTTCTCCGACGGGGAAGACCGTTTG : 210
Seqid3   : .............................. : 210
Seqid5   : .............................. : 210

220         *         240
Seqid1   : GGCAGCCAGGCAAAAACCATTCTGGTAACG : 240
Seqid3   : .............................. : 240
Seqid5   : ........................A..... : 240

*         260         *
Seqid1   : CACCTGCAACAGACCAACCGCTTCAACGTA : 270
Seqid3   : .............................. : 270
Seqid5   : .............................. : 270

280         *         300
Seqid1   : CTGAACCGCACCAATTTGAACGCATTAAAA : 300
Seqid3   : .............................. : 300
Seqid5   : .............................. : 300

*         320         *
Seqid1   : CAGGAATCCGGCATTTCCGGCAAAGCGCAT : 330
Seqid3   : .............................. : 330
Seqid5   : .............................. : 330

340         *         360
Seqid1   : AACCTGAAAGGCGCAGATTATGTCGTTACT : 360
Seqid3   : .............................. : 360
Seqid5   : ........................... C  : 360
```

Figure 1C

Identity to SeqID No:1 is indicated by a dot, and a dash ("-") indicates a missing nucleotide.

```
                          *        380            *
Seqid1 : GGCGATGTAACCGAATTCGGACGCAGAGAT : 390
Seqid3 : .............................. : 390
Seqid5 : .............................. : 390

400           *        420
Seqid1 : GTCGGCGATCATCAGCTCTTCGGCATTTTG : 420
Seqid3 : .............................. : 420
Seqid5 : .............................. : 420

*        440            *
Seqid1 : GGTCGCGGCAAATCGCAAATCGCCTATGCA : 450
Seqid3 : .............................. : 450
Seqid5 : .............................. : 450

460           *        480
Seqid1 : AAAGTGGCTCTGAATATCGTCAACGTCAAT : 480
Seqid3 : .............................. : 480
Seqid5 : .............................. : 480

*        500            *
Seqid1 : ACTTCCGAAATCGTCTATTCCGCACAGGGC : 510
Seqid3 : .............................. : 510
Seqid5 : .............................. : 510

520           *        540
Seqid1 : GCGGGCGAATACGCACTTTCCAACCGTGAA : 540
Seqid3 : .............................. : 540
Seqid5 : .............................. : 540

*        560            *
Seqid1 : ATCATCGGTTTCGGCGGCACTTCCGGCTAC : 570
Seqid3 : .............................. : 570
```

Figure 1D

Identity to SeqID No:1 is indicated by a dot, and a dash ("-") indicates a missing nucleotide.

```
Seqid5  : ............................ : 570

580           *           600
Seqid1  : GATGCGACTTTGAACGGCAAAGTTTTAGAC : 600
Seqid3  : ............................. : 600
Seqid5  : ............................. : 600

*          620             *
Seqid1  : TTGGCAATCCGCGAA-CCGTCAACAGCCTG : 629
Seqid3  : ...............G............. : 630
Seqid5  : ...............G............. : 630

640           *           660
Seqid1  : GTTCAGGCTGTTGACAACGGCGCATGGCAA : 659
Seqid3  : ............................. : 660
Seqid5  : ............................. : 660

*
Seqid1  : CCCAACCGTTAA : 671
Seqid3  : ............ : 672
Seqid5  : ............ : 672
```

Figure 2A

Identity to SeqID No:2 is indicated by a dot, and a dash ("-") indicates a missing amino acid.

```
                    *           20           *
Seqid2 : MKTVSTAVVLAAAAVSLTGCATESSRSLEV : 30
Seqid4 : .............................. : 30
Seqid6 : .............................. : 30

40           *           60
Seqid2 : EKVASYNTQYHGVRTPISVGTFDNRSSFQK : 60
Seqid4 : .............................. : 60
Seqid6 : .............................. : 60

*           80           *
Seqid2 : GIFSDGEDRLGSQAKTILVTHLQQTNRFNV : 90
Seqid4 : .............................. : 90
Seqid6 : .............................. : 90

100           *          120
Seqid2 : LNRTNLNALKQESGISGKAHNLKGADYVVT : 120
Seqid4 : .............................. : 120
```

Figure 2B

Identity to SeqID No:2 is indicated by a dot, and a dash ("-") indicates a missing amino acid.

```
Seqid6  : ........................... : 120

*         140           *
Seqid2  : GDVTEFGRRDVGDHQLFGILGRGKSQIAYA : 150
Seqid4  : ............................. : 150
Seqid6  : ............................. : 150

160         *          180
Seqid2  : KVALNIVNVNTSEIVYSAQGAGEYALSNRE : 180
Seqid4  : ............................. : 180
Seqid6  : ............................. : 180

*         200           *
Seqid2  : IIGFGGTSGYDATLNGKVLDLAIREPSTAW : 210
Seqid4  : ........................AVNSL : 210
Seqid6  : ........................AVNSL : 210

220
Seqid2  : FRLLTTAHGNPTV : 223
Seqid4  : VQAVDNGAWQ.NR : 223
Seqid6  : VQAVDNGAWQ.NR : 223
```

Figure 13A

Identity to SeqID No:17 is indicated by a dot.

```
                      *         20          *
Seqid17  :  ATGACCCCTTCCGCACTGAAAAAAACCGTC  :   30

40          *         60
Seqid17  :  CTGCTGCTCGGCACTGCCTTTGCCGCCGCA  :   60

*         80          *
Seqid17  :  TCCGCACAAGCCTCCGGCTACCACTTCGGC  :   90
Seqid19  :  ..............................  :   18

100          *        120
Seqid17  :  ACACAGTCGGTCAACGCGCAAAGCACGGCA  :  120
Seqid19  :  ..............................  :   48

*        140          *
Seqid17  :  AATGCCGCCGCCGCAGAAGCCGCCGACGCA  :  150
Seqid19  :  ..............................  :   78

160          *        180
Seqid17  :  TCGACCATCTTCTACAACCCTGCCGGCCTG  :  180
Seqid19  :  ..............................  :  108

*        200          *
Seqid17  :  ACCAAACTCGACAGCAGCCAGATTTCCGTC  :  210
Seqid19  :  ..............................  :  138
```

Figure 13B

Identity to SeqID No:17 is indicated by a dot.

```
                   220            *            240
Seqid17 : AACGCCAACATCGTGCTGCCCAGCATTCAT  :  240
Seqid19 : ............................. :  168

*            260            *
Seqid17 : TATGAGGCGGATTCCGCCACCGACTTTACC  :  270
Seqid19 : ............................. :  198

280            *            300
Seqid17 : GGGCTTCCCGTCCAAGGTTCGAAAAGCGGC  :  300
Seqid19 : ............................. :  228

*            320            *
Seqid17 : AAAATCACCAAAACCACGGTCGCGCCCCAC  :  330
Seqid19 : ............................. :  258

340            *            360
Seqid17 : ATCTACGGCGCATACAAAGTCAACGACAAT  :  360
Seqid19 : ............................. :  288

*            380            *
Seqid17 : CTGACCGTAGGCTTGGGCGTGTACGTCCCC  :  390
Seqid19 : ........G.................... :  318

400            *            420
Seqid17 : TTCGGTTCTGCCACCGAATACGAAAAGAT   :  420
Seqid19 : .....C.......................  :  348

*            440            *
Seqid17 : TCCGTGTTGCGCCACAACATCAACAAACTC  :  450
Seqid19 : ............................. :  378
```

Figure 13C

Identity to SeqID No:17 is indicated by a dot.

```
                       460            *           480
Seqid17 : GGTCTGACCAGCATCGCCGTCGAACCTGTC : 480
Seqid19 : .............................. : 408

*            500            *
Seqid17 : GCCGCGTGGAAACTCAACGACCGCCATTCC : 510
Seqid19 : .............................. : 438

520            *           540
Seqid17 : TTCGGCGCAGGCATCATCGCCCAACATACT : 540
Seqid19 : .............................. : 468

*            560            *
Seqid17 : TCCGCCGAACTGCGCAAATATGCCGACTGG : 570
Seqid19 : .............................. : 498

580            *           600
Seqid17 : GGGATTAAGAGTAAAGCAGAGATATTGACG : 600
Seqid19 : .............................. : 528

*            620            *
Seqid17 : GCAAAACCGCCCAAACCTAACGGTGTAGCC : 630
Seqid19 : .............................. : 558

640            *           660
Seqid17 : GAAGCTGCAAAAATTCAGGCCGACGGACAC : 660
Seqid19 : .............................. : 588

*            680            *
Seqid17 : GCCGATGTCAAAGGCAGCGATTGGGGCTTC : 690
Seqid19 : .............................. : 618
```

Figure 13D

Identity to SeqID No:17 is indicated by a dot.

```
                    700          *         720
Seqid17 : GGCTACCAACTGGCGTGGATGTGGGACATC : 720
Seqid19 : .............................. : 648

*          740          *
Seqid17 : AACGACCGTGCGCGCGTGGGCGTGAACTAC : 750
Seqid19 : .............................. : 678

760          *         780
Seqid17 : CGTTCCAAAGTCTCGCACACGCTCAAAGGC : 780
Seqid19 : .............................. : 708

*          800          *
Seqid17 : GATGCCGAATGGGCGGCAGACGGCGCGGCG : 810
Seqid19 : .............................. : 738

820          *         840
Seqid17 : GCGAAAGCAATGTGGAGTACGATGCTTGCA : 840
Seqid19 : .............................. : 768

*          860          *
Seqid17 : GCAAACGGCTACACGGCGAATGAAAAGCC  : 870
Seqid19 : .............................. : 798

880          *         900
Seqid17 : CGCGTTAAAATCGTTACGCCTGAGTCTTTG : 900
Seqid19 : .............................. : 828

*          920          *
Seqid17 : TCCGTACACGGTATGTACAAAGTGTCCGAT : 930
```

Figure 13E

Identity to SeqID No:17 is indicated by a dot.

```
Seqid19  : .............................. :  858

940           *          960
Seqid17  : AAAGCCGACCTGTTCGGCGACGTAACTTGG : 960
Seqid19  : .............................. :  888

*          980          *
Seqid17  : ACGCGCCACAGCCGCTTCGATAAGGCGGAA : 990
Seqid19  : .............................. :  918

1000          *         1020
Seqid17  : CTGGTTTTTGAAAAGAAAAAACCGTCGTC : 1020
Seqid19  : .............................. :  948

*         1040          *
Seqid17  : AAAGGCAAATCCGACCGCACCACCATCACC : 1050
Seqid19  : .............................. :  978

1060          *         1080
Seqid17  : CCCAACTGGCGCAACACCTACAAAGTCGGC : 1080
Seqid19  : .............................. : 1008

*         1100          *
Seqid17  : TTCGGCGGTTCTTATCAAATCAGCGAACCG : 1110
Seqid19  : .............................. : 1038

1120          *         1140
Seqid17  : CTGCAACTGCGCGCCGGCATCGCTTTTGAC : 1140
Seqid19  : .............................. : 1068
```

Figure 13F

Identity to SeqID No:17 is indicated by a dot.

```
                *        1160           *
Seqid17 : AAATCGCCCGTCCGCAACGCCGACTACCGC : 1170
Seqid19 : ............................. : 1098

1180           *        1200
Seqid17 : ATGAACAGCCTGCCCGACGGCAACCGCATC : 1200
Seqid19 : ...........A.................. : 1128

*        1220           *
Seqid17 : TGGTTCTCCGCCGGTATGAAATACCATATC : 1230
Seqid19 : ............................. : 1158

1240           *        1260
Seqid17 : GGTAAAAACCACGTCGTCGATGCCGCCTAC : 1260
Seqid19 : ............................. : 1188

*        1280           *
Seqid17 : ACCCACATCCACATCAACGACACCACCTAC : 1290
Seqid19 : .......................G.... : 1218

1300           *        1320
Seqid17 : CGCACGGCGAAGGCAAGCGGCAACGATGTG : 1320
Seqid19 : ............................. : 1248

*        1340           *
Seqid17 : GACAGCAAAGGCGCGTCTTCCGCACGTTTC : 1350
Seqid19 : ............................. : 1278

1360           *        1380
Seqid17 : AAAAACCACGCCGACATCATCGGCCTGCAA : 1380
Seqid19 : ........................T..... : 1308
```

Figure 13G

Identity to SeqID No:17 is indicated by a dot.

```
                           *         1400
Seqid17 :   TACACCTACAAATTCAAATAA  : 1401
Seqid19 :   .....................  : 1329
```

Figure 14A

Identity to SeqID No:18 is indicated by a dot.

```
                    *         20           *
Seqid18 : MTPSALKKTVLLLGTAFAAASAQASGYHFG  :  30
Seqid20 :                       ......    :   6

40          *         60
Seqid18 : TQSVNAQSTANAAAAEAADASTIFYNPAGL  :  60
Seqid20 : ..............................  :  36

*         80           *
Seqid18 : TKLDSSQISVNANIVLPSIHYEADSATDFT  :  90
Seqid20 : ..............................  :  66

100         *        120
Seqid18 : GLPVQGSKSGKITKTTVAPHIYGAYKVNDN  : 120
Seqid20 : ..............................  :  96
```

Figure 14B

Identity to SeqID No:18 is indicated by a dot.

```
                  *         140           *
Seqid18 : LTVGLGVYVPFGSATEYEKDSVLRHNINKL : 150
Seqid20 : .............................. : 126

160           *          180
Seqid18 : GLTSIAVEPVAAWKLNDRHSFGAGIIAQHT : 180
Seqid20 : .............................. : 156

*         200           *
Seqid18 : SAELRKYADWGIKSKAEILTAKPPKPNGVA : 210
Seqid20 : .............................. : 186

220           *          240
Seqid18 : EAAKIQADGHADVKGSDWGFGYQLAWMWDI : 240
Seqid20 : .............................. : 216

*         260           *
Seqid18 : NDRARVGVNYRSKVSHTLKGDAEWAADGAA : 270
Seqid20 : .............................. : 246

280           *          300
Seqid18 : AKAMWSTMLAANGYTANEKARVKIVTPESL : 300
```

Figure 14C

Identity to SeqID No:18 is indicated by a dot.

```
Seqid20 :  ..............................  :  276

*         320           *
Seqid18 :  SVHGMYKVSDKADLFGDVTWTRHSRFDKAE  :  330
Seqid20 :  ..............................  :  306

340          *          360
Seqid18 :  LVFEKEKTVVKGKSDRTTITPNWRNTYKVG  :  360
Seqid20 :  ..............................  :  336

*         380           *
Seqid18 :  FGGSYQISEPLQLRAGIAFDKSPVRNADYR  :  390
Seqid20 :  ..............................  :  366

400          *          420
Seqid18 :  MNSLPDGNRIWFSAGMKYHIGKNHVVDAAY  :  420
Seqid20 :  ..............................  :  396

*         440           *
Seqid18 :  THIHINDTTYRTAKASGNDVDSKGASSARF  :  450
Seqid20 :  ........S.....................  :  426
```

Figure 14D

Identity to SeqID No:18 is indicated by a dot.

```
                    460
Seqid18 : KNHADIIGLQYTYKFK : 466
Seqid20 : ................ : 442
```

COMPOUNDS

CROSS REFERENCE TO RELATED APPLICATIONS

This application is a divisional application of U.S. patent application Ser. No. 09/857,716 filed Sep. 6, 2001, now U.S. Pat. No. 6,706,270, which is the National Stage Application of International Application No. PCT/IB99/02014, filed Dec. 7, 1999 which was published under PCT article 21(2) in English, which claims the benefit of Great Britain Patent Application Serial No. 9826979.8, filed Dec. 8, 1998; Great Britain Patent Application Serial No. 9826980.6, filed Dec. 8, 1998; Great Britain Patent Application Serial No. 9828015.9, filed Dec. 17, 1998; and Great Britain Patent Application Serial No. 9900090.3, filed Jan. 5, 1999. The disclosure of these applications are herein incorporated by reference in their entirety.

FIELD OF THE INVENTION

This invention relates to polynucleotides, (herein referred to as "BASB041 polynucleotide(s)", "BASB043 polynucleotide(s)", "BASB044 polynucleotides" and "BASB048 polynucleotide(s)"), polypeptides encoded by them (referred to herein as "BASB041", "BASB043", "BASB044" and "BASB048" respectively or "BASB041 polypeptide(s)", "BASB043 polynucleotide(s)", "BASB044 polynucleotides" and "BASB048 polynucleotide(s)" respectively), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens.

BACKGROUND OF THE INVENTION

*Neisseria meningitidis* (meningococcus) is a Gram-negative bacterium frequently isolated from the human upper respiratory tract. It occasionally causes invasive bacterial diseases such as bacteremia and meningitis. The incidence of meningococcal disease shows geographical seasonal and annual differences (Schwartz, B., Moore, P. S., Broome, C. V.; Clin. Microbiol. Rev. 2 (Supplement), S18-S24, 1989). Most disease in temperate countries is due to strains of serogroup B and varies in incidence from $1{-}10/100,000$/year total population sometimes reaching higher values (Kaczmarski, E. B. (1997), Commun. Dis. Rep. Rev. 7: R55-9, 1995; Scholten, R. J. P. M., Bijlmer, H. A., Poolman, J. T. et al. Clin. Infect. Dis. 16: 237-246, 1993; Cruz, C., Pavez, G., Aguilar, E., et al. Epidemiol. Infect. 105: 119-126, 1990).

Epidemics dominated by serogroup A meningococci, mostly in central Africa, are encountered, sometimes reaching levels up to $1000/100,000$/year (Schwartz, B., Moore, P. S., Broome, C. V. Clin. Microbiol. Rev. 2 (Supplement), S18-S24, 1989). Nearly all cases as a whole of meningococcal disease are caused by serogroup A, B, C, W-135 and Y meningococci and a tetravalent A, C, W-135, Y polysaccharide vaccine is available (Armand, J., Arminjon, F., Mynard, M. C., Lafaix, C., J. Biol. Stand. 10: 335-339, 1982).

The polysaccharide vaccines are currently being improved by way of chemical conjugating them to carrier proteins (Lieberman, J. M., Chiu, S. S., Wong, V. K., et al. JAMA 275: 1499-1503, 1996).

A serogroup B vaccine is not available, since the B capsular polysaccharide was found to be nonimmunogenic, most likely because it shares structural similarity to host components (Wyle, F. A., Artenstein, M. S., Brandt, M. L. et al. J. Infect. Dis. 126: 514-522, 1972; Finne, J. M., leinonen, M., Makela, P. M. Lancet ii.: 355-357, 1983).

For many years efforts have been initiated and carried out to develop meningococcal outer membrane based vaccines (de Moraes, J. C., Perkins, B., Camargo, M. C. et al. Lancet 340: 1074-1078, 1992; Bjune, G., Hoiby, E. A. Gronnesby, J. K. et al. 338: 1093-1096, 1991). Such vaccines have demonstrated efficacies from 57%-85% in older children (>4 years) and adolescents.

Many bacterial outer membrane components are present in these vaccines, such as PorA, PorB, Rmp, Opc, Opa, FrpB and the contribution of these components to the observed protection still needs further definition. Other bacterial outer membrane components have been defined by using animal or human antibodies to be potentially relevant to the induction of protective immunity, such as TbpB and NspA (Martin, D., Cadieux, N., Hamel, J., Brodeux, B. R., J. Exp. Med. 185: 1173-1183, 1997; Lissolo, L., Maitre-Wilmotte, C., Dumas, p. et al., Inf. Immun. 63: 884-890, 1995). The mechanisms of protective immunity will involve antibody mediated bactericidal activity and opsonophagocytosis.

A bacteremia animal model has been used to combine all antibody mediated mechanisms (Saukkonen, K., Leinonen, M., Abdillahi, H. Poolman, J. T. Vaccine 7: 325-328, 1989). It is generally accepted that the late complement component mediated bactericidal mechanism is crucial for immunity against meningococcal disease (Ross, S. C., Rosenthal P. J., Berberic, H. M., Densen, P. J. Infect. Dis. 155: 1266-1275, 1987).

The frequency of *Neisseria meningitidis* infections has risen dramatically in the past few decades. This has been attributed to the emergence of multiply antibiotic resistant strains and an increasing population of people with weakened immune systems. It is no longer uncommon to isolate *Neisseria meningitidis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB041, BASB043, BASB044, and BASB048, in particular BASB041, BASB043, BASB044, and BASB048 polypeptides and BASB041, BASB043, BASB044, and BASB048 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB041, BASB043, BASB044, and BASB048 polynucleotides or polypeptides.

Various changes and modifications within the spirit and scope of the disclosed invention will become readily apparent to those skilled in the art from reading the following descriptions and from reading the other parts of the present disclosure.

BRIEF DESCRIPTION OF THE DRAWINGS

FIGS. 1A-1D are consecutive alignments for three BASB041-encoding polynucleotide sequences.

FIGS. 2A-2B are consecutive alignments for three BASB041 polypeptide sequences.

FIGS. 13A-13G are consecutive alignments for two BASB044-encoding polynucleotide sequences.

FIGS. 14A-14D are consecutive alignments for two BASB044 polypeptide sequences.

DESCRIPTION OF THE INVENTION

Figure 3:
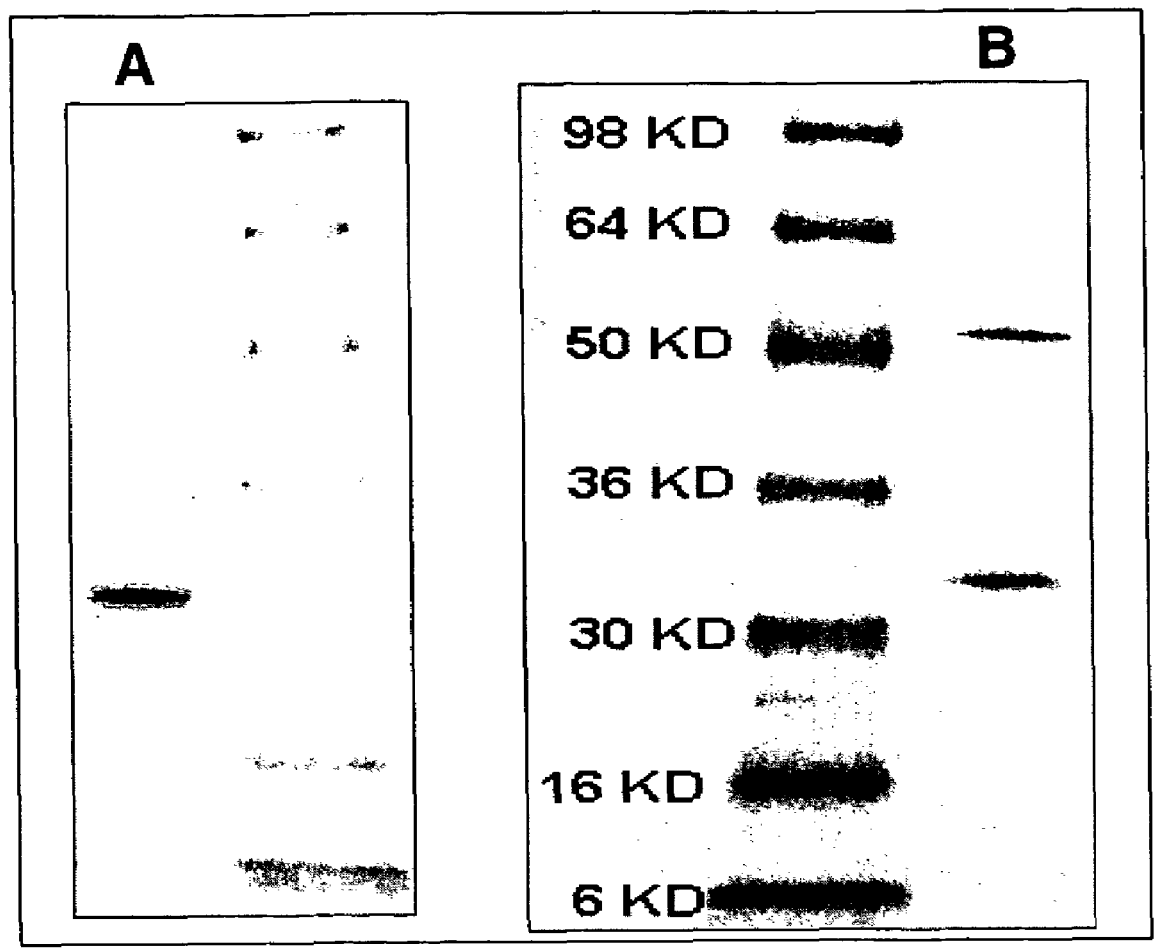
FIG. 3 is an electrophoretic analysis of purified BASB041 polypeptide (A. Coomassie stained SDS-polyacrylamide gel of BASB041./B. Immunodetection of the same gel using an anti-tetra-His immune response.

The invention relates to BASB041, BASB043, BASB044, and BASB048 polypeptides and polynucleotides as described in greater detail below. The invention relates especially to BASB041, BASB043, BASB044, and BASB048 having the nucleotide and amino acid sequences set out in SEQ ID NO:1, 3,5,11,17,19,25 and SEQ ID NO:2,4,6,12,18,20,26 respectively. It is understood that sequences recited in the Sequence Listing below as "DNA" represent an exemplification of one embodiment of the invention, since those of ordinary skill will recognize that such sequences can be usefully employed in polynucleotides in general, including ribopolynucleotides.

Polypeptides

In one aspect of the invention there are provided polypeptides of *Neisseria meningitidis* referred to herein as "BASB041", "BASB043", "BASB044" and "BASB048" and "BASB041 polypeptides", "BASB043 polypeptides", "BASB044 polypeptides" and "BASB048 polypeptides" as well as biologically, diagnostically, prophylactically, clinically or therapeutically useful variants thereof, and compositions comprising the same.

The present invention further provides for:
(a) an isolated polypeptide which comprises an amino acid sequence which has at least 85% identity, more preferably at least 90% identity, yet more preferably at least 95% identity, most preferably at least 97-99% or exact identity, to that of SEQ ID NO:2, 4, 6.
(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:1, 3, 5 over the entire length of SEQ ID NO:1, 3, 5 respectively.
(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:2, 4, 6;

The BASB041 polypeptides provided in SEQ ID NO:2,4,6 are the BASB041 polypeptides from *Neisseria meningitidis* strains ATCC13090 and H44/76.

The invention also provides an immunogenic fragment of a BASB041 polypeptide, that is, a contiguous portion of the BASB041 polypeptide which has the same or substantially the same immunogenic activity as the polypeptide comprising the amino acid sequence of SEQ ID NO:2,4,6. That is to say, the fragment (if necessary when coupled to a carrier) is capable of raising an immune response which recognises the BASB041 polypeptide. Such an immunogenic fragment may include, for example, the BASB041 polypeptide lacking an N-terminal leader sequence, and/or a transmembrane domain and/or a C-terminal anchor domain. In a preferred aspect the immunogenic fragment of BASB041 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:2,4,6 over the entire length of SEQ ID NO:2,4,6.

The present invention further provides for:
(a) an isolated polypeptide which comprises an amino acid sequence which has at least 85% identity, more preferably at least 90% identity, yet more preferably at least 95% identity, most preferably at least 97-99% or exact identity, to that of SEQ ID NO:12.
(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:11 over the entire length of SEQ ID NO:11.
(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:12.

The BASB043 polypeptides provided in SEQ ID NO:12 are the BASB043 polypeptides from *Neisseria meningitidis* strains ATCC13090 and H44/76.

The invention also provides an immunogenic fragment of a BASB043 polypeptide, that is, a contiguous portion of the BASB043 polypeptide which has the same or substantially the same immunogenic activity as the polypeptide comprising the amino acid sequence of SEQ ID NO:12. That is to say, the fragment (if necessary when coupled to a carrier) is capable of raising an immune response which recognises the BASB043 polypeptide. Such an immunogenic fragment may include, for example, the BASB043 polypeptide lacking an N-terminal leader sequence, and/or a transmembrane domain and/or a C-terminal anchor domain. In a preferred aspect the immunogenic fragment of BASB043 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:12 over the entire length of SEQ ID NO:12.

The present invention further provides for:
(a) an isolated polypeptide which comprises an amino acid sequence which has at least 85% identity, more preferably at least 90% identity, yet more preferably at least 95% identity, most preferably at least 97-99% or exact identity, to that of SEQ ID NO:18, 20.
(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:17, 19 over the entire length of SEQ ID NO:17, 19 respectively.
(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:18, 20.

The BASB044 polypeptides provided in SEQ ID NO:18, 20 are the BASB044 polypeptides from *Neisseria meningitidis* strains ATCC13090 and H44/76.

The invention also provides an immunogenic fragment of a BASB044 polypeptide, that is, a contiguous portion of the BASB044 polypeptide which has the same or substantially the same immunogenic activity as the polypeptide comprising the amino acid sequence of SEQ ID NO:18,20. That is to say, the fragment (if necessary when coupled to a carrier) is capable of raising an immune response which recognises the BASB044 polypeptide. Such an immunogenic fragment may include, for example, the BASB044 polypeptide lacking an N-terminal leader sequence, and/or a transmembrane domain and/or a C-terminal anchor domain. In a preferred aspect the immunogenic fragment of BASB044 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:18,20 over the entire length of SEQ ID NO:18, 20.

The present invention further provides for:
(a) an isolated polypeptide which comprises an amino acid sequence which has at least 85% identity, more preferably at least 90% identity, yet more preferably at least 95% identity, most preferably at least 97-99% or exact identity, to that of SEQ ID NO:26.
(b) a polypeptide encoded by an isolated polynucleotide comprising a polynucleotide sequence which has at least 85% identity, more preferably at least 90% identity, yet more preferably at least 95% identity, even more preferably at least 97-99% or exact identity to SEQ ID NO:25 over the entire length of SEQ ID NO:25.
(c) a polypeptide encoded by an isolated polynucleotide comprising a polynucleotide sequence encoding a polypeptide which has at least 85% identity, more preferably at least 90% identity, yet more preferably at least 95% identity, even more preferably at least 97-99% or exact identity, to the amino acid sequence of SEQ ID NO:26

The BASB048 polypeptide provided in SEQ ID NO:26 is the BASB048 polypeptide from *Neisseria meningitidis* strain ATCC13090.

The invention also provides an immunogenic fragment of a BASB048 polypeptide, that is, a contiguous portion of the BASB048 polypeptide which has the same or substantially the same immunogenic activity as the polypeptide comprising the amino acid sequence of SEQ ID NO:26. That is to say, the fragment (if necessary when coupled to a carrier) is capable of raising an immune response which recognises the BASB048 polypeptide. Such an immunogenic fragment may include, for example, the BASB048 polypeptide lacking an N-terminal leader sequence, and/or a transmembrane domain and/or a C-terminal anchor domain. In a preferred aspect the immunogenic fragment of BASB048 according to the invention comprises substantially all of the extracellular domain of a polypeptide which has at least 85% identity, more preferably at least 90% identity, yet more preferably at least 95% identity, most preferably at least 97-99% identity, to that of SEQ ID NO:26 over the entire length of SEQ ID NO:26.

A fragment is a polypeptide having an amino acid sequence that is entirely the same as part but not all of any amino acid sequence of any polypeptide of the invention. As with BASB041, BASB043, BASB044 and BASB048 polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of SEQ ID NO:2,4,6,12,18,20,26 or of variants thereof, such as a continuous series of residues that includes an amino- and/or carboxyl-terminal amino acid sequence. Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2,4,6,12,18,20,26 or an isolated polypeptide comprising an amino acid sequence having at least 15, 20, 30, 40, 50 or 100 contiguous amino acids truncated or deleted from the amino acid sequence of SEQ ID NO:2,4,6,12,18,20,26.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5-10, 1-5, 1-3, 1-2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LytA. Preferably the C terminal portion of the molecule is used. LytA is derived from *Streptococcus pneumoniae* which synthesize an N-acetyl-L-alanine amidase, amidase LytA, (coded by the lytA gene {Gene, 43 (1986) page 265-272}) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795-798}. It is possible to use the repeat portion of the LytA molecule found in the C terminal end starting at residue 178, for example residues 188-305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Neisseria meningitidis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB041 polypeptides, particularly polynucleotides that encode the polypeptide herein designated BASB041.

In a particularly preferred embodiment of the invention the polynucleotide comprises a region encoding BASB041 polypeptides comprising a sequence set out in SEQ ID NO:1, 3,5 which includes a full length gene, or a variant thereof.

The BASB041 polynucleotides provided in SEQ ID NO:1,3 and 5 are the BASB041 polynucleotides from *Neisseria meningitidis* strains ATCC13090 and H44/76.

As a further aspect of the invention there are provided isolated nucleic acid molecules encoding and/or expressing BASB041 polypeptides and polynucleotides, particularly *Neisseria meningitidis* BASB041 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB041 polypeptide having a deduced amino acid sequence of SEQ ID NO:2,4,6 and polynucleotides closely related thereto and variants thereof.

In another particularly preferred embodiment of the invention there is a BASB041 polypeptide from *Neisseria meningitidis* comprising or consisting of an amino acid sequence of SEQ ID NO:2,4,6 or a variant thereof.

Using the information provided herein, such as a polynucleotide sequence set out in SEQ ID NO:1,3,5 a polynucleotide of the invention encoding BASB041 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:1,3,5, typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1,3,5 was discovered in a DNA library derived from *Neisseria meningitidis*.

Moreover, each DNA sequence set out in SEQ ID NO:1,3,5 contains an open reading frame encoding a protein having about the number of amino acid residues set forth in SEQ ID NO:2,4,6 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 669 of SEQ ID NO:1, encodes the polypeptide of SEQ ID NO:2.

The polynucleotide of SEQ ID NO:3, between the start codon at nucleotide number 1 and the stop codon which begins at nucleotide number 670 of SEQ ID NO:3, encodes the polypeptide of SEQ ID NO:4.

The polynucleotide of SEQ ID NO:5, between the first codon at nucleotide number 1 and the stop codon which begins at nucleotide number 670 of SEQ ID NO:5, encodes the polypeptide of SEQ ID NO:6.

In a further aspect, the present invention provides for an isolated polynucleotide comprising or consisting of:
(a) a polynucleotide sequence which has at least 85% identity, more preferably at least 90% identity, yet more preferably at least 95% identity, even more preferably at least 97-99% or exact identity to SEQ ID NO:1,3,5 over the entire length of SEQ ID NO:1,3,5 respectively; or
(b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:2, 4, 6 over the entire length of SEQ ID NO:2, 4, 6 respectively.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO: 1, 3, 5 or a fragment thereof; and isolating a full-length gene and/or genomic clones containing said polynucleotide sequence.

The invention provides a polynucleotide sequence identical over its entire length to a coding sequence (open reading frame) in SEQ ID NO: 1, 3, 5. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB041 polypeptide of SEQ ID NO:2, 4, 6 may be identical to the polypeptide encoding sequence contained in nucleotides 1 to 668 of SEQ ID NO:1, or the polypeptide encoding sequence contained in nucleotides 1 to 669 of SEQ ID NO:3, or the polypeptide encoding sequence contained in nucleotides 1 to 669 of SEQ ID NO:5, respectively. Alternatively it may be a sequence, which as a result of the redundancy (degeneracy) of the genetic code, also encodes the polypeptide of SEQ ID NO:2, 4, 6.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB041 having an amino acid sequence set out in SEQ ID NO:2, 4, 6. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2, 4, 6. Fragments of polynucleotides of the invention may be used, for example, to synthesize full-length polynucleotides of the invention.

Further particularly preferred embodiments are polynucleotides encoding BASB041 variants, that have the amino acid sequence of BASB041 polypeptide of SEQ ID NO:2, 4, 6 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB041 polypeptide.

Further preferred embodiments of the invention are polynucleotides that are at least 85% identical over their entire length to a polynucleotide encoding BASB041 polypeptide having an amino acid sequence set out in SEQ ID NO:2, 4, 6, and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1, 3, 5.

In accordance with certain preferred embodiments of this invention there are provided polynucleotides that hybridize, particularly under stringent conditions, to BASB041 polynucleotide sequences, such as those polynucleotides in SEQ ID NO:1, 3, 5.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1,3,5 under stringent hybridization conditions with a probe having the sequence of said polynucleotide sequence set forth in SEQ ID NO:1,3,5 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB041 and to isolate cDNA and genomic clones of other genes that have a high identity, particularly high sequence identity, to the BASB041 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB041 gene may be isolated by screening using a DNA sequence provided in SEQ ID NO:1, 3,5 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB043 polypeptides, particularly polynucleotides that encode the polypeptide herein designated BASB043.

In a particularly preferred embodiment of the invention the polynucleotide comprises a region encoding BASB043 polypeptides comprising a sequence set out in SEQ ID NO:11 which includes a full length gene, or a variant thereof.

The BASB043 polynucleotide provided in SEQ ID NO:11 is the BASB043 polynucleotide from *Neisseria meningitidis* strains ATCC 13090.

As a further aspect of the invention there are provided isolated nucleic acid molecules encoding and/or expressing BASB043 polypeptides and polynucleotides, particularly *Neisseria meningitidis* BASB043 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB043 polypeptide having a deduced amino acid sequence of SEQ ID NO:12 and polynucleotides closely related thereto and variants thereof.

In another particularly preferred embodiment of the invention there is a BASB043 polypeptide from *Neisseria meningitidis* comprising or consisting of an amino acid sequence of SEQ ID NO:12 or a variant thereof.

Using the information provided herein, such as a polynucleotide sequence set out in SEQ ID NO:11 a polynucleotide of the invention encoding BASB043 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:11 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence illustrative of the invention, each polynucleotide set out in SEQ ID NO:11 was discovered in a DNA library derived from *Neisseria meningitidis*.

Moreover, each DNA sequence set out in SEQ ID NO:11 contains an open reading frame encoding a protein having about the number of amino acid residues set forth in SEQ ID NO:12 with a deduced molecular weight that can be calculated using amino acid residue molecular weight values well known to those skilled in the art.

The polynucleotide of SEQ ID NO:11, between the start codon at nucleotide number 1 and the stop codon which begins at nucleotide number 487 of SEQ ID NO:11, encodes the polypeptide of SEQ ID NO:12.

In a further aspect, the present invention provides for an isolated polynucleotide comprising or consisting of:
(a) a polynucleotide sequence which has at least 85% identity, more preferably at least 90% identity, yet more preferably at least 95% identity, even more preferably at least 97-99% or exact identity to SEQ ID NO:11 over the entire length of SEQ ID NO:11; or
(b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:12 over the entire length of SEQ ID NO:12.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO: 11 or a fragment thereof; and isolaing a full-length gene and/or genomic clones containing said polynucleotide sequence.

The invention provides a polynucleotide sequence identical over its entire length to a coding sequence (open reading frame) in SEQ ID NO: 11. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB043 polypeptide of SEQ ID NO:12 may be identical to the polypeptide encoding sequence contained in nucleotides 1 to 486 of SEQ ID NO:11. Alternatively it may be a sequence, which as a result of the redundancy (degeneracy) of the genetic code, also encodes the polypeptide of SEQ ID NO:12.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB043 having an amino acid sequence set out in SEQ ID NO:12. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:12. Fragments of polynucleotides of the invention may be used, for example, to synthesize full-length polynucleotides of the invention.

Further particularly preferred embodiments are polynucleotides encoding BASB043 variants, that have the amino acid sequence of BASB043 polypeptide of SEQ ID NO:12 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB043 polypeptide.

Further preferred embodiments of the invention are polynucleotides that are at least 85% identical over their entire length to a polynucleotide encoding BASB043 polypeptide having an amino acid sequence set out in SEQ ID NO:12 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:11.

In accordance with certain preferred embodiments of this invention there are provided polynucleotides that hybridize, particularly under stringent conditions, to BASB043 polynucleotide sequences, such as those polynucleotides in SEQ ID NO:11.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:11 under stringent hybridization conditions with a probe having the sequence of said polynucleotide sequence set forth in SEQ ID NO:11 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB043 and to isolate cDNA and genomic clones of other genes that have a high identity, particularly high sequence identity, to the BASB043 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB043 gene may be isolated by screening using a DNA sequence provided in SEQ ID NO:11 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB044 polypeptides, particularly polynucleotides that encode the polypeptide herein designated BASB044.

In a particularly preferred embodiment of the invention the polynucleotide comprises a region encoding BASB044 polypeptides comprising a sequence set out in SEQ ID NO:17,19 which includes a full length gene, or a variant thereof.

The BASB044 polynucleotides provided in SEQ ID NO:17,19 are the BASB044 polynucleotides from *Neisseria meningitidis* strains ATCC13090 and H44/76.

As a further aspect of the invention there are provided isolated nucleic acid molecules encoding and/or expressing BASB044 polypeptides and polynucleotides, particularly *Neisseria meningitidis* BASB044 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB044 polypeptide having a deduced amino acid sequence of SEQ ID NO:18,20 and polynucleotides closely related thereto and variants thereof.

In another particularly preferred embodiment of the invention there is a BASB044 polypeptide from *Neisseria meningitidis* comprising or consisting of an amino acid sequence of SEQ ID NO:18,20 or a variant thereof.

Using the information provided herein, such as a polynucleotide sequence set out in SEQ ID NO:18,20 a polynucleotide of the invention encoding BASB044 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:17,19 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:17,19 was discovered in a DNA library derived from *Neisseria meningitidis*.

Moreover, each DNA sequence set out in SEQ ID NO:17, 19 contains an open reading frame encoding a protein having about the number of amino acid residues set forth in SEQ ID NO:18,20 with a deduced molecular weight that can be calculated using amino acid residue molecular weight values well known to those skilled in the art.

The polynucleotide of SEQ ID NO:17, between the start codon at nucleotide number 1 and the stop codon which begins at nucleotide number 1399 of SEQ ID NO:17, encodes the polypeptide of SEQ ID NO:18.

The polynucleotide of SEQ ID NO:19, between the start codon at nucleotide number 1 and the stop codon which begins at nucleotide number 1327 of SEQ ID NO:19, encodes the polypeptide of SEQ ID NO:20.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:17,19 over the entire length of SEQ ID NO:17,19 respectively; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:18,20 over the entire length of SEQ ID NO:18,20 respectively.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:17,19 or a fragment thereof; and isolating a full-length gene and/or genomic clones containing said polynucleotide sequence.

The invention provides a polynucleotide sequence identical over its entire length to a coding sequence (open reading frame) in SEQ ID NO:17,19. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB044 polypeptide of SEQ ID NO:18,20 may be identical to the polypeptide encoding sequence contained in nucleotides 1 to 1398 of SEQ ID NO:17, or the polypeptide encoding sequence contained in nucleotides 1 to 1326 of SEQ ID NO:19 respectively. Alternatively it may be a sequence, which as a result of the redundancy (degeneracy) of the genetic code, also encodes the polypeptide of SEQ ID NO:18,20.

The term "polynucleotide encoding a polypeptide" as used herein encompasses polynucleotides that include a sequence encoding a polypeptide of the invention, particularly a bacterial polypeptide and more particularly a polypeptide of the Neisseria meningitidis BASB044 having an amino acid sequence set out in SEQ ID NO:18,20. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:18,20. Fragments of polynucleotides of the invention may be used, for example, to synthesize full-length polynucleotides of the invention.

Further particularly preferred embodiments are polynucleotides encoding BASB044 variants, that have the amino acid sequence of BASB044 polypeptide of SEQ ID NO:18,20 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB044 polypeptide.

Further preferred embodiments of the invention are polynucleotides that are at least 85% identical over their entire length to a polynucleotide encoding BASB044 polypeptide having an amino acid sequence set out in SEQ ID NO:18, 20 and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:17,19.

In accordance with certain preferred embodiments of this invention there are provided polynucleotides that hybridize, particularly under stringent conditions, to BASB044 polynucleotide sequences, such as those polynucleotides in SEQ ID NO:17,19.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:17,19 under stringent hybridization conditions with a probe having the sequence of said polynucleotide sequence set forth in SEQ ID NO:17,19 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB044 and to isolate cDNA and genomic clones of other genes that have a high identity, particularly high sequence identity, to the BASB044 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB044 gene may be isolated by screening using a DNA sequence provided in SEQ ID NO:17, 19 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

It is an object of the invention to provide polynucleotides that encode BASB048 polypeptides, particularly polynucleotides that encode the polypeptide herein designated BASB048.

In a particularly preferred embodiment of the invention the polynucleotide comprises a region encoding BASB048 polypeptides comprising a sequence set out in SEQ ID NO:25 which includes a full length gene, or a variant thereof.

The BASB048 polynucleotide provided in SEQ ID NO:25 is the BASB048 polynucleotide from Neisseria meningitidis strains ATCC13090.

As a further aspect of the invention there are provided isolated nucleic acid molecules encoding and/or expressing BASB048 polypeptides and polynucleotides, particularly Neisseria meningitidis BASB048 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB048 polypeptide having a deduced amino acid sequence of SEQ ID NO:26 and polynucleotides closely related thereto and variants thereof.

In another particularly preferred embodiment of the invention there is a BASB048 polypeptide from *Neisseria meningitidis* comprising or consisting of an amino acid sequence of SEQ ID NO:26 or a variant thereof.

Using the information provided herein, such as a polynucleotide sequence set out in SEQ ID NO:25 a polynucleotide of the invention encoding BASB048 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:25 typically a library of clones of chromosomal DNA of *Neisseria meningitidis* in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:25 was discovered in a DNA library derived from *Neisseria meningitidis.*

Moreover, each DNA sequence set out in SEQ ID NO:25 contains an open reading frame encoding a protein having about the number of amino acid residues set forth in SEQ ID NO:26 with a deduced molecular weight that can be calculated using amino acid residue molecular weight values well known to those skilled in the art.

The polynucleotide of SEQ ID NO:25, between the start codon at nucleotide number 1 and the stop codon which begins at nucleotide number 1402 of SEQ ID NO:25, encodes the polypeptide of SEQ ID NO:26.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97-99% or exact identity to SEQ ID NO:25 over the entire length of SEQ ID NO:25; or (b) a polynucleotide sequence encoding a polypeptide which has at least 85% identity, more preferably at least 90% identity, yet more preferably at least 95% identity, even more preferably at least 97-99% or 100% exact, to the amino acid sequence of SEQ ID NO:26 over the entire length of SEQ ID NO:26.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45-65° C. and an SDS concentration from 0.1-1%) with a labeled or detectable probe consisting of or comprising the sequence of SEQ ID NO:25 or a fragment thereof; and isolating a full-length gene and/or genomic clones containing said polynucleotide sequence.

The invention provides a polynucleotide sequence identical over its entire length to a coding sequence (open reading frame) in SEQ ID NO:25. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821-824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB048 polypeptide of SEQ ID NO:26 may be identical to the polypeptide encoding sequence contained in nucleotides 1 to 1401 of SEQ ID NO:25. Alternatively it may be a sequence, which as a result of the redundancy (degeneracy) of the genetic code, also encodes the polypeptide of SEQ ID NO:26.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB048 having an amino acid sequence set out in SEQ ID NO:26. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:26. Fragments of polynucleotides of the invention may be used, for example, to synthesize full-length polynucleotides of the invention.

Further particularly preferred embodiments are polynucleotides encoding BASB048 variants, that have the amino acid sequence of BASB048 polypeptide of SEQ ID NO:26 in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of BASB048 polypeptide.

Further preferred embodiments of the invention are polynucleotides that are at least 85% identical over their entire length to a polynucleotide encoding BASB048 polypeptide having an amino acid sequence set out in SEQ ID NO:26, and polynucleotides that are complementary to such polynucleotides. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:25.

In accordance with certain preferred embodiments of this invention there are provided polynucleotides that hybridize, particularly under stringent conditions, to BASB048 polynucleotide sequences, such as those polynucleotides in SEQ ID NO:25.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:25 under stringent hybridization conditions with a probe having the sequence of said polynucleotide sequence set forth in SEQ ID NO:25 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding BASB048 and to isolate cDNA and genomic clones of other genes that have a high identity, particularly high sequence identity, to the BASB048 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB048 gene may be isolated by screening using a DNA sequence provided in SEQ ID NO:25 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., PNAS USA 85: 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NOS:1-6,11,12, 17-20,25,26 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolff et al., Hum Mol Genet (1992) 1: 363, Manthorpe et al., Hum. Gene Ther. (1983) 4: 419), delivery of DNA complexed with specific protein carriers (Wu et al., J Biol Chem. (1989) 264: 16985), coprecipitation of DNA with calcium phosphate (Benvenisty & Reshef, PNAS USA, (1986) 83: 9551), encapsulation of DNA in various forms of liposomes (Kaneda et al., Science (1989) 243: 375), particle bombardment (Tang et al., Nature (1992) 356:152, Eisenbraun et al., DNA Cell Biol (1993) 12: 791) and in vivo infection using cloned retroviral vectors (Seeger et al., PNAS USA (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, E. coli, streptomyces, cyanobacteria, Bacillus subtilis, Moraxella catarrhalis, Haemophilus influenzae and Neisseria meningitidis; fungal cells, such as cells of a yeast, Kluveromyces, Saccharomyces, a basidiomycete, Candida albicans and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia, fowlpox, canarypox), alphaviruses (Sindbis virus, Semliki Forest Virus, Venezuelian Equine Encephalitis Virus), adenoviruses, adeno-associated virus, picornaviruses (poliovirus, rhinovirus), herpesviruses (varicella zoster virus, etc), Listeria, Salmonella, Shigella, Neisseria, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of BASB041, BASB043, BASB044 or BASB048 polynucleotides and polypeptides of the invention for use as diagnostic reagents. Detection of BASB041, BASB043, BASB044 or BASB048 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB041, BASB043, BASB044 or BASB048 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB041, BASB043. BASB044 or BASB048 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397-4401 (1985).

In another embodiment, an array of oligonucleotides probes comprising a BASB041, BASB043, BASB044 or BASB048 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit which comprises:
(a) a polynucleotide of the present invention, preferably the nucleotide sequence of SEQ ID NO:1,3,5,11,17,19,25 or a fragment thereof;
(b) a nucleotide sequence complementary to that of (a);
(c) a polypeptide of the present invention, preferably the polypeptide of SEQ ID NO:2,4, 6,12,18,20,26 or a fragment thereof; or
(d) an antibody to a polypeptide of the present invention, preferably to the polypeptide of SEQ ID NO:2,4,6,12,18, 20,26.

It will be appreciated that in any such kit, (a), (b), (c) or (d) may comprise a substantial component. Such a kit will be of use in diagnosing a disease or susceptibility to a disease, among others.

This invention also relates to the use of polynucleotides of the present invention as diagnostic reagents. Detection of a mutated form of a polynucleotide of the invention, preferable, SEQ ID NO:1,3,5,11,17,19,25 which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB041, BASB043, BASB044 or BASB048 polypeptide can be used to identify and analyze mutations.

The invention further provides primers with 1, 2, 3 or 4 nucleotides removed from the 5' and/or the 3' end. These primers may be used for, among other things, amplifying BASB041, BASB043, BASB044 or BASB048 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing disease, preferably bacterial infections, more preferably infections caused by *Neisseria meningitidis*, comprising determining from a sample derived from an individual, such as a bodily material, an increased level of expression of polynucleotide having a sequence of SEQ ID NO:1,3,5,11,17,19, 25. Increased or decreased expression of a BASB041, BASB043, BASB044 or BASB048 polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of BASB041, BASB043, BASB044 or BASB048 polypeptide compared to normal control tissue samples may be used to detect the presence of an infection, for example. Assay techniques that can be used to determine levels of a BASB041, BASB043, BASB044 or BASB048 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probe obtained or derived from a bodily sample, to determine the presence of a particular polynucleotide sequence or related sequence in an individual. Such a presence may indicate the presence of a pathogen, particularly *Neisseria meningitidis*, and may be useful in diagnosing and/or prognosing disease or a course of disease. A grid comprising a number of variants of the polynucleotide sequence of SEQ ID NO:1,3,5,11,17,19,25 are preferred. Also preferred is a grid comprising a number of variants of a polynucleotide sequence encoding the polypeptide sequence of SEQ ID NO:2,4,6,12,18,20,26.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against BASB041, BASB043, BASN044 or BASB048 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495-497 (1975); Kozbor et al., *Immunology Today* 4: 72 (1983); Cole et al., pg. 77-96 in *MONOCLONAL ANTIBODIES AND CANCER THERAPY*, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB041, BASB043, BASB044 or BASB048 or from naive libraries (McCafferty, et al., (1990), Nature 348, 552-554; Marks, et al., (1992) *Biotechnology* 10, 779-783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB041, BASB043, BASB044 or BASB048-polypeptide or BASB041, BASB043, BASB044 or BASB048-polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al. (1986), *Nature* 321, 522-525 or Tempest et al., (1991) *Biotechnology* 9, 266-273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB041, BASB043, BASB044 or BASB048 polypeptide and/or polynucleotide activity in the mixture, and comparing the BASB041, BASB043, BASB044 or BASB048 polypeptide and/or polynucleotide activity of the mixture to a standard. Fusion proteins, such as those made from Fc portion and BASB041, BASB043, BASB044 or BASB048 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52-58 (1995); and K. Johanson et al., J Biol Chem, 270(16):9459-9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB041, BASB043, BASB044 or BASB048 polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB041, BASB043, BASB044 or BASB048 polypeptide and a labeled substrate or ligand of such polypeptide is incubated in the absence or the presence of a candidate molecule that may be a BASB041, BASB043, BASB044 or BASB048 agonist or antagonist. The ability of the candidate molecule to agonize or antagonize the BASB041, BASB043, BASB044 or BASB048 polypeptide is reflected in decreased binding of the labeled ligand or decreased production of product from such substrate. Molecules that bind gratuitously, i.e., without inducing the effects of BASB041, BASB043, BASB044 or BASB048 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in BASB041, BASB043, BASB044 or BASB048 polynucleotide or polypeptide activity, and binding assays known in the art.

Another example of an assay for BASB041, BASB043, BASB044 or BASB048 agonists is a competitive assay that combines BASB041, BASB043, BASB044 or BASB048 and a potential agonist with BASB041, BASB043, BASB044 or BASB048-binding molecules, recombinant BASB041, BASB043, BASB044 or BASB048 binding molecules, natural substrates or ligands, or substrate or ligand mimetics, under appropriate conditions for a competitive inhibition assay. BASB041, BASB043, BASB044 or BASB048 can be labeled, such as by radioactivity or a colorimetric compound, such that the number of BASB041, BASB043, BASB044 or BASB048 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB041, BASB043, BASB044 or BASB048-induced activities, thereby preventing the action or expression of BASB041, BASB043, BASB044 or BASB048 polypeptides and/or polynucleotides by excluding BASB041, BASB043, BASB044 or BASB048 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, J. Neurochem. 56: 560 (1991); OLIGODEOXYNUCLEOTIDES AS ANTISENSE INHIBITORS OF GENE EXPRESSION, CRC Press, Boca Raton, Fla. (1988), for a description of these molecules). Preferred potential antagonists include compounds related to and variants of BASB041, BASB043, BASB044 or BASB048.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial BASB041, BASB043, BASB044 or BASB048 proteins that mediate tissue damage and/or; to block the normal progression of pathogenesis in infections initiated other than by the implantation of in-dwelling devices or by other surgical techniques.

In accordance with yet another aspect of the invention, there are provided BASB041, BASB043, BASB044 or BASB048 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB041, BASB043, BASB044 or BASB048 polynucleotide and/or polypeptide, or a fragment or variant thereof, adequate to produce antibody and/or T cell immune response to protect said individual from infection, particularly bacterial infection and most particularly *Neisseria meningitidis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB041, BASB043, BASB044 or BASB048 polynucleotide and/or polypeptide, or a fragment or a variant thereof, for expressing BASB041, BASB043, BASB044 or BASB048 polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB041, BASB043, BASB044 or BASB048 polynucleotide and/or polypeptide encoded therefrom, wherein the composition comprises a recombinant BASB041, BASB043, BASB044 or BASB048 polynucleotide and/or polypeptide encoded therefrom and/or comprises DNA and/or RNA which encodes and expresses an antigen of said BASB041, BASB043, BASB044 or BASB048 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A BASB041, BASB043, BASB044 or BASB048 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

In a vaccine composition according to the invention, a BASB041, BASB043, BASB044 or BASB048 polypeptide and/or polynucleotide, or a fragment, or a mimotope, or a variant thereof may be present in a vector, such as the live recombinant vectors described above for example live bacterial vectors.

Also suitable are non-live vectors for the BASB041, BASB043, BASB044 or BASB048 polypeptide, for example bacterial outer-membrane vesicles or "blebs". OM blebs are derived from the outer membrane of the two-layer membrane of Gram-negative bacteria and have been documented in many Gram-negative bacteria (Zhou, L et al. 1998. *FEMS Microbiol. Lett.* 163:223-228) including *C. trachomatis* and *C. psittaci*. A non-exhaustive list of bacterial pathogens reported to produce blebs also includes: *Bordetella pertussis, Borrelia burgdorferi, Brucella melitensis, Brucella ovis, Esherichia coli, Haemophilus influenza, Legionella pneumophila, Neisseria gonorrhoeae, Neisseria meningitidis, Pseudomonas aeruginosa* and *Yersinia enterocolitica*.

Blebs have the advantage of providing outer-membrane proteins in their native conformation and are thus particularly useful for vaccines. Blebs can also be improved for vaccine use by engineering the bacterium so as to modify the expression of one or more molecules at the outer membrane. Thus for example the expression of a desired immunogenic protein at the outer membrane, such as the BASB041, BASB043, BASB044 or BASB048 polypeptide, can be introduced or upregulated (e.g. by altering the promoter). Instead or in addition, the expression of outer-membrane molecules which are either not relevant (e.g. unprotective antigens or immunodominant but variable proteins) or detrimental (e.g. toxic molecules such as LPS, or potential inducers of an autoimmune response) can be downregulated. These approaches are discussed in more detail below.

The non-coding flanking regions of the BASB041, BASB043, BASB044 or BASB048 gene contain regulatory elements important in the expression of the gene. This regulation takes place both at the transcriptional and translational level. The sequence of these regions, either upstream or downstream of the open reading frame of the gene, can be obtained by DNA sequencing. This sequence information allows the determination of potential regulatory motifs such as the different promoter elements, terminator sequences, inducible sequence elements, repressors, elements responsible for phase variation, the shine-dalgarno sequence, regions with potential secondary structure involved in regulation, as well as other types of regulatory motifs or sequences.

This sequence information allows the modulation of the natural expression of the BASB041, BASB043, BASB044 or BASB048 gene. The upregulation of the gene expression may be accomplished by altering the promoter, the shine-dalgarno sequence, potential repressor or operator elements, or any other elements involved. Likewise, downregulation of expression can be achieved by similar types of modification. Alternatively, by changing phase variation sequences, the expression of the gene can be put under phase variation control, or it may be uncoupled from this regulation. In another approach, the expression of the gene can be put under the control of one or more inducible elements allowing regulated expression. Examples of such regulation include, but are not limited to, induction by temperature shift, addition of inductor substrates like selected carbohydrates or their derivatives, trace elements, vitamins, co-factors, metal ions, etc.

Such modifications as described above can be introduced by several different means. The modification of sequences involved in gene expression can be carried out in vivo by random mutagenesis followed by selection for the desired phenotype. Another approach consists in isolating the region of interest and modifying it by random mutagenesis, or site-directed replacement, insertion or deletion mutagenesis. The modified region can then be reintroduced into the bacterial genome by homologous recombination, and the effect on gene expression can be assessed. In another approach, the sequence knowledge of the region of interest can be used to replace or delete all or part of the natural regulatory sequences. In this case, the regulatory region targeted is isolated and modified so as to contain the regulatory elements from another gene, a combination of regulatory elements from different genes, a synthetic regulatory region, or any other regulatory region, or to delete selected parts of the wild-type regulatory sequences. These modified sequences can then be reintroduced into the bacterium via homologous recombination into the genome. A non-exhaustive list of preferred promoters that could be used for up-regulation of gene expression includes the promoters porA, porB, lbpB, tbpB, p110, 1st, hpuAB from *N. meningitidis* or *N. gonorroheae*; ompCD, copB, lbpB, ompE, UspA1; UspA2; TbpB from *M. Catarrhalis*; p1, p2, p4, p5, p6, lpD, tbpB, D15, Hia, Hmw1, Hmw2 from *H. influenzae*.

In one example, the expression of the gene can be modulated by exchanging its promoter with a stronger promoter (through isolating the upstream sequence of the gene, in vitro modification of this sequence, and reintroduction into the genome by homologous recombination). Upregulated expression can be obtained in both the bacterium as well as in the outer membrane vesicles shed (or made) from the bacterium.

In other examples, the described approaches can be used to generate recombinant bacterial strains with improved characteristics for vaccine applications. These can be, but are not limited to, attenuated strains, strains with increased expression of selected antigens, strains with knock-outs (or decreased expression) of genes interfering with the immune response, strains with modulated expression of immunodominant proteins, strains with modulated shedding of outer-membrane vesicles.

Thus, also provided by the invention is a modified upstream region of the BASB041, BASB043, BASB044 or BASB048 gene, which modified upstream region contains a heterologous regulatory element which alters the expression level of the BASB041, BASB043, BASB044 or BASB048 protein located at the outer membrane. The upstream region according to this aspect of the invention includes the sequence upstream of the BASB041, BASB043, BASB044 or BASB048 gene. The upstream region starts immediately upstream of the BASB041, BASB043, BASB044 or BASB048 gene and continues usually to a position no more than about 1000 bp upstream of the gene from the ATG start codon. In the case of a gene located in a polycistronic sequence (operon) the upstream region can start immediately preceding the gene of interest, or preceding the first gene in the operon. Preferably, a modified upstream region according to this aspect of the invention contains a heterologous promotor at a position between 500 and 700 bp upstream of the ATG.

Thus, the invention provides a BASB041, BASB043, BASB044 and BASB048 polypeptide, in a modified bacterial bleb. The invention further provides modified host cells capable of producing the non-live membrane-based bleb vectors. The invention further provides nucleic acid vectors comprising the BASB041, BASB043, BASB044 and BASB048 gene having a modified upstream region containing a heterologous regulatory element.

Further provided by the invention are processes to prepare the host cells and bacterial blebs according to the invention.

Also provided by this invention are compositions, particularly vaccine compositions, and methods comprising the polypeptides and/or polynucleotides of the invention and immunostimulatory DNA sequences, such as those described in Sato, Y. et al. Science 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with *Neisseria meningitidis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Neisseria meningitidis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ ve T cell clones by Mosmann and Coffman (*Mosmann, T. R.* and *Coffan, R. L.* (1989) *TH1 and TH2 cells: different patterns of lymphokine secretion lead to different functional properties. Annual Review of Immunology*, 7, p 145-173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6 and IL-13.

It is known that certain vaccine adjuvants are particularly suited to the stimulation of either TH1 or TH2-type cytokine responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454).

3D-MPL will be present in the range of 10 μg-100 μg preferably 25-50 μg per dose wherein the antigen will typically be present in a range 2-50 μg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with a carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21: 3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg-200 μg, such as 10-100 μg, preferably 10 μg-50 μg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB041, BASB043, BASB044 and BASB048 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

The antigen can also be delivered in the form of whole bacteria (dead or alive) or as subcellular fractions, these possibilities do include *N. meningitidis* itself.

Compositions, Kits and Administration

In a further aspect of the invention there are provided compositions comprising a BASB041, BASB043, BASB044 or BASB048 polynucleotide and/or a BASB041, BASB043, BASB044 or BASB048 polypeptide for administration to a cell or to a multicellular organism.

The invention also relates to compositions comprising a polynucleotide and/or a polypeptide discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1-100 μg/kg of subject.

A vaccine composition is conveniently in injectable form. Conventional adjuvants may be employed to enhance the immune response. A suitable unit dose for vaccination is 0.5-5 microgram/kg of antigen, and such dose is preferably administered 1-3 times and with an interval of 1-3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Definitions

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J. Mol. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md. 20894; Altschul, S., et al., *J. Mol. Biol.* 215: 403-410 (1990). The well known Smith Waterman algorithm may also be used to determine identity.

Parameters for polypeptide sequence comparison include the following:
Algorithm: Needleman and Wunsch, J. Mol. Biol. 48: 443-453 (1970)
Comparison matrix: BLOSSUM62 from Henikoff and Henikoff, Proc. Natl. Acad. Sci. USA. 89:10915-10919 (1992)
Gap Penalty: 8
Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:
Algorithm: Needleman and Wunsch, J. Mol. Biol. 48: 443-453 (1970)
Comparison matrix: matches=+10, mismatch=0
Gap Penalty: 50
Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, upper respiratory tract infection, invasive bacterial diseases, such as bacteremia and meningitis.

EXAMPLES

The examples below are carried out using standard techniques, which are well known and routine to those of skill in the art, except where otherwise described in detail. The examples are illustrative, but do not limit the invention.

Example 1

DNA Sequencing of the BASB041 Gene from Two *N. meningitidis* Strains.

A: BASB041 in *N. meningitidis* serogroup B strain ATCC13090.

The BASB041 gene of *N. meningitidis* strain ATCC 13090 is shown in SEQ ID NO:1 The translation of the BASB041 polynucleotide sequence, shown in SEQ ID NO:2, shows significant similarity (28% identity in a 130 amino acids overlap) to a hypothetical protein of *Aquifex aeolicus*. The BASB041 polypeptide contains a signal sequence characteristic of a lipoprotein, and could thus be inserted into the outer membrane of the bacterium.

The sequence of the BASB041 gene was further confirmed as follows. For this purpose, genomic DNA was extracted from $10^{10}$ cells of the *N. meningitidis* cells (strain ATCC 13090) using the QIAGEN genomic DNA extraction kit (Qiagen Gmbh), and 1 μg of this material was submitted to Polymerase Chain Reaction DNA amplification using primers lip5-01 (5'-AAT GAA AAC CGT TTC CAC CGC-3') [SEQ ID NO:7] and lip5-02 (5'-TCA TTT CTC CTT AAC GGT-3') [SEQ ID NO:8]. This PCR product was gel-purified and subjected to DNA sequencing using the Big Dye Cycle Sequencing kit (Perkin-Elmer) and an ABI 373A/PRISM DNA sequencer. DNA sequencing was performed on both strands with a redundancy of 2 and the full-length sequence was assembled using the SeqMan program from the DNASTAR Lasergene software package. The resulting DNA sequence and deduced polypeptide sequence are shown as SEQ ID NO:3 and SEQ ID NO:4 respectively. It should be noticed that the DNA sequence of SEQ ID NO:3 has an additional nucleotide at position 616 relative to SEQ ID NO:1.

B: BASB041 in *N. meningitidis* Serogroup B Strain H44/76.

The sequence of the BASB041 gene was also determined in another *N. meningitidis* serogroup B strain, the strain H44/76. For this purpose, genomic DNA was extracted from the *N. meningitidis* strain H44/76 using the experimental conditions presented in the previous paragraph. This material (1 kg) was then submitted to Polymerase Chain Reaction DNA amplification using primers LipS-01 and Lip5-02 specific for the BASB041 gene. The PCR amplicon was then submitted to DNA sequencing using the Big Dyes kit (Applied biosystems) and analyzed on a ABI 373/A DNA sequencer in the conditions described by the supplier. As a result, the polynucleotide and deduced polypeptide sequences, referred to as SEQ ID NO:5 and SEQ ID NO:6 respectively, were obtained. It should be noticed that the DNA sequence of SEQ ID NO:5 has an additional nucleotide at position 616 relative to SEQ ID NO:1. Using the MegAlign program in the DNASTAR Lasergene package, an alignment of the polynucleotide sequences of SEQ ID NO:1, 3 and 5 was performed, and is displayed in FIG. 1; a pairwise comparison of identities is summarized in Table 1, showing that the three BASB041 polynucleotide gene sequences are all similar at identity level greater than 99.0%. Using the same MegAlign program, an alignment of the polypeptide sequences of SEQ ID NO:2, 4 and 6 was performed, and is displayed in FIG. 2. A pairwise comparison of identities is summarized in Table 2, showing that SEQ ID NO:4 and 6 are 100% identical; their dissimilarity with SEQ ID NO:2 is entirely contained in the last 18 residues, and is due to the missing nucleotide in SEQ ID NO:1 relative to SEQ ID NO:3 and 5.

Taken together, these data inditate strong sequence conservation of the BASB041 gene among the two *N. meningitidis* serogroup B strains.

TABLE 1

Pairwise identities of the BASB041 polynucleotide sequences (in %)

| | SeqID No: 3 | SeqID No: 5 |
|---|---|---|
| SeqID No: 1 | 99.8% | 99.2% |
| SeqID No: 3 | | 99.4% |

TABLE 2

Pairwise identities of the BASB041 polypeptide sequences (in %)

| | SeqID No: 4 | SeqID No: 6 |
|---|---|---|
| SeqID No: 2 | 92.3% | 92.3% |
| SeqID No: 4 | | 100% |

Construction of Plasmid to Express Recombinant BASB041

A: Cloning of BASB041.

The NdeI and SalI restriction sites engineered into the forward Lip5-Fm/p (5'-AGG CAG AGG CAT ATG AAA ACC GTT TCC ACC GCC GTT GTC CTT GC-3') ([SEQ ID NO:9]) and reverse Lip5-RCf/p (5'-AGG CAG AGG GTC GAC TTT CTC CTT AAC GGT TGG GTT GCC ATG CGC-3')([SEQ ID NO:10]) amplification primers, respectively, permitted directional cloning of a BASB041 PCR product into the commercially available *E. coli* expression plasmid pET24b (Novagen, USA, kanamycin resistant) such that a mature BASB041 protein could be expressed as a fusion protein containing a (His)6 affinity chromatography tag at the C-terminus. The BASB041 PCR product was purified from the amplification reaction using silica gel-based spin columns (QiaGen) according to the manufacturers instructions. To produce the required NdeI and SaiI termini necessary for cloning, purified PCR product was sequentially digested to completion with NdeI and SaiI restriction enzymes as recommended by the manufacturer (Life Technologies). Following the first restriction digestion, the PCR product was purified via spin column as above to remove salts and eluted in sterile water prior to the second enzyme digestion. The digested DNA fragment was again purified using silica gel-based spin columns prior to ligation with the pET24b plasmid.

B: Production of Expression Vector.

To prepare the expression plasmid pET24b for ligation, it was similarly digested to completion with both NdeI and SalI and then treated with calf intestinal phosphatase (CIP, ~0.02 units/pmole of 5' end, Life Technologies) as directed by the manufacturer to prevent self-ligation. An approximately 5-fold molar excess of the digested fragment to the prepared vector was used to program the ligation reaction. A standard ~20 μl ligation reaction (~16° C., ~16 hours), using methods well known in the art, was performed using T4 DNA ligase (~2.0 units/reaction, Life Technologies). An aliquot of the ligation (~5 μl) was used to transform electro-competent BL21 DE3 cells according to methods well known in the art. Following a ~2-3 hour outgrowth period at 37° C. in ~1.0 ml of LB broth, transformed cells were plated on LB agar plates containing kanamycin (50 μg/ml. The antibiotic was included in the selection media to ensure that all transformed cells carried the pET24b plasmid (KnR). Plates were incubated overnight at 37° C. for ~16 hours. Individual KnR colonies were picked with sterile toothpicks and used to "patch" inoculate fresh LB KnR plates as well as a ~1.0 ml LB KnR broth culture. Both the patch plates and the broth culture were incubated overnight at 37° C. in either a standard incubator (plates) or a shaking water bath.

A whole cell-based PCR analysis was employed to verify that transformants contained the BASB041 DNA insert. Here, the ~1.0 ml overnight LB Kn broth culture was transferred to a 1.5 ml polypropylene tube and the cells collected by centrifugation in a Beckman microcentrifuge (~3 min., room temperature, ~12,000×g). The cell pellet was suspended in ~200 µl of sterile water and a ~10 µl aliquot used to program a ~50 µl final volume PCR reaction containing both BASB041 forward and reverse amplification primers. Final concentrations of the PCR reaction components were essentially the same as those specified in example 2 except ~5.0 units of Taq polymerase was used. The initial 95° C. denaturation step was increased to 3 minutes to ensure thermal disruption of the bacterial cells and liberation of plasmid DNA. An ABI Model 9700 thermal cycler and a 32 cycle, three-step thermal amplification profile, i.e. 95° C., 45 sec; 55-58° C., 45 sec, 72° C., 1 min., were used to amplify the BASB041 PCR fragment from the lysed transformant samples. Following thermal amplification, a ~20 µl aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the PCR products. Transformants that produced the expected PCR product were identified as strains containing a BASB041 expression construct. Expression plasmid containing strains were then analyzed for the inducible expression of recombinant BASB041.

C: Expression Analysis of PCR-Positive Transformants.

For each PCR-positive transformant identified above, ~5.0 ml of LB broth containing kanamycin (50 µg/ml) was inoculated with cells from the patch plate and grown overnight at 37° C. with shaking (~250 rpm). An aliquot of the overnight seed culture (~1.0 ml) was inoculated into a 125 ml erlenmeyer flask containing ~25 ml of LB Kn broth and grown at 37° C. with shaking (~250 rpm) until the culture turbidity reached O.D.600 of ~0.5, i.e. mid-log phase (usually about 1.5-2.0 hours). At this time approximately half of the culture (~12.5 ml) was transferred to a second 125 ml flask and expression of recombinant BASB041 protein induced by the addition of IPTG (1.0 M stock prepared in sterile water, Sigma) to a final concentration of 1.0 mM. Incubation of both the IPTG-induced and non-induced cultures continued for an additional ~4 hours at 37° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 µl of sterile water, then mixed with an equal volume of 2× Laemelli SDS-PAGE sample buffer containing 2-mercaptoethanol, and placed in boiling water bath for ~3 min to denature protein. Equal volumes (~15 µl) of both the crude IPTG-induced and the non-induced cell lysates were loaded onto duplicate 12% Tris/glycine polyacrylamide gel (1 mm thick Mini-gels, Novex). The induced and non-induced lysate samples were electrophoresed together with prestained molecular weight markers (See Blue, Novex) under conventional conditions using a standard SDS/Tris/glycine running buffer (BioRad). Following electrophoresis, one gel was stained with commassie brilliant blue R250 (BioRad) and then destained to visualize novel BASB041 IPTG-inducible protein(s). The second gel was electroblotted onto a PVDF membrane (0.45 micron pore size, Novex) for ~2 hrs at 4° C. using a BioRad Mini-Protean II blotting apparatus and Towbin's methanol (20%) transfer buffer. Blocking of the membrane and antibody incubations were performed according to methods well known in the art. A monoclonal anti-RGS (His) antibody, followed by a second rabbit anti-mouse antibody conjugated to HRP (QiaGen), was used to confirm the expression and identity of the BASB041 recombinant protein. Visualization of the anti-His antibody reactive pattern was achieved using either an ABT insoluble substrate or using Hyperfilm with the Amersham ECL chemiluminescence system.

Production of Recombinant BASB041

Bacterial Strain

A recombinant expression strain of *E. coli* BL21 DE3 containing a pET24b plasmid encoding BASB041 from *N. meningitidis* was used to produce cell mass for purification of recombinant protein. The expression strain was cultivated on LB agar plates containing 50 μg/ml kanamycin ("Kn") to ensure plasmid maintenance. For cryopreservation at −80° C., the strain was propagated in LB broth containing the same concentration of antibiotic then mixed with an equal volume of LB broth containing 30% (w/v) glycerol.

Media

The fermentation medium used for the production of recombinant protein consisted of 2×YT broth (Difco) containing 50 μg/ml Kn. Antifoam was added to medium for the fermentor at 0.25 ml/L (Antifoam 204, Sigma). To induce expression of the BASB041 recombinant protein, IPTG (Isopropyl β-D-Thiogalactopyranoside) was added to the fermentor (1 mM, final).

Fermentation

A 500-ml erlenmeyer seed flask, containing 50 ml working volume, was inoculated with 0.3 ml of rapidly thawed frozen culture, or several colonies from a selective agar plate culture, and incubated for approximately 12 hours at 37±1° C. on a shaking platform at 150 rpm (Innova 2100, New Brunswick Scientific). This seed culture was then used to inoculate a 5-L working volume fermentor containing 2×YT broth and both Kn antibiotic. The fermentor (Bioflo 3000, New Brunswick Scientific) was operated at 37+1° C., 0.2-0.4 VVM air sparge, 250 rpm in Rushton impellers. The pH was not controlled in either the flask seed culture or the fermentor. During fermentation, the pH ranged 6.5 to 7.3 in the fermentor. IPTG (1.0 M stock, prepared in sterile water) was added to the fermentor when the culture reached mid-log of growth (~0.7 O.D.600 units). Cells were induced for 2-4 hours then harvested by centrifugation using either a 28RS Heraeus (Sepatech) or RC5C superspeed centrifuge (Sorvall Instruments). Cell paste was stored at −20 C until processed.

Purification

Imidazole and biotechnology grade or better reagents were all obtained from Ameresco Chemical, Solon, Ohio. Triton X-100 (t-Octylphenoxypolyethoxy-ethanol), Triton X-114, sodium phosphate, monobasic, and urea were reagent grade or better and obtained from Sigma Chemical Company, St. Louis, Mo. Dulbecco's Phosphate Buffered Saline (1×PBS) was obtained from Quality Biological, Inc., Gaithersburg, Md. Dulbecco's Phosphate Buffered Saline (10×PBS) was obtained from BioWhittaker, Walkersville, Md. Penta-His Antibody, BSA free was obtained from QiaGen, Valencia, Calif. Peroxidase-conjugated AffiniPure Goat Anti-mouse IgG was obtained from Jackson Immuno Research, West Grove, Penn. All other chemicals were reagent grade or better.

Ni-chelatin Sepharose Fast Flow resin was obtained from Pharmacia, Sweden. Precast Tris-Glycine 4-20% and 10-20% polyacrylamide gels, all running buffers and solutions, SeeBlue Pre-Stained Standards, MultiMark Multi-Colored Standards and PVDF transfer membranes were obtained from Novex, San Diego, Calif. SDS-PAGE Silver Stain kits were obtained from Daiichi Pure Chemicals Company Limited, Tokyo, Japan. Coomassie Stain Solution was obtained from Bio-Rad Laboratories, Hercules, Calif. Acrodisc® PF 0.2 m syringe filters were obtained from Pall Gelman Sciences, Ann Arbor, Mich. GD/X 25 mm disposable syringe filters were obtained from Whatman Inc., Clifton, N.J. Dialysis tubing 8,000 MWCO was obtained from BioDesign Inc. Od New York, Carmal New York. BCA Protein Assay Reagents and Snake Skin dialysis tubing 3,500 MWCO were obtained from Pierce Chemical Co., Rockford, Ill.

Extraction Protocol

Cell paste was thawed at room temperature for 30 to 60 minutes. Five to six grams of material was weighed out into a 50-ml disposable centrifuge tube. Recombinant BASB041 antigen was purified by extraction of cell membranes with 1.0% Triton X114, and allowing phase partitioning based on Triton X114 cloud point at 37° C. The Triton X114 phase was diluted with 50 mM Tris-HCl containing 10% glycerol, 5% ethylene glycol and 0.5% Triton X100. This was applied to nickel-chelating Sepharose Fast Flow. The protein is afterwards eluted with 200 mM imidazole to affinity purify the histidine-tagged protein and yielded greater than 90% pure protein.

Binding of BASB041 to Nickel Affinity Resin

After extraction, the mixture was incubated to the nickel-chelating Sepharose Fast Flow and placed at room temperature with gentle agitation for one hour. After one hour, the nickel-chelating Sepharose Fast Flow is packed into an XK16 Pharmacia column, and eluted afterwards with 500 mM imidazole buffer to affinity purify the histidine tagged protein. This fraction was then dialyzed against 25 mM Phosphate buffer (pH7.0) containing 0.1% of Triton. This sample was then applied to a TOYOPEARL BUTYL_650M column which was equilibrated with 25 mM Phosphate buffer (pH7.0) containing 2M sodium chloride and 0.1% of Triton. Elution was performed in the following buffer with 25 mM Phosphate buffer (pH7.0) containing 1M sodium chloride and 0.1% of Triton. This fraction was further applied to a DEAE-sepharose-FF in presence of 50 mM tris(pH7.5) containing 2 mMEDTA, 10 mMsodium chloride and 0.005% Triton X100. The DEAE flowthrough was dialyzed against PBS (pH7.4) containing 0.1% of Triton and stored at −70 at a concentration of 490 μg/ml.

Final Formulation

BASB041 was formulated by dialysis overnight against, three changes of 0.1% Triton X-100 and 1×PBS, pH 7.4. The purified protein was characterized and used to produce antibodies as described below.

Biochemical Characterizations: SDS-PAGE and Western Blot Analysis

The recombinant purified protein was resolved on 4-20% polyacrylamide gels and electrophoretically transferred to PVDF membranes at 100 V for 1 hour as previously described (Thebaine et al. 1979, Proc. Natl. Acad. Sci. USA 76:4350-4354). The PVDF membranes were then pretreated with 25 ml of Dulbecco's phosphate buffered saline containing 5% non-fat dry milk. All subsequent incubations were carried out using this pretreatment buffer.

PVDF membranes were incubated with a dilution of anti-His tail antibodies for 1 hour at room temperature. PVDF membranes were then washed twice with wash buffer (20 mM Tris buffer, pH 7.5, containing 150 mM sodium chloride and 0.05% Tween-20). PVDF membranes were incubated with 25 ml of a 1:5000 dilution of peroxidase-labeled species specific conjugate for 30 minutes at room temperature. PVDF membranes were then washed 4 times with wash buffer, and were developed with 3-amino-9-ethylcarbazole and urea peroxide as supplied by Zymed (San Francisco, Calif.) for 10 minutes each.

The results of an SDS-PAGE (FIG. 3) show a protein about 31 kDa purified to greater than 90% and that is reactive to an anti-RGS (His) antibody by western blots (FIG. 3) of the SDS-PAGE.

Immunization of Mice with Recombinant BASB041

Partially purified recombinant BASB041 protein expressed in *E. coli* has been injected three times in Balb/C mice on days 0, 14 and 28 (10 animals/group). Animals were injected by the subcutaneous route with around 5 μg of antigen in two different formulations: either adsorbed on 100 μg $AlPO_4$ or formulated in SBAS2 emulsion (SB62 emulsion containing 5 μg MPL and 5 μg QS21 per dose). A negative control group consisting of mice immunized with the SBAS2 emulsion only has also been added in the experiment. Mice were bled on days 28 (14 days Post II) and 35 (7 days Post III) in order to detect specific anti-BASB041 antibodies. Specific anti-BASB041 antibodies were measured by western-blotting on pooled sera (from 10 mice/group) from both formulations (on day 7 Post III only), using recombinant protein (part of the gel) and *Neisseria meningitidis* B strains.

Recognition of the BASB041 epitopes on different *Neisseria meningitidis Serogroup* B strains by western-blotting In this test, immunized mice sera (pooled) have been tested by western-blotting for recognition of the BASB041 epitopes on seven different *Neisseria meningitidis* B strains: H44/76 (B:15:P1.7, 16, lineage ET-5), M97 250687 (B:4:P1.15), BZ10 (B:2b:P1.2, lineage A4), BZ198 (B:NT*: -, lineage 3), EG328 (B:NT*, lineage ST-18), NGP165 (B:2a:P1.2, ET 37 cluster) and the ATCC 13090 (B:15:P1.15) *Neisseria meningitidis* B strains, as well as on partially purified recombinant BASB041 protein. (*: NT: Not Typed).

Briefly, 10 μl (>$10^8$ cells/lane) of each sample treated with sample buffer (10 min at 95° C.) are put into a SDS-PAGE gradient gel (Tris-glycine 4-20%, Novex, code no EC60252). Electrophoretic migration occurs at 125 volts for 90 min. Afterwards, proteins are transferred to nitrocellulose sheet (0.45 μm, Bio-rad code no 162-0114) at 100 volts for 1 hour using a Bio-rad Trans-blot system (code no 170-3930). Filter was blocked with PBS-0.05% Tween 20 overnight at room temperature, before incubation with the mice sera containing the anti-BASB041 antibodies from both $AlPO_4$ and SBAS2 formulations. These sera are diluted 100 times in PBS-0.05% Tween 20, and incubated on the nitrocellulose sheet for two hours at room temperature with gentle shaking, using a mini-blotter system (Miniprotean, Bio-rad code no 170-4017). After three repeated washing steps in PBS-0.05% Tween 20 for 5 min., the nitrocellulose sheet is incubated at room temperature for 1 hour under gentle shaking with the appropriate conjugate (biotinylated anti-mouse Ig antibodies from sheep, Amersham code no RPN1001) diluted at 1/500 in the same washing buffer. The membrane is washed three times as previously, and incubated for 30 min with agitation using the streptavidin-peroxidase complex (Amersham code no 1051) diluted at 1/1000 in the washing buffer. After the last three repeated washing steps, the revelation occurs during the 20 min incubation time in a 50 ml solution containing 30 mg 4-chloro-1-naphtol (Sigma), 10 ml methanol, 40 ml PBS, and 30 µl of $H_2O_2$. The staining is stopped while washing the membrane several times in distilled water.

Figure 4:
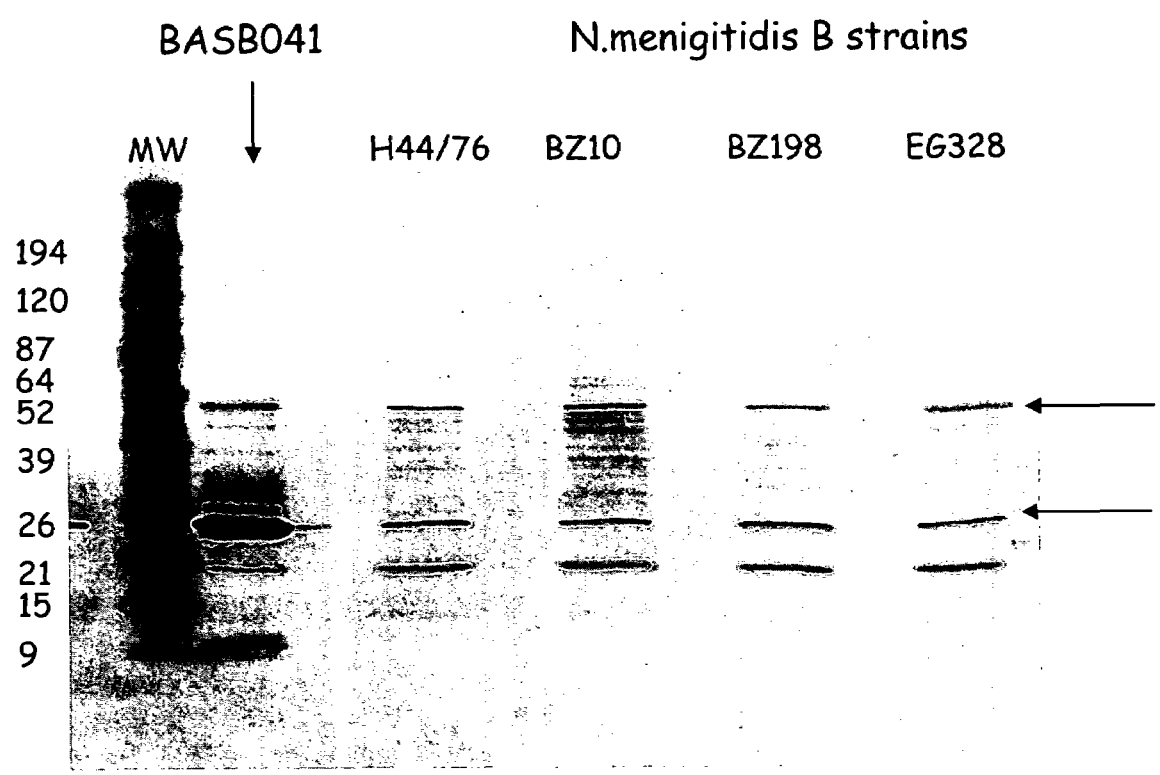
FIG. 4 shows a Western blot for recognition of BASB041 protein in several *Neisseria meningitidis* strains with BASB041 immunized mice sera.
Figure 5:
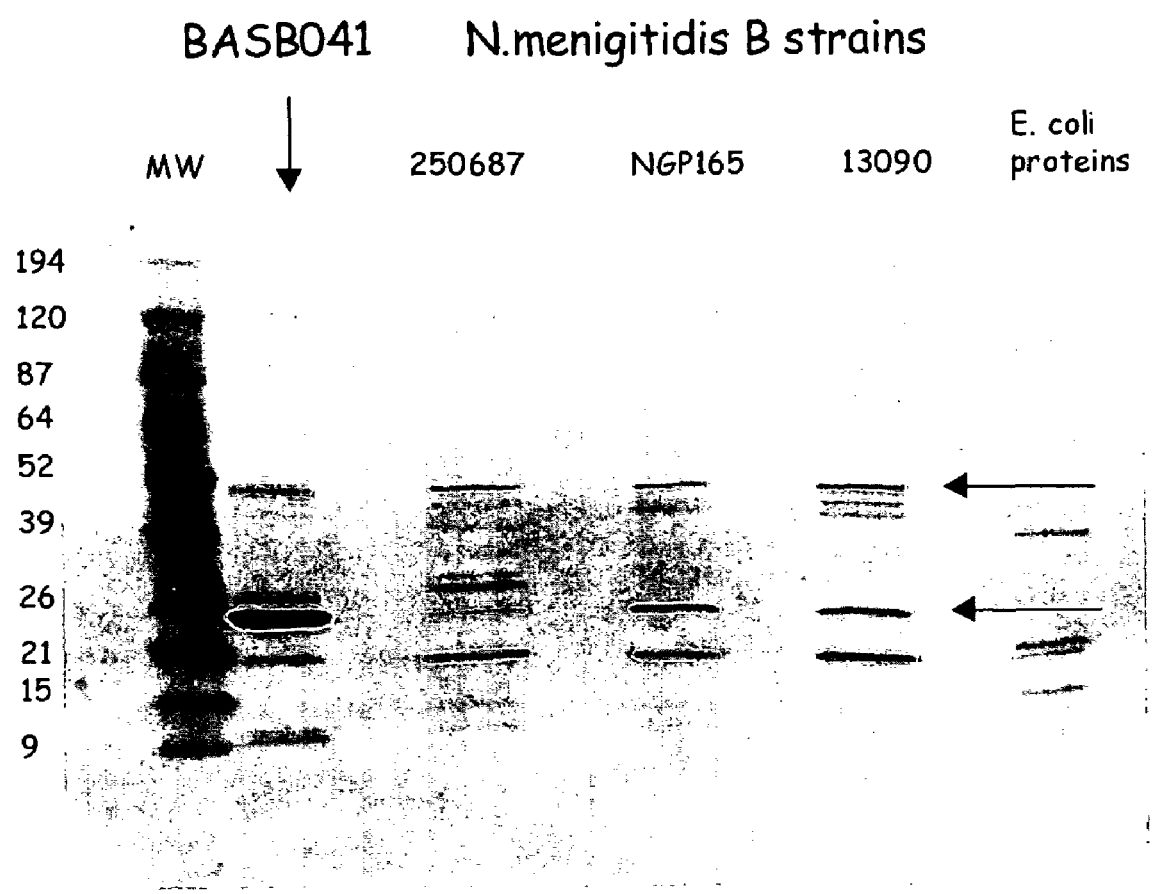
FIG. 5 shows a Western blot for recognition of BASB041 protein in several *Neisseria meningitidis* strains with BASB041 immunized mice sera.

Results illustrated in FIGS. 4 and 5 show that all strains tested present the expected bands around 25-30 kDa (major) and 50 kDa (minor), which are recognized at the same level in all of the *Neisseria meningitidis* B strains tested. This means that the BASB041 protein is expressed in probably all *Neisseria meningitidis* B strains. In both figures, the recombinant BASB041 protein is also clearly recognized by mice sera at the same MW (second lane after the MW). Another band at around 20 kDa is known to be non-specific. This BASB041 protein is not recognized anymore in *E. coli* preparation.

Presence of Anti-BASB041 Antibodies in Sera from Convalescent Patients.

In this test, several convalescent sera have been tested by western-blotting for recognition of the purified recombinant BASB041 protein.

Figure 6:
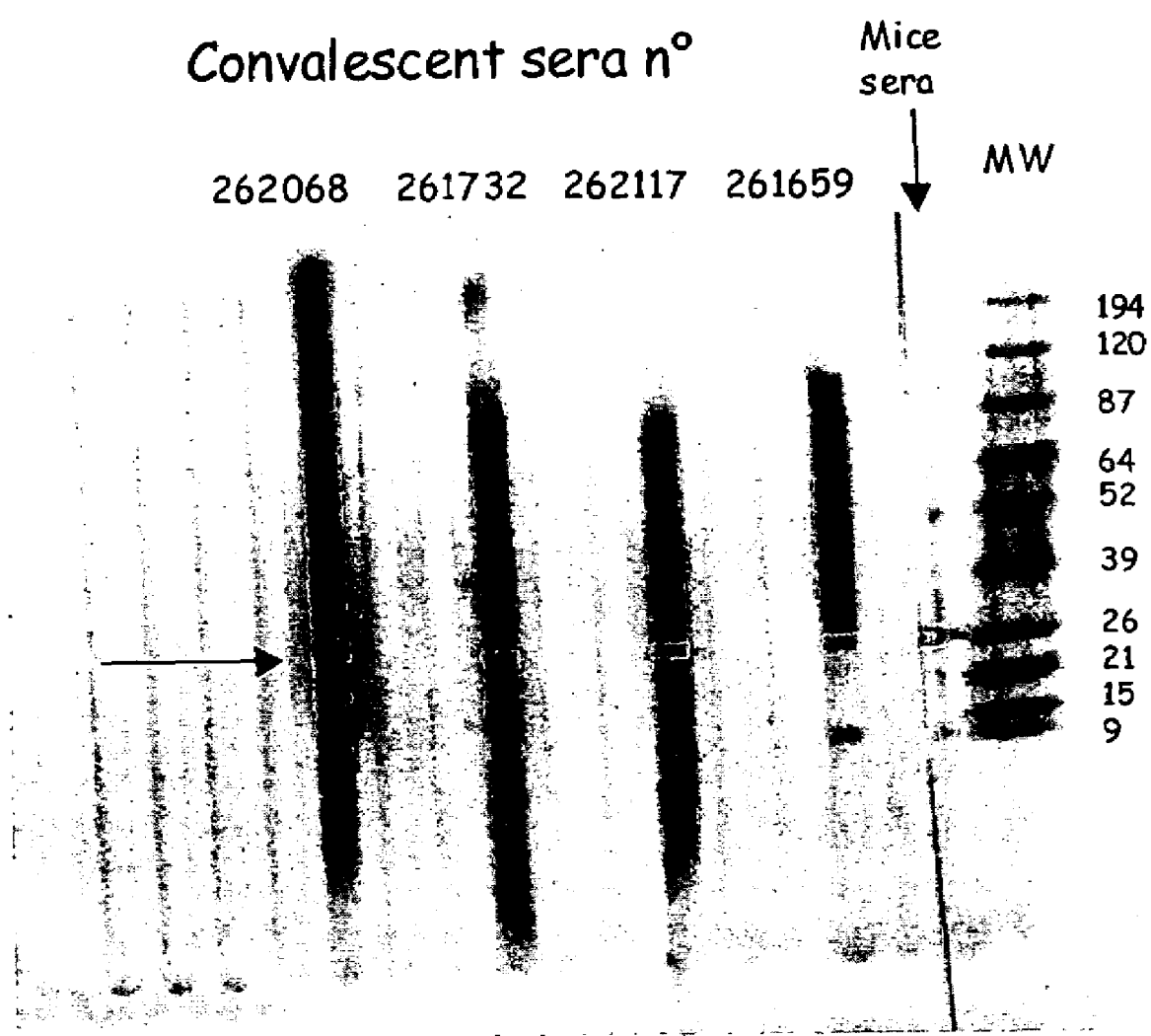
FIG. 6 shows a Western blot for recognition of BASB041 protein in convalescent sera and immunized mice.
Figure 7:
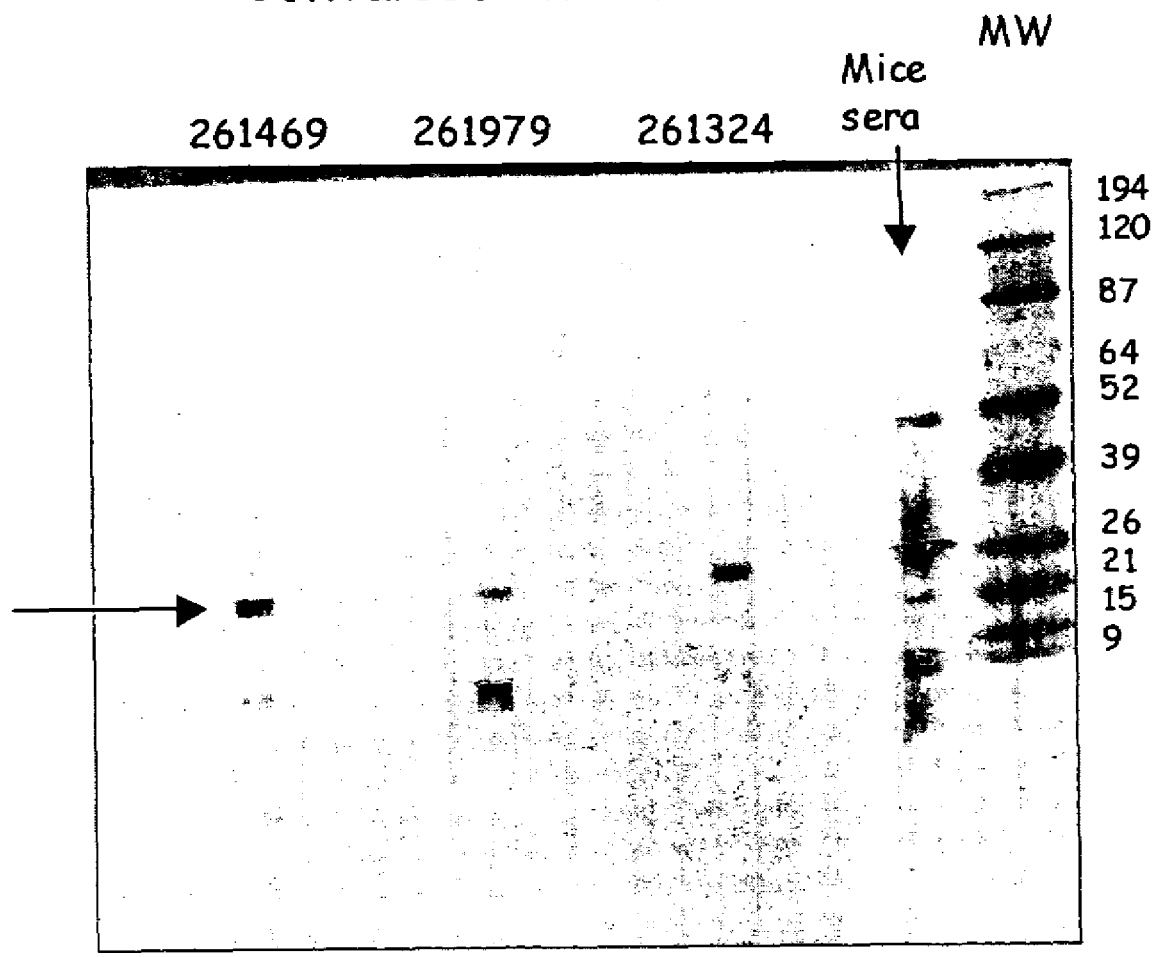
FIG. 7 shows a Western blot for recognition of BASB041 protein in convalescent sera and immunized mice.

Briefly, 5 µg of partially purified BASB041 *Neisseria meningitidis* B protein are put into a SDS-PAGE gradient gel (4-20%, Novex, code no EC60252) for electrophoretic migration. Proteins are transferred to nitrocellulose sheet (0.45 µm, Bio-rad code no 162-0114) at 100 volts for 1 hour using a Bio-rad Trans-blot system (code no 170-3930). Afterwards, filter is blocked with PBS-0.05% Tween 20 overnight at room temperature, before incubation with the human sera. The following convalescent sera were tested: patients #262068, 261732, 262117, 261659, 261469, 261979, and 261324. These sera are diluted 100 times in PBS-0.05% Tween 20, and incubated on the nitrocellulose sheet for two hours at room temperature with gentle shaking, using a mini-blotter system (Miniprotean, Bio-rad code no 170-4017). After three repeated washing steps in PBS-0.05% Tween 20 for 5 min., the nitrocellulose sheet is incubated at room temperature for 1 hour under gentle shaking with the appropriate conjugate (biotinylated anti-human Ig antibodies, from sheep, Amersham code no RPN1003) diluted at 1/500 in the same washing buffer. The membrane is washed three times as previously, and incubated for 30 min with agitation using the streptavidin-peroxidase complex (Amersham code no 1051) diluted at 1/1000 in the washing buffer. After the last three repeated washing steps, the revelation occurs during the 20 min incubation time in a 50 ml solution containing 30 mg 4-chloro-1-naphtol (Sigma), 10 ml methanol, 40 ml of ultra-pure water, and 30 µl of $H_2O_2$. The staining is stopped while washing the membrane several times in distillated water. Results illustrated in FIGS. 6 and 7 show that all the 7 convalescents react against the major band of recombinant BASB041 protein at around 25-30 kDa. All of them react with around the same intensity, with slightly lower reactivity with patients 261979. In the right part of the western-blot, the reaction against the same 25-30 kD band is observed with the immunized mice sera, plus the band recognized at around 50 kDa.

Example 2

DNA Sequencing of the BASB043 Gene from Two *N. meningitidis* Strains.

A: BASB043 in *N. meningitidis* Serogroup B Strain ATCC13090.

The BASB043 gene of *N. meningitidis* strain ATCC 13090 is shown in SEQ ID NO:11. The translation of the BASB043 polynucleotide sequence, shown in SEQ ID NO:12, did not show any significant similarity to any known protein. The BASB043 polypeptide contains however a signal sequence characteristic of a lipoprotein, and could thus be inserted into the outer membrane of the bacterium.

The sequence of the BASB043 gene was further confirmed as follows. For this purpose, genomic DNA was extracted from $10^{10}$ cells of the *N. meningitidis* cells (strain ATCC 13090) using the QIAGEN genomic DNA extraction kit (Qiagen Gmbh), and 1 µg of this material was submitted to Polymerase Chain Reaction DNA amplification using primers lip7-01 (5'-ATG AAA AAA TAC CTT ATC CCT CTT TCC-3') [SEQ ID NO:13] and lip7-02 (5'-TCA TTT CAA GGG CTG CAT-3') [SEQ ID NO:14]. This PCR product was gel-purified and subjected to DNA sequencing using the Big Dye Cycle Sequencing kit (Perkin-Elmer) and an ABI 373A/PRISM DNA sequencer. DNA sequencing was performed on both strands with a redundancy of 2 and the full-length sequence was assembled using the SeqMan program from the DNASTAR Lasergene software package. The resulting DNA sequence turned out to be 100% identical to SEQ ID NO:11.

B: BASB043 in *N. meningitidis* Serogroup B Strain H44/76.

The sequence of the BASB043 gene was also determined in another *N. meningitidis* serogroup B strain, the strain H44/76. For this purpose, genomic DNA was extracted from the *N. meningitidis* strain H44/76 using the experimental conditions presented in the previous paragraph. This material (1 µg) was then submitted to Polymerase Chain Reaction DNA amplification using primers Lip7-01 and Lip7-02 specific for the BASB043 gene. The PCR amplicon was then submitted to DNA sequencing using the Big Dyes kit (Applied biosystems) and analyzed on a ABI 373/A DNA sequencer in the conditions described by the supplier. As a result, the polynucleotide sequence turned out to be 100% identical to SEQ ID NO:11.

Taken together, these data indicate strong sequence conservation of the BASB043 gene among the two *N. meningitidis* serogroup B strains.

Construction of Plasmid to Express Recombinant BASB043

A: Cloning of BASB043.

The NdeI and XhoI restriction sites engineered into the forward Lip7-Fm/p (5'-AGG CAG AGG CAT ATG AAA AAA TAC CTT ATC CCT CTT TCC ATT GCC-3') ([SEQ ID NO:15]) and reverse Lip7-RCf/p (5'-AGG CAG AGG CTC GAG TTT CAA GGG CTG CAT CTT CAT CAC TTC-3') ([SEQ ID NO:16]) amplification primers, respectively, permitted directional cloning of a BASB043 PCR product into the commercially available *E. coli* expression plasmid pET24b (Novagen, USA, kanamycin resistant) such that a mature BASB043 protein could be expressed as a fusion protein containing a (His)6 affinity chromatography tag at the C-terminus. The BASB043 PCR product was purified from the amplification reaction using silica gel-based spin columns (QiaGen) according to the manufacturers instructions. To produce the required NdeI and XhoI termini necessary for cloning, purified PCR product was sequentially digested to completion with NdeI and XhoI restriction enzymes as recommended by the manufacturer (Life Technologies). Following the first restriction digestion, the PCR product was purified via spin column as above to remove salts and eluted in sterile water prior to the second enzyme digestion. The digested DNA fragment was again purified using silica gel-based spin columns prior to ligation with the pET24b plasmid.

B: Production of Expression Vector.

To prepare the expression plasmid pET24b for ligation, it was similarly digested to completion with both NdeI and XhoI and then treated with calf intestinal phosphatase (CIP, ~0.02 units/pmole of 5' end, Life Technologies) as directed by the manufacturer to prevent self-ligation. An approximately 5-fold molar excess of the digested fragment to the prepared vector was used to program the ligation reaction. A standard ~20 μl ligation reaction (~16° C., ~16 hours), using methods well known in the art, was performed using T4 DNA ligase (~2.0 units/reaction, Life Technologies). An aliquot of the ligation (~5 μl) was used to transform electro-competent BL21 DE3 cells according to methods well known in the art. Following a ~2-3 hour outgrowth period at 37° C. in ~1.0 ml of LB broth, transformed cells were plated on LB agar plates containing kanamycin (50 μg/ml. The antibiotic was included in the selection media to ensure that all transformed cells carried the pET24b plasmid (KnR). Plates were incubated overnight at 37° C. for ~16 hours. Individual KnR colonies were picked with sterile toothpicks and used to "patch" inoculate fresh LB KnR plates as well as a ~1.0 ml LB KnR broth culture. Both the patch plates and the broth culture were incubated overnight at 37° C. in either a standard incubator (plates) or a shaking water bath.

A whole cell-based PCR analysis was employed to verify that transformants contained the BASB043 DNA insert. Here, the ~1.0 ml overnight LB Kn broth culture was transferred to a 1.5 ml polypropylene tube and the cells collected by centrifugation in a Beckman microcentrifuge (~3 min., room temperature, ~12,000×g). The cell pellet was suspended in ~200 μl of sterile water and a ~1011 aliquot used to program a ~50 μl final volume PCR reaction containing both BASB043 forward and reverse amplification primers. Final concentrations of the PCR reaction components were essentially the same as those specified in example 2 except ~5.0 units of Taq polymerase was used. The initial 95° C. denaturation step was increased to 3 minutes to ensure thermal disruption of the bacterial cells and liberation of plasmid DNA. An ABI Model 9700 thermal cycler and a 32 cycle, three-step thermal amplification profile, i.e. 95° C., 45 sec; 55-58° C., 45 sec, 72° C., 1 min., were used to amplify the BASB043 PCR fragment from the lysed transformant samples. Following thermal amplification, a ~20 μl aliquot of the reaction was analyzed by agarose gel electrophoresis (0.8% agarose in a Tris-acetate-EDTA (TAE) buffer). DNA fragments were visualized by UV illumination after gel electrophoresis and ethidium bromide staining. A DNA molecular size standard (1 Kb ladder, Life Technologies) was electrophoresed in parallel with the test samples and was used to estimate the size of the PCR products. Transformants that produced the expected PCR product were identified as strains containing a BASB043 expression construct. Expression plasmid containing strains were then analyzed for the inducible expression of recombinant BASB043.

C: Expression Analysis of PCR-Positive Transformants.

For each PCR-positive transformant identified above, ~5.0 ml of LB broth containing kanamycin (50 μg/ml) was inoculated with cells from the patch plate and grown overnight at 37° C. with shaking (~250 rpm). An aliquot of the overnight seed culture (~1.0 ml) was inoculated into a 125 ml erlenmeyer flask containing ~25 ml of LB Kn broth and grown at 37° C. with shaking (~250 rpm) until the culture turbidity reached O.D.600 of ~0.5, i.e. mid-log phase (usually about 1.5-2.0 hours). At this time approximately half of the culture (~12.5 ml) was transferred to a second 125 ml flask and expression of recombinant BASB043 protein induced by the addition of IPTG (1.0 M stock prepared in sterile water, Sigma) to a final concentration of 1.0 mM. Incubation of both the IPTG-induced and non-induced cultures continued for an additional ~4 hours at 37° C. with shaking. Samples (~1.0 ml) of both induced and non-induced cultures were removed after the induction period and the cells collected by centrifugation in a microcentrifuge at room temperature for ~3 minutes. Individual cell pellets were suspended in ~50 μl of sterile water, then mixed with an equal volume of 2× Laemelli SDS-PAGE sample buffer containing 2-mercaptoethanol, and placed in boiling water bath for ~3 min to denature protein. Equal volumes (~15 μl) of both the crude IPTG-induced and the non-induced cell lysates were loaded onto duplicate 12% Tris/glycine polyacrylamide gel (1 mm thick Mini-gels, Novex). The induced and non-induced lysate samples were electrophoresed together with prestained molecular weight markers (SeeBlue, Novex) under conventional conditions using a standard SDS/Tris/glycine running buffer (BioRad). Following electrophoresis, one gel was stained with commassie brilliant blue R250 (BioRad) and then destained to visualize novel BASB043 IPTG-inducible protein(s). The second gel was electroblotted onto a PVDF membrane (0.45 micron pore size, Novex) for ~2 hrs at 4° C. using a BioRad Mini-Protean II blotting apparatus and Towbin's methanol (20%) transfer buffer. Blocking of the membrane and antibody incubations were performed according to methods well known in the art. A monoclonal anti-RGS (His) antibody, followed by a second rabbit anti-mouse antibody conjugated to HRP (QiaGen), was used to confirm the expression and identity of the BASB043 recombinant protein. Visualization of the anti-His antibody reactive pattern was achieved using either an ABT insoluble substrate or using Hyperfilm with the Amersham ECL chemiluminescence system.

Production of Recombinant BASB043

Bacterial Strain

A recombinant expression strain of *E. coli* BL21 DE3 containing a pET24b plasmid encoding BASB043 from *N. meningitidis*. was used to produce cell mass for purification of recombinant protein. The expression strain was cultivated on LB agar plates containing 50 μg/ml kanamycin ("Kn") to ensure plasmid maintenance. For cryopreservation at −80° C., the strain was propagated in LB broth containing the same concentration of antibiotic then mixed with an equal volume of LB broth containing 30% (w/v) glycerol.

Media

The fermentation medium used for the production of recombinant protein consisted of 2×YT broth (Difco) containing 50 μg/ml Kn. Antifoam was added to medium for the fermentor at 0.25 ml/L (Antifoam 204, Sigma). To induce expression of the BASB043 recombinant protein, IPTG (Isopropyl β-D-Thiogalactopyranoside) was added to the fermentor (1 mM, final).

Fermentation

A 500-ml erlenmeyer seed flask, containing 50 ml working volume, was inoculated with 0.3 ml of rapidly thawed frozen culture, or several colonies from a selective agar plate culture, and incubated for approximately 12 hours at 37±1° C. on a shaking platform at 150 rpm (Innova 2100, New Brunswick Scientific). This seed culture was then used to inoculate a 5-L working volume fermentor containing 2×YT broth and both Kn antibiotic. The fermentor (Bioflo 3000, New Brunswick Scientific) was operated at 37±1° C., 0.2-0.4 VVM air sparge, 250 rpm in Rushton impellers. The pH was not controlled in either the flask seed culture or the fermentor. During fermentation, the pH ranged 6.5 to 7.3 in the fermentor. IPTG (1.0 M stock, prepared in sterile water) was added to the fermentor when the culture reached mid-log of growth (~0.7 O.D.600 units). Cells were induced for 2-4 hours then harvested by centrifugation using either a 28RS Heraeus (Sepatech) or RC5C superspeed centrifuge (Sorvall Instruments). Cell paste was stored at −20 C until processed.

Purification

Imidazole and biotechnology grade or better reagents were all obtained from Ameresco Chemical, Solon, Ohio. Triton X-100 (t-Octylphenoxypolyethoxy-ethanol), Triton X-114, sodium phosphate, monobasic, and urea were reagent grade or better and obtained from Sigma Chemical Company, St. Louis, Mo. Dulbecco's Phosphate Buffered XhoIne (1×PBS) was obtained from Quality Biological, Inc., Gaithersburg, Md. Dulbecco's Phosphate Buffered XhoIne (10×PBS) was obtained from BioWhittaker, Walkersville, Md. Penta-His Antibody, BSA free was obtained from QiaGen, Valencia, Calif. Peroxidase-conjugated AffiniPure Goat Anti-mouse IgG was obtained from Jackson Immuno Research, West Grove, Penn. All other chemicals were reagent grade or better.

Ni-chelatin Sepharose Fast Flow resin was obtained from Pharmacia, Sweden. Precast Tris-Glycine 4-20% and 10-20% polyacrylamide gels, all running buffers and solutions, SeeBlue Pre-Stained Standards, MultiMark Multi-Colored Standards and PVDF transfer membranes were obtained from Novex, San Diego, Calif. SDS-PAGE Silver Stain kits were obtained from Daiichi Pure Chemicals Company Limited, Tokyo, Japan. Coomassie Stain Solution was obtained from Bio-Rad Laboratories, Hercules, Calif. Acrodisc® PF 0.2 m syringe filters were obtained from Pall Gelman Sciences, Ann Arbor, Mich. GD/X 25 mm disposable syringe filters were obtained from Whatman Inc., Clifton, N.J. Dialysis tubing 8,000 MWCO was obtained from BioDesign Inc. Od New York, Carmal New York. BCA Protein Assay Reagents and Snake Skin dialysis tubing 3,500 MWCO were obtained from Pierce Chemical Co., Rockford, Ill.

Extraction Protocol

Cell paste was thawed at room temperature for 30 to 60 minutes. Five to six grams of material was weighed out into a 50-ml disposable centrifuge tube. Recombinant BASB043 antigen was purified by extraction of cell membranes with 25 mM Tris-HCl containing 4M guanidine-HCl. The supernatent was applied to nickel-chelating Sepharose Fast Flow. The protein is afterwards eluted with 200 mM imidazole to affinity purify the histidine-tagged protein and yielded greater than 90% pure protein.

Binding of BASB043 to Nickel Affinity Resin

After extraction, the mixture was incubated to the nickel-chelating Sepharose Fast Flow and placed at room temperature with gentle agitation for one hour. After one hour, the nickel-chelating Sepharose Fast Flow is packed into an XK16 Pharmacia column, and eluted afterwards with 200 mM imidazole buffer to affinity purify the histidine tagged protein and yielded greater than 90% pure protein. The fraction was dialyzed against PBS (pH7.4) containing 0.1% of Triton and stored at −70 at a concentration of 500 µg/ml.

Final Formulation

BASB043 was formulated by dialysis overnight against, three changes of 0.1% Triton X-100 and 1×PBS, pH 7.4. The purified protein was characterized and used to produce antibodies as described below.

Biochemical Characterizations: SDS-PAGE and Western Blot Analysis

The recombinant purified protein was resolved on 4-20% polyacrylamide gels and electrophoretically transferred to PVDF membranes at 100 V for 1 hour as previously described (Thebaine et al. 1979, Proc. Natl. Acad. Sci. USA 76:4350-4354). The PVDF membranes were then pretreated with 25 ml of Dulbecco's phosphate buffered XhoIne containing 5% non-fat dry milk. All subsequent incubations were carried out using this pretreatment buffer.

PVDF membranes were incubated with a dilution of anti-His tail antibodies for 1 hour at room temperature. PVDF membranes were then washed twice with wash buffer (20 mM Tris buffer, pH 7.5, containing 150 mM sodium chloride and 0.05% Tween-20). PVDF membranes were incubated with 25 ml of a 1:5000 dilution of peroxidase-labeled species specific conjugate for 30 minutes at room temperature. PVDF membranes were then washed 4 times with wash buffer, and were developed with 3-amino-9-ethylcarbazole and urea peroxide as supplied by Zymed (San Francisco, Calif.) for 10 minutes each.

Figure 8:
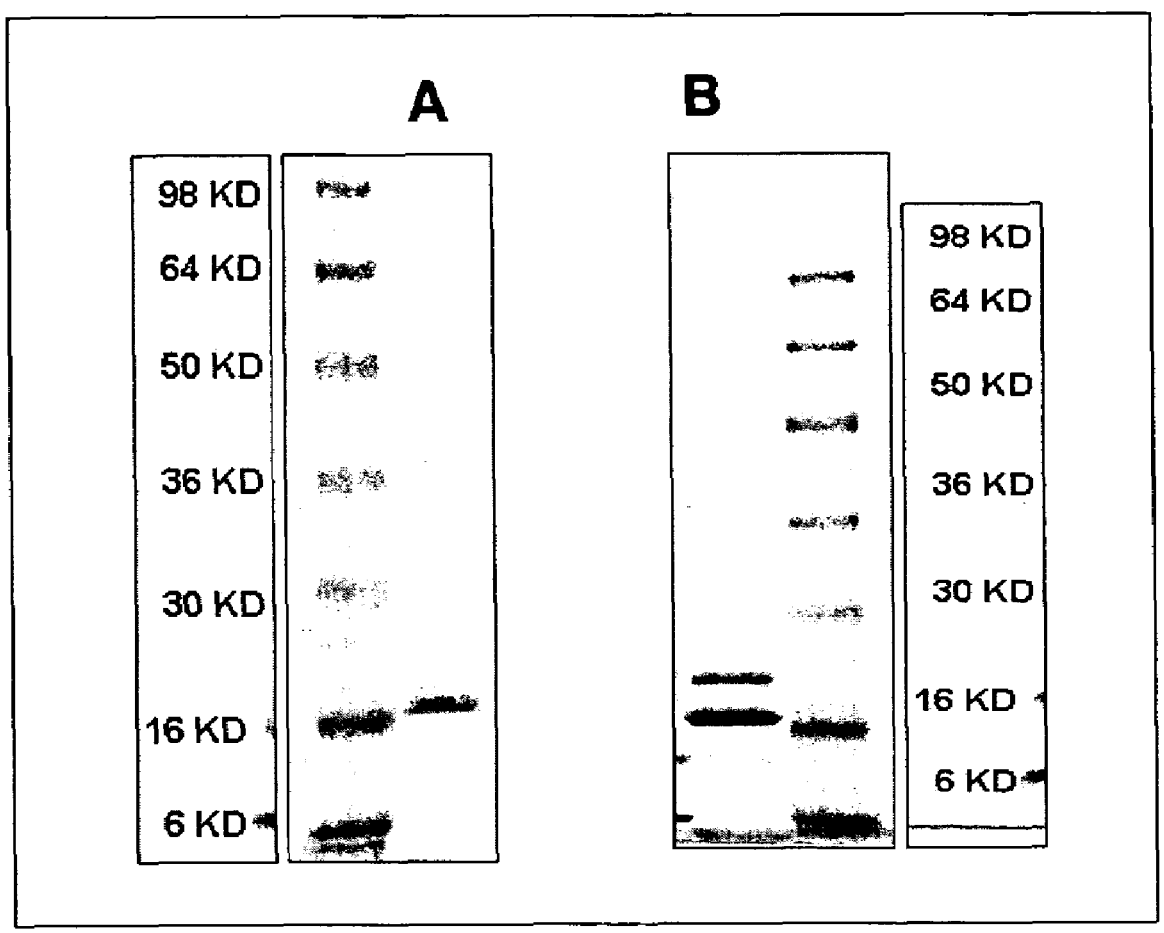
FIG. 8 is an electrophoretic analysis of purified BASB043 polypeptide (A. Coomassie stained SDS-polyacrylamide gel of BASB043./B. Immunodetection of the same gel using an anti-tetra-His immune response.

The results of an SDS-PAGE (FIG. 8) show a protein about 16 kDa purified to greater than 90% and that is reactive to an anti-RGS (His) antibody by western blots (FIG. 8) of the SDS-PAGE.

Immunization of Mice with Recombinant BASB043

Partially purified recombinant BASB043 protein expressed in *E. coli* has been injected three times in Balb/C mice on days 0, 14 and 28 (10 animals/group). Animals were injected by the subcutaneous route with around 5 µg of antigen in two different formulations: either adsorbed on 100 µg $AlPO_4$ or formulated in SBAS2 emulsion (SB62 emulsion containing 5 µg MPL and 5 µg QS21 per dose). A negative control group consisting of mice immunized with the SBAS2 emulsion only has also been added in the experiment. Mice were bled on days 28 (14 days Post II) and 35 (7 days Post III) in order to detect specific anti-BASB043 antibodies. Specific anti-BASB043 antibodies were measured by western-blotting on pooled sera (from 10 mice/group) from both formulations (on day 7 Post III only), using recombinant protein (part of the gel) and *Neisseria meningitidis* B strains.

Recognition of the BASB043 epitopes on different *Neisseria meningitidis* B strains by western-blotting In this test, immunized mice sera (pooled) have been tested by western-blotting for recognition of the BASB043 epitopes on seven different *Neisseria meningitidis* B strains: H44/76 (B:15:P1.7, 16, lineage ET-5), M97 250687 (B:4:P1.15), BZ10 (B:2b:P1.2, lineage A4), BZ198 (B:NT*: -, lineage 3), EG328 (B:NT*, lineage ST-18), NGP165 (B:2a:P1.2, ET 37 cluster) and the ATCC 13090 (B:15:P1.15) *Neisseria meningitidis* B strains, as well as on partially purified recombinant BASB043 protein. (*: NT: Not Typed).

Briefly, 10 µl (>$10^8$ cells/lane) of each sample treated with sample buffer (10 min at 95° C.) are put into a SDS-PAGE gradient gel (Tris-glycine 4-20%, Novex, code no EC60252). Electrophoretic migration occurs at 125 volts for 90 min. Afterwards, proteins are transferred to nitrocellulose sheet (0.45 µm, Bio-rad code no 162-0114) at 100 volts for 1 hour using a Bio-rad Trans-blot system (code no 170-3930). Filter was blocked with PBS-0.05% Tween 20 overnight at room temperature, before incubation with the mice sera containing the anti-BASB043 antibodies from both $AlPO_4$ and SBAS2 formulations. These sera are diluted 100 times in PBS-0.05% Tween 20, and incubated on the nitrocellulose sheet for two hours at room temperature with gentle shaking, using a mini-blotter system (Miniprotean, Bio-rad code no 170-4017). After three repeated washing steps in PBS-0.05% Tween 20 for 5 min., the nitrocellulose sheet is incubated at room temperature for 1 hour under gentle shaking with the appropriate conjugate (biotinylated anti-mouse Ig antibodies from sheep, Amersham code no RPN1001) diluted at 1/500 in the same washing buffer. The membrane is washed three times as previously, and incubated for 30 min with agitation using the streptavidin-peroxidase complex (Amersham code no 1051) diluted at 1/1000 in the washing buffer. After the last three repeated washing steps, the revelation occurs during the 20 min incubation time in a 50 ml solution containing 30 mg 4-chloro-1-naphtol (Sigma), 10 ml methanol, 40 ml PBS, and 30 µl of $H_2O_2$. The staining is stopped while washing the membrane several times in distilled water.

Figure 9:
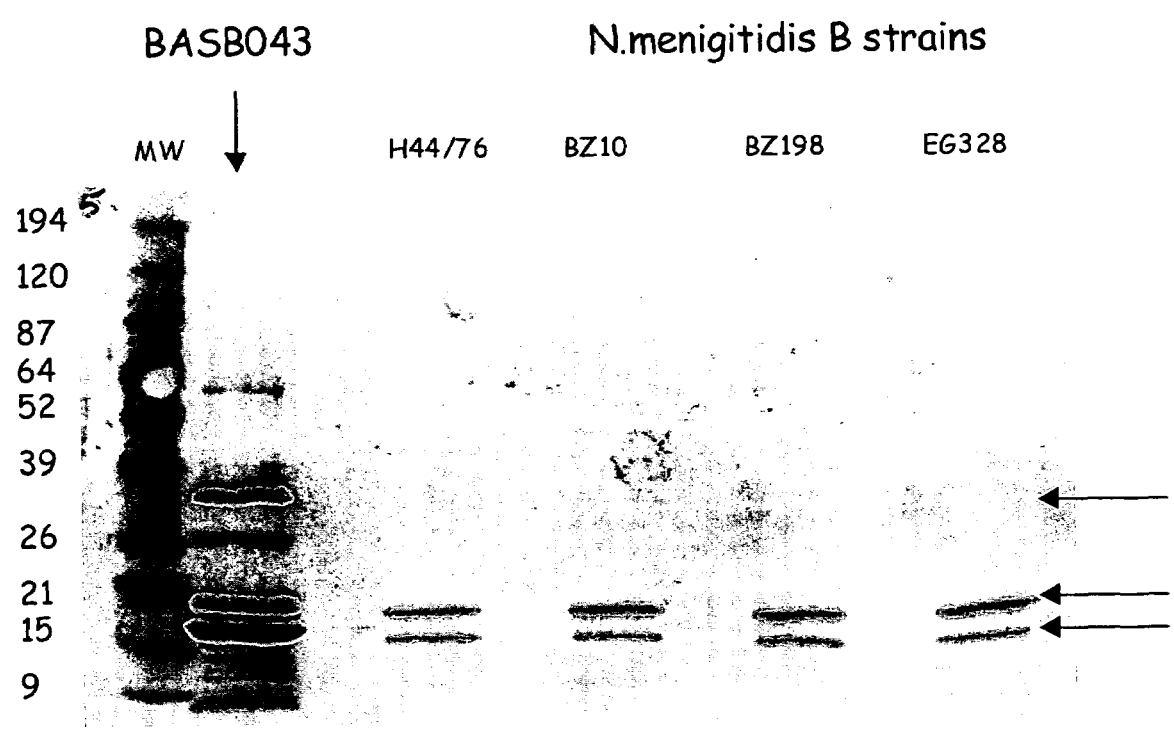
FIG. 9 shows a Western blot for recognition of BASB043 protein in several *Neisseria meningitidis* strains with BASB043 immunized mice sera.
Figure 10:
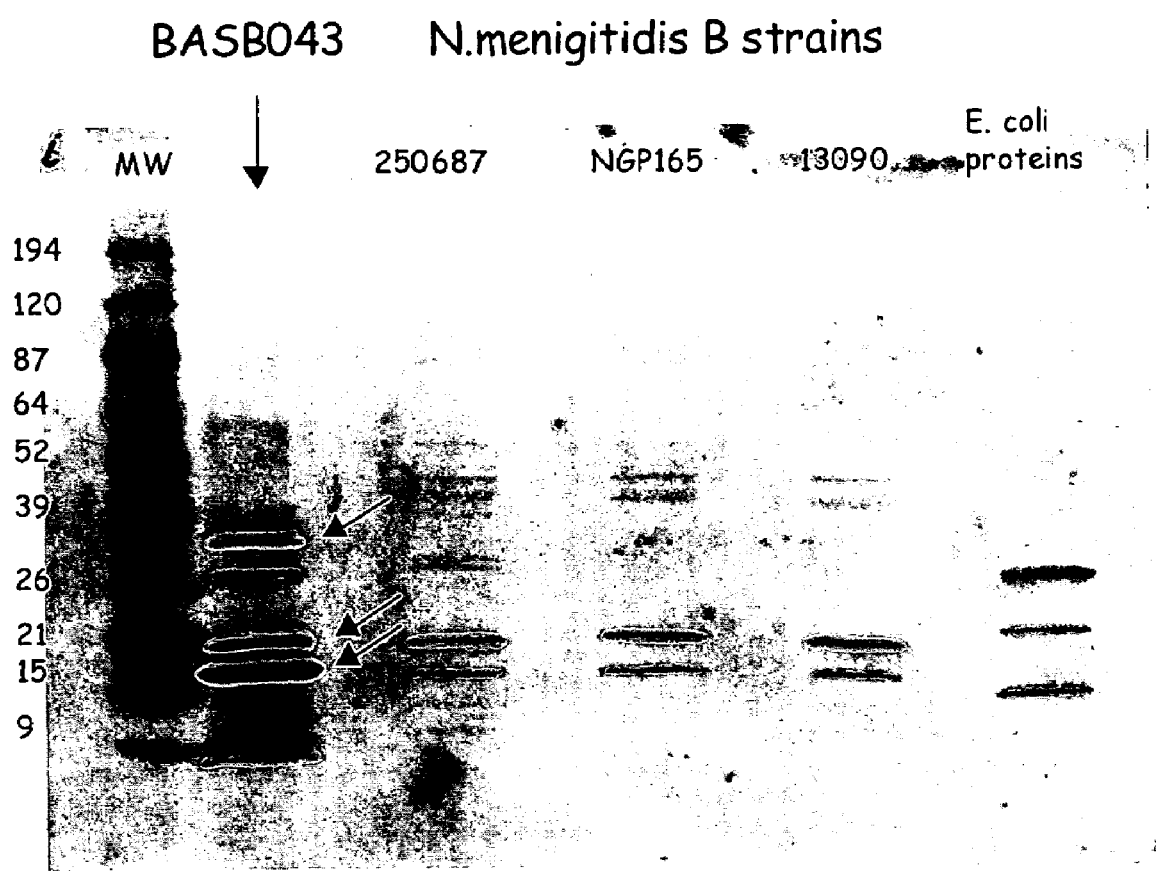
FIG. 10 shows a Western blot for recognization of BASB043 protein in several *Neisseria meningitidis* strains with BASB043 immunized mice sera.

Results illustrated in FIGS. 9 and 10 show that all strains tested present the expected bands around 20 kDa (major), 25 and 35-40 kDa (minors), which are recognized at the same level in all of the *Neisseria meningitidis* B strains tested. This means that the BASB043 protein is expressed in probably all *Neisseria meningitidis* B strains. In both figures, the recombinant BASB043 protein is also clearly recognized by mice sera at the same MW (second lane after the MW). This BASB043 protein is not recognized anymore on *E. coli* preparation.

Presence of Anti-BASB043 Antibodies in Sera from Convalescent Patients.

In this test, several convalescent sera have been tested by western-blotting for recognition of the purified recombinant BASB043 protein.

Briefly, 5 µg of partially purified BASB043 *Neisseria meningitidis* B protein are put into a SDS-PAGE gradient gel (4-20%, Novex, code no EC60252) for electrophoretic migration. Proteins are transferred to nitrocellulose sheet (0.45 µm, Bio-rad code no 162-0114) at 100 volts for 1 hour using a Bio-rad Trans-blot system (code no 170-3930). Afterwards, filter is blocked with PBS-0.05% Tween 20 overnight at room temperature, before incubation with the human sera. The following convalescent sera were tested: patients #261469, 261979, 261324, 261732, 262117 and 261659. These sera are diluted 100 times in PBS-0.05% Tween 20, and incubated on the nitrocellulose sheet for two hours at room temperature with gentle shaking, using a mini-blotter system (Miniprotean, Bio-rad code no 170-4017). After three repeated washing steps in PBS-0.05% Tween 20 for 5 min., the nitrocellulose sheet is incubated at room temperature for 1 hour under gentle shaking with the appropriate conjugate (biotinylated anti-human Ig antibodies, from sheep, Amersham code no RPN1003) diluted at 1/500 in the same washing buffer. The membrane is washed three times as previously, and incubated for 30 min with agitation using the streptavidin-peroxidase complex (Amersham code no 1051) diluted at 1/1000 in the washing buffer. After the last three repeated washing steps, the revelation occurs during the 20 min incubation time in a 50 ml solution containing 30 mg 4-chloro-1-naphtol (Sigma), 10 ml methanol, 40 ml of ultra-pure water, and 30 µl of $H_2O_2$. The staining is stopped while washing the membrane several times in distilled water.

Figure 11:
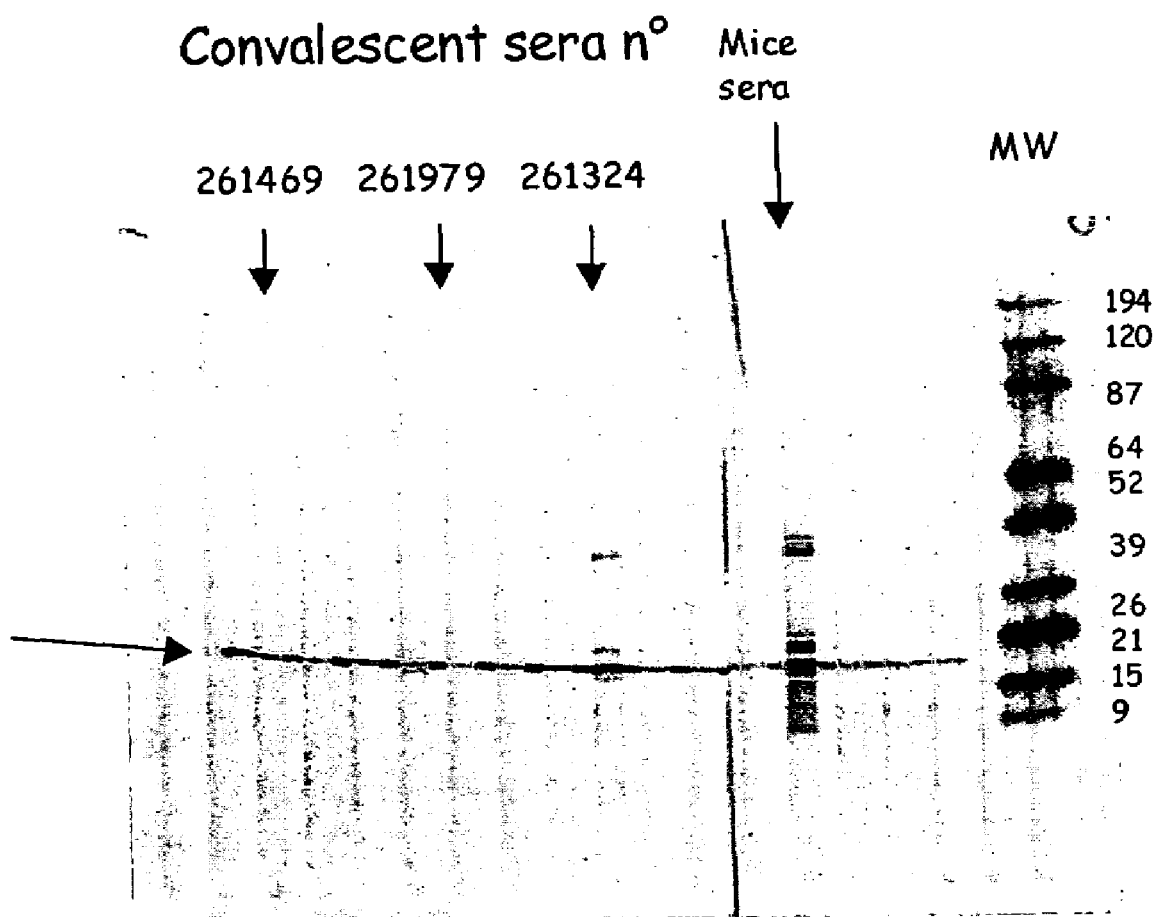
FIG. 11 shows a Western blot for recognition of BASB043 protein in convalescent sera and immunized mice.
Figure 12:
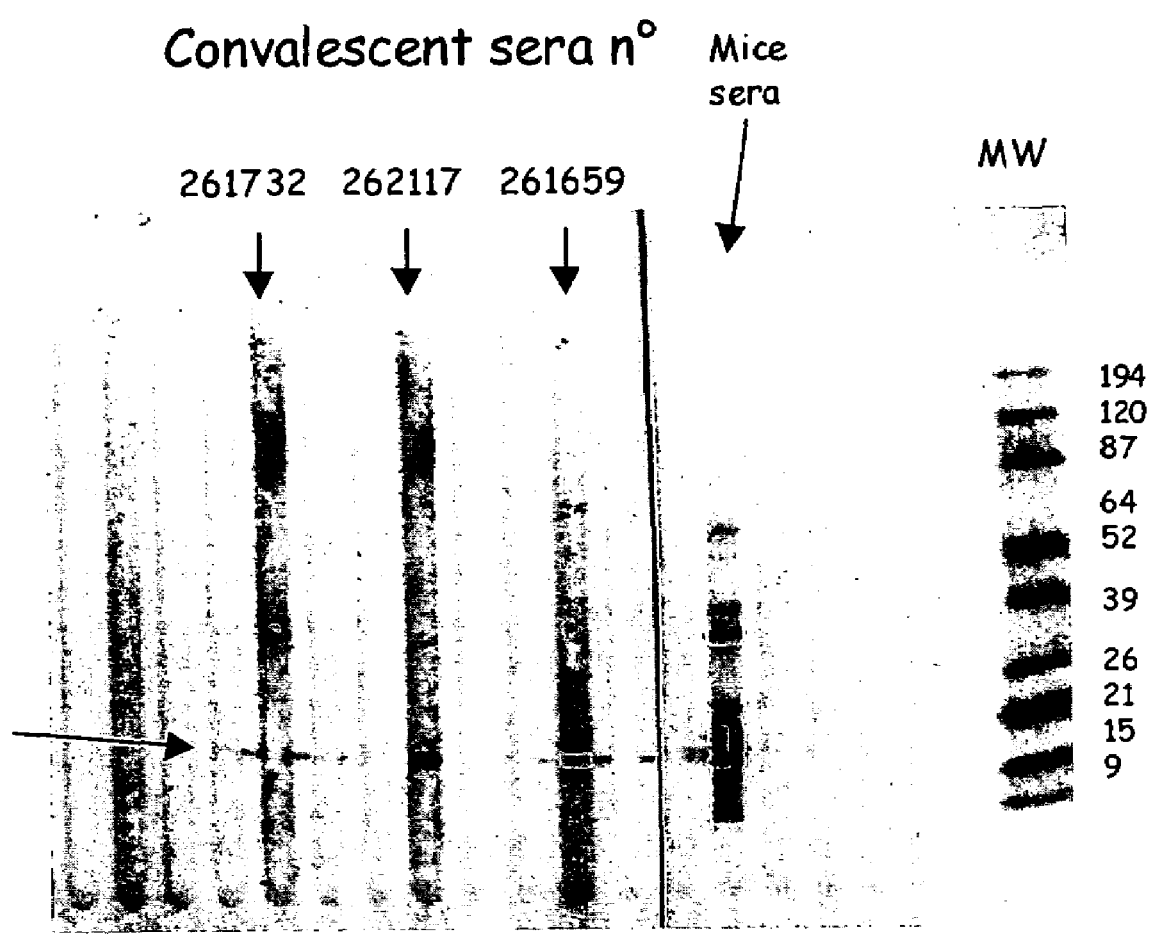
FIG. 12 shows a Western blot for recognition of BASB043 protein in convalescent sera and immunized mice.

Results illustrated in FIGS. 11 and 12 show that all the 6 convalescents react against the major band of recombinant BASB043 protein at around 20 kDa. Human sera recognize only this band while mice sera recognize the three major bands of BASB043. All of these human convalescent react with a very high intensity, except for convalescent no 262117 who shows a lower reactivity. In the right part of the western-blot, the reaction against the same 25-30 kD band is observed with the immunized mice sera, plus the band recognized at around 50 kDa. Few bands at a lower MW are also observed. Few leaks also are visible in FIG. 11.

Example 3

DNA Sequencing of the BASB044 Gene from Two *N. meningitidis* Strains.

A: BASB044 in *N. meningitidis* serogroup B strain ATCC13090.

The BASB044 gene of *N. meningitidis* strain ATCC 13090 is shown in SEQ ID NO:17. The translation of the BASB044 polynucleotide sequence, shown in SEQ ID NO:18, shows significant similarity (25% identity in a 425 residues overlap) to the *E. coli* long chain fatty acid transport protein FadL.

The sequence of the BASB044 gene was further confirmed as follows. For this purpose, genomic DNA was extracted from $10^{10}$ cells of the *N. meningitidis* cells (strain ATCC 13090) using the QIAGEN genomic DNA extraction kit (Qiagen Gmbh), and 1 µg of this material was submitted to Polymerase Chain Reaction DNA amplification using primers Fadl-17 (5' TGA GTG GAA AAT GCC GTC TGA AGT-3') [SEQ ID NO:21] and Fadl-18 (5' TGC ACC CCG TCA TTC CTG TCT-3') [SEQ ID NO:22]. This PCR product was gel-purified and subjected to DNA sequencing using the Big Dye Cycle Sequencing kit (Perkin-Elmer) and an ABI 373A/PRISM DNA sequencer. DNA sequencing was performed on both strands with a redundancy of 2 and the full-length sequence was assembled using the SeqMan program from the DNASTAR Lasergene software package. The resulting DNA sequence turned out to be 100% identical to SEQ ID NO:17.

B: BASB044 in *N. meningitidis* Serogroup B Strain H44/76.

The sequence of the BASB044 gene was also determined in another *N. meningitidis* serogroup B strain, the strain H44/76. For this purpose, genomic DNA was extracted from the *N. meningitidis* strain H44/76 using the experimental conditions presented in the previous paragraph. This material (1 µg) was then submitted to Polymerase Chain Reaction DNA amplification using primers Fadl-01 (5' CAT AGC ACC ATG GCC GGC TAC CAC TTC G-3') [SEQ ID NO:23] and Fadl-02 (5' CTA GTC TAG ATT ATT TGA ATT TGT AGG TGT AT-3') [SEQ ID NO:24] specific for that part of the BASB044 gene which encodes the mature protein, assuming that the mature protein would start at amino acid number 25 of SEQ ID NO:18. The PCR amplicon was then submitted to DNA sequencing using the Big Dyes kit (Applied biosystems) and analyzed on a ABI 373/A DNA sequencer in the conditions described by the supplier. As a result, the polynucleotide and deduced polypeptide sequences, referred to as SEQ ID NO:19 and SEQ ID NO:20 respectively, were obtained. Using the MegAlign program in the DNASTAR Lasergene package, an alignment of the polynucleotide sequences of SEQ ID NO:17 and 19 was performed, and is displayed in FIG. 13; their level of identity amounts to 99.6%. Using the same MegAlign program, an alignment of the polypeptide sequences of SEQ ID NO:18 and 20 was performed, and is displayed in FIG. 14; their level of identity amounts to 99.8%.

Taken together, these data indicate strong sequence conservation of the BASB044 gene among the two *N. meningitidis* serogroup B strains.

Example 4

The BASB048 Gene in *N. meningtidis* Strain ATCC 13090.

The BASB048 gene of *N. meningitidis* strain ATCC 13090 is shown in SEQ ID NO:25. The translation of the BASB048 polynucleotide sequence, shown in SEQ ID NO:26, shows significant similarity (27% identity in a 429 residues overlap) to a *Serratia marcescens* ABC exporter outer membrane component, as well as to other members of the TolC protein family. The BASB048 polypeptide contains a leader signal sequence, as predicted by the program Spscan of the GCG software package.

The predicted signal sequence would be cleaved after residue Ala58. BASB048 is then either a membrane protein, a surface protein or a secreted protein.

| Polynucleotide and Polypeptide Sequences |
|---|
| SEQ ID NO:1<br>*Neisseria meningitidis* BASB041 polynucleotide sequence from strain ATCC 13090<br><br>ATGAAAACCGTTTCCACCGCCGTTGTCCTTGCCGCCGCTGCCGTTTCACTGACCGGCTGTGCGACCGAATCCTCACGCAG<br><br>TCTCGAGGTAGAGAAAGTCGCCTCCTACAATACGCAATACCACGGCGTGCGTACCCCGATTTCCGTCGGAACATTCGACA<br><br>ACCGCTCCAGCTTCCAAAAAGGCATTTTCTCCGACGGGGAAGACCGTTTGGGCAGCCAGGCAAAAACCATTCTGGTAACG<br><br>CACCTGCAACAGACCAACCGCTTCAACGTACTGAACCGCACCAATTTGAACGCATTAAAACAGGAATCCGGCATTTCCGG<br><br>CAAAGCGCATAACCTGAAAGGCGCAGATTATGTCGTTACTGGCGATGTAACCGAATTCGGACGCAGAGATGTCGGCGATC<br><br>ATCAGCTCTTCGGCATTTTGGGTCGCGGCAAATCGCAAATCGCCTATGCAAAAGTGGCTCTGAATATCGTCAACGTCAAT<br><br>ACTTCCGAAATCGTCTATTCCGCACAGGGCGCGGGCGAATACGCACTTTCCAACCGTGAAATCATCGGTTTCGGCGGCAC<br><br>TTCCGGCTACGATGCGACTTTGAACGGCAAAGTTTTAGACTTGGCAATCCGCGAACCGTCAACAGCCTGGTTCAGGCTGT<br><br>TGACAACGGCGCATGGCAACCCAACCGTTAA<br><br>SEQ ID NO:2<br>*Neisseria meningitidis* BASB041 polypeptide sequence deduced from the polynucleotide sequence of SEQ 1ID NO: 1<br><br>MKTVSTAVVLAAAAVSLTGCATESSRSLEVEKVASYNTQYHGVRTPISVGTFDNRSSFQKGIFSDGEDRLGSQAKTILVT<br><br>HLQQTNRFNLNRTNINALKQESGISGKAHNLKGADYVVTGDVTEFGRRLVGDHQLFGILGRGKSQIAYAKVALNIVNVN<br><br>TSEIVYSAQGAGEYALSNREIIGFGGTSGYDATLNGKVLDLAIREPSTAWFRLLTTAHGNPTV<br><br>SEQ ID NO:3<br><br>*Neisseria meningitidis* BASB041 polynucleotide sequence from strain ATCC 13090<br><br>ATGAAAACCGTTTCCACCGCCGTTGTCCTTGCCGCCGCTGCCGTTTCACTGACCGGCTGTGCGACCGAATCCTCACGCAG<br><br>TCTCGAGGTAGAGAAAGTCGCCTCCTACAATACGCAATACCACGGCGTGCGTACCCCGATTTCCGTCGGAACATTCGACA<br><br>ACCGCTCCAGCTTCCAAAAAGGCATTTTCTCCGACGGGGAAGACCGTTTGGGCAGCCAGGCAAAAACCATTCTGGTAACG<br><br>CACCTGCAACAGACCAACCGCTTCAACGTACTGAACCGCACCAATTTGAACGCATTAAAACAGGAATCCGGCATTTCCGG |

| Polynucleotide and Polypeptide Sequences |
| --- |

CAAAGCGCATAACCTGAAAGGCGCAGATTATGTCGTTACTGGCGATGTAACCGAATTCGGACGCAGAGATGTCGGCGAT

C

ATCAGCTCTTCGGCATTTTGGGTCGCGGCAAATCGCAAATCGCCTATGCAAAAGTGGCTCTGAATATCGTCAACGTCAA

T

ACTTCCGAAATCGTCTATTCCGCACAGGGCGCGGGCGAATACGCACTTTCCAACCGTGAAATCATCGGTTTCGGCGGCA

C

TTCCGGCTACGATGCGACTTTGAACGGCAAAGTTTTAGACTTGGCAATCCGCGAAGCCGTCAACAGCCTGGTTCAGGCT

G

TTCACAACGGCGCATGGCAACCCAACCGTTAA

SEQ ID NO:4
*Neisseria meningitidis* BASB041 polypeptide sequence deduced from the polynucleotide sequence of SEQ ID NO:3

MKTVSTAVVLAAAAVSLTGCATESSRSLEVEKVASYNTQYHGVRTPISVGTEDNRSSFQKGIFSDGEDRLGSQAKTILV

T

HLQQTNRFNVLNRTNINALKQESGISGKAHNLKGADYVTGDVTEFGRRDVGDHQLFGILGRGKSQIAYAKVALNIVNV

N

TSEIVYSAQGAGEYALSNREIIGFGGTSGYDATLNGKVLDLAIREAVNSLVQAVDNGAWQPNR

SEQ ID NO:5
*Neisseria meningitidis* BASB041 polynucleotide sequence from strain H44/76

ATGAAAACCGTTTCCACCGCCGTTGTCCTTGCCGCCGCTGCCGTTTCACTGACCGGCTGTGCGACCGAATCCTCACGCA

G

TCTCGAGGTAGAGAAGTCGCCTCCTACAATACGCAATATCACGGTGTTCGTACCCCGATTTCCGTCGGAACATTCGAC

A

ACCGCTCCAGCTTCCAAAAAGGCATTTTCTCCGACGGGGAAGACCGTTTGGGCAGCCAGGCAAAAACCATTCTAGTAAC

G

CACCTGCAACAGACCAACCGCTTCAACGTACTGAACCGCACCAATTTGAACGCATTAAAACAGGAATCCGGCATTTCCG

G

CAAAGCGCATAACCTGAAGGCGCAGATTATGTCGTTACCGGCGATGTAACCGAATTCGGACGCAGAGATGTCGGCGAT

C

ATCAGCTCTTCGGCATTTTGGGTCGCGGCAAATCGCATCGCCTATGCAAGTGGCTCTGAATATCGTCAACGTCAA

T

ACTTCCGAATCGTCTATTCCGCACAGGCGCGGCGAATACGCACTTTCCACCGTGAAATCATCGGTTTCGGCGGCA

C

TTCCGGCTACGATGCGACTTTGAACGGCAAAGTTTTAGACTTGGCAATCCGCGAAGCCGTCAACAGCCTGGTTCAGGCT
G

TTGACAACGGCGCATGGCAACCCAACCGTTAA

SEQ ID NO:6
*Neisseria meningitidis* BASB041 polypeptide sequence deduced from the polynucleotide sequence of SEQ ID NO:5

MKTVSTAVVLAAAAVSLTGCATESSRSLEVEKVASYNTQYHGVRTPISVGTFDNRSSFQKGIFSDGEDRLGSQAXTILV

T

-continued

| Polynucleotide and Polypeptide Sequences |
|---|
| HLQQTNRFNVLNRTNLNALKQESGISGKAHNLKGADYVVTGDVTEFGRRDVGDHQLFGILGRGKSQIAYAKVALNIVNV |
| N |
| TSEIVYSAQGAGEYALSNREIIGFGGTSGYDATLNGKVLDLAIREAVNSLVQAVDNGAWQPNR |
| SEQ ID NO:7 |
| AAT GAA AAC CGT TTC CAC CGC |
| SEQ ID NO:8 |
| TCA TTT CTC CTT AAC GGT |
| SEQ ID NO:9 |
| AGG CAG AGG CAT ATG AAA ACC GTT TCC ACC GCC GTT GTC CTT GC |
| SEQ ID NO:10 |
| AGG CAG AGG GTC GAC TTT CTC CTT AAC GGT TGG GTT GCC ATG CGC |
| SEQ ID NO:11 |
| *Neisseria meningitidis* BASB043 polynucleotide sequence from strain ATCC 13090 |
| ATGAAAAAATACCTTATCCCTCTTTCCATTGCGGCAGTTCTTTCCGGCTGCCAGTCTATTTATGTGCCCACATTGACGG |
| A |
| AATCCCCGTGAATCCTATCAATACCGTCAAAACGGAAGCACCTGCAAAAGGTTTCCGCCTTGCCTCTTCGCATTGGACG |
| G |
| ATGTTGCCAAAATCAGCGATGAAGCGACGCGCTTGGGCTATCAGGTGGGTATCGGTAAAATGACCAAGGTTCAGGCGGC |
| G |
| CAATATCTGAACAACTTCAGAAAACGCCTGGTCGGACGCAATGCCGTCGATGACAGTATGTATGAAATCTACCTGCGTT |
| C |
| GGCCATAGACAGCCAGCGGGGCGCAATCAATACGGAACAGTCCAAGCTGTATATCCAGAATGCCTTGCGCGGCTGGCAG |
| C |
| AGCGTTGGAAAAATATGGATGTCAAACCCAACAACCCCGCATTTACCAACTTTTTGATGGAAGTGATGAAGATGCAGCC |
| C |
| TTGAAATGA |
| SEQ ID NO:12<br>*Neisseria meningitidis* BASB043 polypeptide sequence deduced from the polynucleotide sequence of SEQ ID NO: 11 |
| MKKYLIPLSIAAVLSGCQSIYVPTLTEIPVNPINTVKTEAPAKGFRLASSHWTDVAKISDEATRLGYQVGIGKMTKVQA |
| A |
| QYLNNFRKRLVGRNAVDDSMYEIYLRSAIDSQRGAINTEQSKLYIQNALRGWQQRWKINLDVKPNNPAFTNFLMEVMKMQ |
| P |
| LK |
| SEQ ID NO:13 |
| ATG AAA AAA TAC CTT ATC CCT CTT TCC |
| SEQ ID NO:14 |
| TCA TTT CAA GGG CTG CAT |
| SEQ ID NO:15 |
| AGG CAG AGG CAT ATG AAA AAA TAC CTT ATC CCT CTT TCC ATT GCC |

-continued

Polynucleotide and Polypeptide Sequences

SEQ ID NO:16

AGG CAG AGG CTC GAG TTT CAA GGG CTG CAT CTT CAT CAC TTC

SEQ ID NO:17
*Neisseria meningitidis* BASB044 polynucleotide sequence from strain ATCC 13090

ATGACCCCTTCCGCACTGAAAAAAACCGTCCTGCTGCTCGGCACTGCCTTTGCCGCCGCATCCGCACAAGCCTCCGGCT

A

CCACTTCGGCACACAGTCGGTCAACGCGCAAAGCACGGCAAATGCCGCCGCCGCAGAAGCCGCCGACGCATCGACCATC

T

TCTACAACCCTGCCGGCCTGACCAAACTCGACAGCAGCCAGATTTCCGTCAACGCCAACATCGTGCTGCCCAGCATTCA

T

TATGACGCCGATTCCGCCACCGACTTTACCGGGCTTCCCGTCCAAGGTTCGAAAAGCGGCAAAATCACCAAAACCACGG

T

CGCGCCCCACATCTACGGCGCATACAAAGTCAACGACAATCTGACCGTACGCTTGGGCGTGTACGTCCCCTTCGGTTCT

G

CCACCGAATACGAAAAAGATTCCGTGTTGCGCCACAACATCAACAAACTCGGTCTGACCAGCATCGCCGTCGAACCTGT

C

GCCGCGTGGAAACTCAACGACCCCCATTCCTTCGGCGCAGGCATCATCGCCCAACATACTTCCGCCGAACTGCGCAAAT

A

TGCCGACTGGGGGATTAAGAGTAAAGCAGAGATATTGACGGCAAAACCGCCCAAACCTAACGGTGTAGCCGAAGCTGCA

A

AAATTCAGGCCGACGGACACGCCGATGTCAAAGGCAGCGATTGGGGCTTCGGCTACCAACTGGCGTGGATGTGGACAT

C

AACGACCGTGCGCGCGTGGGCGTGAACTACCGTTCCAAAGTCTCGCACACGCTCAAACGCGATGCCGAATGGGCGGCAG

A

CGGCGCGGCGGCGAAAGCAATGTGGAGTACGATGCTTGCAGCAAACGGCTACACGGCGAATGAAAAAGCCCGCGTTAAA

A

TCGTTACGCCTGAGTCTTTGTCCGTACACGGTATGTACAAAGTGTCCGATAAAGCCGACCTGTTCGGCCACGTAACTTG
C

ACGCGCCACAGCCGCTTCGATAAGGCGGAACTGGTTTTTGAAAAAGAAAAAACCGTCGTCAAAGGCAAATCCGACCGCA

C

CACCATCACCCCCAACTGGCGCAACACCTACAAAGTCGGCTTCGGCGGTTCTTATCAAATCAGCGAACCGCTGCAACTG

C

GCGCCGGCATCGCTTTTGACAAATCGCCCGTCCGCAACGCCGACTACCGCATGAACAGCCTGCCCCACGGCAACCGCAT

C

TCGTTCTCCGCCGGTATCAAATACCATATCGGTAAAAACCACGTCGTCGATGCCGCCTACACCCACATCCACATCAACG

A

CACCACCTACCGCACGGCGAAGGCAAGCGGCAACGATGTGGACAGCAAAGGCGCGTCTTCCGCACGTTTCAAAAACCAC

G

CCCACATCATCGGCCTGCAATACACCTACAAATTCAAATAA

-continued

Polynucleotide and Polypeptide Sequences

SEQ ID NO:18
*Neisseria meningitidis* BASB044 polypeptide sequence deduced from the polynucleotide sequence of SEQ ID NO: 17

MTPSALKKTVLLLGTAFAAASAQASGYHFGTQSVNAQSTANAAAAEAADASTIFYNPAGLTKLDSSQISVNANIVLPSI

H

YEADSATDFTGLPVQGSKSGKITKTTVAPHIYGAYKVNDNLTVGLCVYVPFGSATEYEKDSVLRHNINKLGLTSIAVEP

V

AAWKLNDRHSFGAGIIAQHTSAELRKYADWGIKSKAEILTAXPPKPNGVAEAAKIQADGHADVKGSDWGFGYQLAWMWD

I

NDRARVGVNYRSKVSHTLKGDAEWAADGAAAKAMWSTMLAANGYTANEKARVKIVTPESLSVHGMYKVSDKADLFGDVT

W

TRHSRFDKAELVFEKEKTVVVKGKSDRTTITPNWRNTYKVGFGGSYQISEPLQLRAGIAFDKSPVRNADYRMNSLPDGNR

I

WFSAGMKYHICKNHVVDAAYTHIHINDTTYRTAKASGNDVDSKGASSARFKNHADIIGLQYTYKFK

SEQ ID NO:19
*Neisseria meningitidis* BASB044 polynucleotide sequence from strain H44/76

TCCGCCTACCACTTCGGCACACAGTCGGTCAACGCGCAAAGCACGGCAAATGCCGCCGCCGCAGAAGCCGCCGACGCAT

C

GACCATCTTCTACAACCCTGCCGGCCTGACCAAACTCCACAGCAGCCAGATTTCCGTCAACGCCAACATCGTGCTGCCC

A

GCATTCATTATGAGGCGGATTCCGCCACCGACTTTACCGGGCTTCCCGTCCAAGGTTCGAAAAGCGGCAAAATCACCAA

A

ACCACGGTCGCGCCCCACATCTACGGCGCATACAAAGTCAACGACAATCTGACCGTGGGCTTGGGCOTGTACGTCCCCT

T

CGGCTCTGCCACCGAATACGAAAAAGATTCCGTGTPGCGCCACAACATCAACAAACTCGGTCTGACCAGCATCGCCGTC

G

AACCTGTCGCCGCGTGGAACTCAACGACCGCCATTCCTTCGGCGCAGGCATCATCGCCCAACATACTTCCGCCGAACT

G

CGCAAATATGCCGACTGGGGGATTAAGAGTAAAGCAGAGATATTGACGGCAAAACCGCCCAAACCTAACGGTGTAGCCG

A

AGCTGCAAAAATTCAGGCCGACGGACACGCCGATGTCAAAGGCAGCGATTGGGGCTTCCCCTACCAACTGGCGTGGATG

T

GGGACATCAACGACCGTGCGCGCGTGCGCGTGAACTACCGTTCCAAAGTCTCGCACACGCTCAAAGOCGATGCCGAATG

G

GCGGCAGACGGCGCGGCGGCGAAAGCAATGTGGAGTACGATGCTTGCAGCAAACGGCTACACGGCGAATGAAAAAGCCC

G

CGTTAAAATCGTTACGCCTGAGTCTTTGTCCGTACACGGTATGTACAAAGTGTCCGATAAAGCCGACCTGTTCGGCGAC

C

TAACTTGGACGCGCCACAGCCGCTTCGATAACGCGGAACTGGTTTTTGAAAAAGA~AAACCGTCGTCAAAGGCAAATC

C

| Polynucleotide and Polypeptide Sequences |
|---|
| GACCGCACCACCATCACCCCCAACTGGCGCAACACCTACAAAGTCGGCTTCGGCGGTTCTTATCAAATCAGCGAACCGCT |
| CCAACTGCGCCCCCGCATCGCTTTTGACAAATCGCCCGTCCGCAACGCCCACTACCGCATGAACAGCCTACCCGACGGCA |
| ACCGCATCTGGTTCTCCGCCGGTATGAAATACCATATCCGTAAAAACCACGTCGTCGATGCCCCCTACACCCACATCCAC |
| ATCAACGACACCAGCTACCGCACGGCGAAGGCAAGCGGCAACGATGTGGACAGCAAAGCCGCGTCTTCCGCACGTTTCAA |
| AAACCACGCCGACATCATCGGTCTGCAATACACCTACAAATTCAAATAA |
| SEQ ID NO:20<br>*Neisseria meningitidis* BASB044 polypeptide sequence deduced from the polynucleotide sequence of SEQ ID NO: 19 |
| SGYHFGTQSVNAQSTANAAAAEAADASTIFYNPAGLTKLDSSQISVNANIVLPSIHYEADSATDFTGLPVQGSKSGKITK |
| TTVAPHYGAYKVNDNLTVGLGVYVPFGSATEYEKDSVLRHNINKLGLTSIAVEPVAAWXLNDRHSFGAGIIAQHTSAEL |
| RKYADWGIKSKAEILTAXPPKPNGVAEAAKIQADGHADVKGSDWGFGYQLAWMWDTNDRARVGVNYRSKVSHTLKGDAEW |
| AADGAAAXAMWSTANGYTANEKARVKIVTPESLSVHGMYKVSDKADLFGDVTWTRHSRFDKAELVFEXEXTVVKGKS |
| DRTTITPNWRNTYKVGFGGSYQISEPLQLRAGIAFDKSPVRNADYRMNSLPDGNRIWFSAGMKYHIGKNHVVDAAYTHIH |
| INDTSYRTAKASGNDVDSKGASSARFKNHADIIGLQYTYKFK |
| SEQ ID NO:21 |
| TGA GTG GAA AAT GCC GTC TGA AGT |
| SEQ ID NO:22 |
| TGC ACC CCG TCA TTC CTG TCT |
| SEQ ID NO:23 |
| CAT AGC ACC ATG GCC GGC TAC CAC TTC G |
| SEQ ID NO:24 |
| CTA GTC TAG ATT ATT TGA ATT TGT AGG TGT AT |
| SEQ ID NO:25<br>*Neisseria meningitidis* BASB048 polynucleotide sequence from strain ATCC 13090 |
| ATGACATTGCTCAATCTAATGATAATGCAAGATTACGGTATTTCCGTTTGCCTGACACTG |
| ACGCCCTATTTGCAACATGAACTATTTTCGGCTATGAAATCCTATTTTTCCAAATATATC |
| CTACCCGTTTCACTTTTTACCTTGCCACTATCCCTTTCCCCATCCGTTTCGGCTTTTACG |
| CTGCCTGAAGCATGGCGGCGGCGCAGCAACATTCGGCTGATTTTCAAGCGTCCCATTAC |
| CAGCGTGATGCAGTGCGCGCACGGCAACAACAAGCCAAGGCCGCATTCCTTCCCCATGTA |
| TCCGCCAATGCCAGCTACCAGCGCCACCCGCCATCGATTTCTTCCACCCGCGAAACACAG |
| GGATGGAGCGTGCAGGTGGGACAAACCTTATTTGACGCTGCCAAATTTGCACAATACCGC |

-continued

Polynucleotide and Polypeptide Sequences

CAAAGCAGGTTCGATACGCAGGCTGCAGAACAGCGTTTCGATGCGGCACGCGAAGAATTG

CTGTTGAAAGTTGCCGAAAGTTATTTCAACGTTTTACTCAGCCGAGACACCGTTCCCGCC

CATGCGCCGGAAAAAGAGGCTTATGCCCAGCAGGTAAGGCAGGCGCAGGCTTTATTCAAT

AAAGGTGCTGCCACCGCGCTGGATATTCACGAAGCCAAAGCCGGTTACGACAATGCCCTG

GCCCAAGAAATCGCCGTATTGGCTGAGAAACAAACCTATGAAAACCAGTTGAACGACTAC

ACCGGCCTGGACAGCAAACAAATCGAGGCCATAGATACCGCCAACCTGTTGGCACGCTAT

CTGCCCAAGCTGGAACGTTACAGTCTGGATGAATGGCAGCGCATTGCCTTATCCAACAAT

CATGAATACCGGATGCAGCAGCTTGCCCTGCAAAGCAGCGCACAGGCGCTTCGGGCAGCA

CAGAACAGCCGCTATCCCACCGTTTCTGCCCATGTCGGCTATCAGAATAACCTCTACACT

TCATCTGCGCAGAATAATGACTACCACTATCGGGGCAAAGGGATGAGCGTCGGCGTACAG

TTGAATTTGCCGCTTTATACCGGCGGAGAATTGTCGGGCAAAATCCATGAAGCCGAAGCG

CAATAGGGGGCTGCCGAAGCACAGCTGACCGCAACCGAGCGGCACATCAAACTCGCCGTA

CGCCAGGCTTATACCGAAAGCGGTGCGGCGCGTTACCAAATCATGCCGCAAGAACGGGTT

TTGGAAAGCAGCCGTTTGAAACTGAAATCGACCGAAACCGGCCAACAATACGGCATCCGC

AACCGGCTGGAAGTAATACGGGCGCGGCAGGAAGTCGCCCAAGCAGAACAGAAACTGGCT

CAAGCACGCTATAAATTCATGCTGGCTTATTTGCGCTTGGTGAAAGAGAGCGGGTTAGGG

TTGGAAACGGTATTTGCGGAATAA

SEQ ID NO:26
Neisseria meningitidis BASB048 polypeptide sequence deduced from the polynucleotide
sequence of SEQ ID NO:25

MTLLNLMIMQDYGISVCLTLTPYLQHELFSANKSYFSKYILPVSLFTLPLSLSPSVSAFT

LPEAWRAAQQHSADFQASHYQRDAVRARQQQAKAAFLPHVSANASYQRQPPSISSTRETQ

GWSVQVGQTLFDAAKFAQYRQSRFDTQAAEQRFDAAREELLLKVAESYFNVLLSRDTVAA

HAAEKEAYAQQVRQAQALFNKGAATALDIHEAKAGYDNALAQEIAVLAEKQTYENQLNDY

TGLDSKQIEAIDTANLLARYLPKLERYSLDEWQRIALSNNHEYRMQQLALQSSGQALRAA

QNSRYPTVSAHVGYQNNLYTSSAQNNDYHYRGKGMSVGVQLNLPLYTGGELSGKIHEAEA

QYGAAEAQLTATERHIKLAVRQAYTESGAARYQIMAQERVLESSRLKLKSTETGQQYGIR

NRLEVIRARQEVAQAEQKLAQARYKFMLAYLRLVKESGLGLETVFAE

Deposited Materials

A deposit containing a *Neisseria meningitidis* Serogroup B strain has been deposited with the American Type Culture Collection (herein "

What is claimed is:

1. An isolated polynucleotide comprising a polynucleotide sequence that encodes the polypeptide of SEQ ID NO:2, or the full complement thereof.

2. The isolated polynucleotide of claim 1, wherein the polynucleotide sequence encodes the polypeptide consisting of SEQ ID NO:2.

3. The isolated polynucleotide of claim 1, wherein the polynucleotide sequence comprises SEQ ID NO:1.

4. The isolated polynucleotide of claim 1, wherein the polynucleotide sequence consists of SEQ ID NO:1.

5. A recombinant expression vector comprising the isolated polynucleotide of claim 1.

6. A recombinant expression vector comprising the isolated polynucleotide of claim 3.

7. An isolated host cell comprising the expression vector of claim 5.

8. An isolated host cell comprising the expression vector of claim 6.

9. An immunogenic composition comprising the recombinant expression vector of claim 5 and a pharmaceutically acceptable carrier.

10. The immunogenic composition of claim 9, further comprising an adjuvant.

11. An immunogenic composition comprising the recombinant expression vector of claim 6 and a pharmaceutically acceptable carrier.

12. The immunogenic composition of claim 11, further comprising an adjuvant.

* * * * *

UNITED STATES PATENT AND TRADEMARK OFFICE
CERTIFICATE OF CORRECTION

| | | |
|---|---|---|
| PATENT NO. | : 7,521,549 B2 | Page 1 of 1 |
| APPLICATION NO. | : 10/755115 | |
| DATED | : April 21, 2009 | |
| INVENTOR(S) | : Ruelle et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 883 days.

Signed and Sealed this

Seventh Day of September, 2010

David J. Kappos
*Director of the United States Patent and Trademark Office*

SEQUENCE LISTING

<160> NUMBER OF SEQ ID NOS: 26

<210> SEQ ID NO 1
<211> LENGTH: 671
<212> TYPE: DNA
<213> ORGANISM: Neisseria meningitidis

<400> SEQUENCE: 1

```
atgaaaaccg tttccaccgc cgttgtcctt gccgccgctg ccgtttcact gaccggctgt      60
gcgaccgaat cctcacgcag tctcgaggta gagaaagtcg cctcctacaa tacgcaatac    120
cacggcgtgc gtaccccgat ttccgtcgga acattcgaca accgctccag cttccaaaaa    180
ggcattttct ccgacgggga agaccgtttg ggcagccagg caaaaaccat tctggtaacg    240
cacctgcaac agaccaaccg cttcaacgta ctgaaccgca ccaatttgaa cgcattaaaa    300
caggaatccg gcatttccgg caaagcgcat aacctgaaag cgcagatta tgtcgttact    360
ggcgatgtaa ccgaattcgg acgcagagat gtcggcgatc atcagctctt cggcattttg    420
ggtcgcggca atcgcaaat cgcctatgca aaagtggctc tgaatatcgt caacgtcaat    480
acttccgaaa tcgtctattc cgcacagggc gcgggcgaat acgcacttc caaccgtgaa    540
atcatcggtt tcggcggcac ttccggctac gatgcgactt tgaacggcaa agttttagac    600
ttggcaatcc gcgaaccgtc aacagcctgg ttcaggctgt tgacaacggc gcatggcaac    660
ccaaccgtta a                                                          671
```

<210> SEQ ID NO 2
<211> LENGTH: 223
<212> TYPE: PRT
<213> ORGANISM: Neisseria meningitidis

<400> SEQUENCE: 2

```
Met Lys Thr Val Ser Thr Ala Val Val Leu Ala Ala Ala Ala Val Ser
  1               5                  10                  15
Leu Thr Gly Cys Ala Thr Glu Ser Ser Arg Ser Leu Glu Val Glu Lys
                 20                  25                  30
Val Ala Ser Tyr Asn Thr Gln Tyr His Gly Val Arg Thr Pro Ile Ser
             35                  40                  45
Val Gly Thr Phe Asp Asn Arg Ser Ser Phe Gln Lys Gly Ile Phe Ser
         50                  55                  60
Asp Gly Glu Asp Arg Leu Gly Ser Gln Ala Lys Thr Ile Leu Val Thr
 65                  70                  75                  80
His Leu Gln Gln Thr Asn Arg Phe Asn Val Leu Asn Arg Thr Asn Leu
                 85                  90                  95
Asn Ala Leu Lys Gln Glu Ser Gly Ile Ser Gly Lys Ala His Asn Leu
                100                 105                 110
Lys Gly Ala Asp Tyr Val Val Thr Gly Asp Val Thr Glu Phe Gly Arg
            115                 120                 125
Arg Asp Val Gly Asp His Gln Leu Phe Gly Ile Leu Gly Arg Gly Lys
        130                 135                 140
Ser Gln Ile Ala Tyr Ala Lys Val Ala Leu Asn Ile Val Asn Val Asn
145                 150                 155                 160
Thr Ser Glu Ile Val Tyr Ser Ala Gln Gly Ala Gly Glu Tyr Ala Leu
                165                 170                 175
Ser Asn Arg Glu Ile Ile Gly Phe Gly Gly Thr Ser Gly Tyr Asp Ala
            180                 185                 190
```

Thr Leu Asn Gly Lys Val Leu Asp Leu Ala Ile Arg Glu Pro Ser Thr
        195                 200                 205

Ala Trp Phe Arg Leu Leu Thr Thr Ala His Gly Asn Pro Thr Val
    210                 215                 220

<210> SEQ ID NO 3
<211> LENGTH: 672
<212> TYPE: DNA
<213> ORGANISM: Neisseria meningitidis

<400> SEQUENCE: 3
atgaaaaccg tttccaccgc cgttgtcctt gccgccgctg ccgtttcact gaccggctgt     60
gcgaccgaat cctcacgcag tctcgaggta gagaaagtcg cctcctacaa tacgcaatac    120
cacggcgtgc gtaccccgat ttccgtcgga acattcgaca accgctccag cttccaaaaa    180
ggcattttct ccgacgggga agaccgtttg ggcagccagg caaaaaccat tctggtaacg    240
cacctgcaac agaccaaccg cttcaacgta ctgaaccgca ccaatttgaa cgcattaaaa    300
caggaatccg gcatttccgg caaagcgcat aacctgaaag cgcagatta tgtcgttact     360 ggcgatgtaa ccgaattcgg acgcagagat gtcggcgatc atcagctctt cggcattttg    420
ggtcgcggca atcgcaaat cgcctatgca aaagtggctc tgaatatcgt caacgtcaat     480
acttccgaaa tcgtctattc cgcacagggc gcgggcgaat acgcactttc caaccgtgaa    540
atcatcggtt cggcggcac ttccggctac gatgcgactt tgaacggcaa agttttagac     600
ttggcaatcc gcgaagccgt caacagcctg gttcaggctg ttgacaacgg cgcatggcaa    660
cccaaccgtt aa                                                        672

<210> SEQ ID NO 4
<211> LENGTH: 223
<212> TYPE: PRT
<213> ORGANISM: Neisseria meningitidis

<400> SEQUENCE: 4

Met Lys Thr Val Ser Thr Ala Val Val Leu Ala Ala Ala Val Ser
1               5                   10                  15

Leu Thr Gly Cys Ala Thr Glu Ser Ser Arg Ser Leu Glu Val Glu Lys
        20                  25                  30

Val Ala Ser Tyr Asn Thr Gln Tyr His Gly Val Arg Thr Pro Ile Ser
    35                  40                  45

Val Gly Thr Phe Asp Asn Arg Ser Ser Phe Gln Lys Gly Ile Phe Ser
    50                  55                  60

Asp Gly Glu Asp Arg Leu Gly Ser Gln Ala Lys Thr Ile Leu Val Thr
65                  70                  75                  80

His Leu Gln Gln Thr Asn Arg Phe Asn Val Leu Asn Arg Thr Asn Leu
                85                  90                  95

Asn Ala Leu Lys Gln Glu Ser Gly Ile Ser Gly Lys Ala His Asn Leu
            100                 105                 110

Lys Gly Ala Asp Tyr Val Val Thr Gly Asp Val Thr Glu Phe Gly Arg
        115                 120                 125

Arg Asp Val Gly Asp His Gln Leu Phe Gly Ile Leu Gly Arg Gly Lys
    130                 135                 140

Ser Gln Ile Ala Tyr Ala Lys Val Ala Leu Asn Ile Val Asn Val Asn
145                 150                 155                 160

Thr Ser Glu Ile Val Tyr Ser Ala Gln Gly Ala Gly Glu Tyr Ala Leu
                165                 170                 175

Ser Asn Arg Glu Ile Ile Gly Phe Gly Gly Thr Ser Gly Tyr Asp Ala
            180                 185                 190

Thr Leu Asn Gly Lys Val Leu Asp Leu Ala Ile Arg Glu Ala Val Asn
        195                 200                 205

Ser Leu Val Gln Ala Val Asp Asn Gly Ala Trp Gln Pro Asn Arg
    210                 215                 220

<210> SEQ ID NO 5
<211> LENGTH: 672
<212> TYPE: DNA
<213> ORGANISM: Neisseria meningitidis

<400> SEQUENCE: 5

| | | | | | |
|---|---|---|---|---|---|
| atgaaaaccg | tttccaccgc | cgttgtcctt | gccgccgctg | ccgtttcact | gaccggctgt | 60 |
| gcgaccgaat | cctcacgcag | tctcgaggta | gagaaagtcg | cctcctacaa | tacgcaatat | 120 |
| cacggtgttc | gtaccccgat | ttccgtcgga | acattcgaca | accgctccag | cttccaaaaa | 180 |
| ggcattttct | ccgacgggga | agaccgtttg | ggcagccagg | caaaaaccat | tctagtaacg | 240 |
| cacctgcaac | agaccaaccg | cttcaacgta | ctgaaccgca | ccaatttgaa | cgcattaaaa | 300 |
| caggaatccg | gcatttccgg | caaagcgcat | aacctgaaag | gcgcagatta | tgtcgttacc | 360 |
| ggcgatgtaa | ccgaattcgg | acgcagagat | gtcggcgatc | atcagctctt | cggcattttg | 420 |
| ggtcgcggca | atcgcaaat | cgcctatgca | aaagtggctc | tgaatatcgt | caacgtcaat | 480 |
| acttccgaaa | tcgtctattc | cgcacagggc | gcgggcgaat | acgcactttc | caaccgtgaa | 540 |
| atcatcggtt | tcggcggcac | ttccggctac | gatgcgactt | tgaacggcaa | agttttagac | 600 |
| ttggcaatcc | gcgaagccgt | caacagcctg | gttcaggctg | ttgacaacgg | cgcatggcaa | 660 |
| cccaaccgtt | aa | | | | | 672 |

<210> SEQ ID NO 6
<211> LENGTH: 223
<212> TYPE: PRT
<213> ORGANISM: Neisseria meningitidis

<400> SEQUENCE: 6

Met Lys Thr Val Ser Thr Ala Val Val Leu Ala Ala Ala Val Ser
1               5                   10                  15

Leu Thr Gly Cys Ala Thr Glu Ser Ser Arg Ser Leu Glu Val Glu Lys
                20                  25                  30

Val Ala Ser Tyr Asn Thr Gln Tyr His Gly Val Arg Thr Pro Ile Ser
            35                  40                  45

Val Gly Thr Phe Asp Asn Arg Ser Ser Phe Gln Lys Gly Ile Phe Ser
        50                  55                  60

Asp Gly Glu Asp Arg Leu Gly Ser Gln Ala Lys Thr Ile Leu Val Thr
65                  70                  75                  80

His Leu Gln Gln Thr Asn Arg Phe Asn Val Leu Asn Arg Thr Asn Leu
                85                  90                  95

Asn Ala Leu Lys Gln Glu Ser Gly Ile Ser Gly Lys Ala His Asn Leu
            100                 105                 110

Lys Gly Ala Asp Tyr Val Val Thr Gly Asp Val Thr Glu Phe Gly Arg
        115                 120                 125

Arg Asp Val Gly Asp His Gln Leu Phe Gly Ile Leu Gly Arg Gly Lys
    130                 135                 140

Ser Gln Ile Ala Tyr Ala Lys Val Ala Leu Asn Ile Val Asn Val Asn
145                 150                 155                 160

```
Thr Ser Glu Ile Val Tyr Ser Ala Gln Gly Ala Gly Glu Tyr Ala Leu
                165                 170                 175

Ser Asn Arg Glu Ile Ile Gly Phe Gly Gly Thr Ser Gly Tyr Asp Ala
            180                 185                 190

Thr Leu Asn Gly Lys Val Leu Asp Leu Ala Ile Arg Glu Ala Val Asn
        195                 200                 205

Ser Leu Val Gln Ala Val Asp Asn Gly Ala Trp Gln Pro Asn Arg
    210                 215                 220

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aatgaaaacc gtttccaccg c                                           21

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
tcatttctcc ttaacggt                                               18

<210> SEQ ID NO 9
<211> LENGTH: 44
<212> TYPE: DNA
<213> ORGANISM: Artificial Sequence
<220> FEATURE:
<223> OTHER INFORMATION: Primer

<400> SEQUENCE: 9
aggcagaggc atatgaaaac cgtttccacc gccgttgtcc ttgc                  44

<210> SEQ ID NO 10
<211> LENGTH: 45
<212> TYPE: DNA
<213> ORGANISM: Artificial Sequence
<220> FEATURE:
<223> OTHER INFORMATION: Primer

<400> SEQUENCE: 10
aggcagaggg tcgactttct ccttaacggt tgggttgcca tgcgc                 45

<210> SEQ ID NO 11
<211> LENGTH: 489
<212> TYPE: DNA
<213> ORGANISM: Neisseria meningitidis

<400> SEQUENCE: 11
atgaaaaaat accttatccc tctttccatt gcggcagttc tttccggctg ccagtctatt    60
tatgtgccca cattgacgga atccccgtg  aatcctatca ataccgtcaa acggaagca    120 cctgcaaaag gtttccgcct tgcctcttcg cattggacgg atgttgccaa atcagcgat    180 gaagcgacgc gcttgggcta tcaggtgggt atcggtaaaa tgaccaaggt tcaggcggcg    240
caatatctga caacttcag  aaaacgcctg gtcggacgca atgccgtcga tgacagtatg    300
```

```
tatgaaatct acctgcgttc ggcgatagac agccagcggg gcgcaatcaa tacggaacag    360
tccaagctgt atatccagaa tgccttgcgc ggctggcagc agcgttggaa aaatatggat    420
gtcaaaccca caaccccgc atttaccaac tttttgatgg aagtgatgaa gatgcagccc    480
ttgaaatga                                                            489
```

```
<210> SEQ ID NO 12
<211> LENGTH: 162
<212> TYPE: PRT
<213> ORGANISM: Neisseria meningitidis

<400> SEQUENCE: 12
```

Met Lys Lys Tyr Leu Ile Pro Leu Ser Ile Ala Ala Val Leu Ser Gly
1               5                   10                  15

Cys Gln Ser Ile Tyr Val Pro Thr Leu Thr Glu Ile Pro Val Asn Pro
            20                  25                  30

Ile Asn Thr Val Lys Thr Glu Ala Pro Ala Lys Gly Phe Arg Leu Ala
        35                  40                  45

Ser Ser His Trp Thr Asp Val Ala Lys Ile Ser Asp Glu Ala Thr Arg
    50                  55                  60

Leu Gly Tyr Gln Val Gly Ile Gly Lys Met Thr Lys Val Gln Ala Ala
65                  70                  75                  80

Gln Tyr Leu Asn Asn Phe Arg Lys Arg Leu Val Gly Arg Asn Ala Val
                85                  90                  95

Asp Asp Ser Met Tyr Glu Ile Tyr Leu Arg Ser Ala Ile Asp Ser Gln
            100                 105                 110

Arg Gly Ala Ile Asn Thr Glu Gln Ser Lys Leu Tyr Ile Gln Asn Ala
        115                 120                 125

Leu Arg Gly Trp Gln Gln Arg Trp Lys Asn Met Asp Val Lys Pro Asn
    130                 135                 140

Asn Pro Ala Phe Thr Asn Phe Leu Met Glu Val Met Lys Met Gln Pro
145                 150                 155                 160

Leu Lys

```
<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
atgaaaaaat accttatccc tctttcc                                         27

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
tcatttcaag ggctgcat                                                   18

<210> SEQ ID NO 15
<211> LENGTH: 45
<212> TYPE: DNA
<213> ORGANISM: Artificial Sequence
<220> FEATURE:
<223> OTHER INFORMATION: Primer
```

<400> SEQUENCE: 15

```
aggcagaggc atatgaaaaa ataccttatc cctctttcca ttgcc                45
```

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16

```
aggcagaggc tcgagtttca agggctgcat cttcatcact tc                   42
```

<210> SEQ ID NO 17
<211> LENGTH: 1401
<212> TYPE: DNA
<213> ORGANISM: Neisseria meningitidis

<400> SEQUENCE: 17

```
atgacccctt ccgcactgaa aaaaaccgtc ctgctgctcg gcactgcctt tgccgccgca     60
tccgcacaag cctccggcta ccacttcggc acacagtcgg tcaacgcgca aagcacggca    120
aatgccgccg ccgcagaagc cgccgacgca tcgaccatct tctacaaccc tgccggcctg    180
accaaactcg acagcagcca gatttccgtc aacgccaaca tcgtgctgcc cagcattcat    240
tatgaggcgg attccgccac cgactttacc gggcttcccg tccaaggttc gaaaagcggc    300
aaaatcacca aaaccacggt cgcgccccac atctacggcg catacaaagt caacgacaat    360
ctgaccgtag gcttgggcgt gtacgtcccc ttcggttctg ccaccgaata cgaaaaagat    420
tccgtgttgc gccacaacat caacaaactc ggtctgacca gatcgccgt cgaacctgtc    480
gccgcgtgga aactcaacga ccgccattcc ttcggcgcag gcatcatcgc ccaacatact    540
tccgccgaac tgcgcaaata tgccgactgg gggattaaga gtaaagcaga gatattgacg    600
gcaaaaccgc ccaaacctaa cggtgtagcc gaagctgcaa aaattcaggc cgacggacac    660
gccgatgtca aaggcagcga ttggggcttc ggctaccaac tggcgtggat gtgggacatc    720
aacgaccgtg cgcgcgtggg cgtgaactac cgttccaaag tctcgcacac gctcaaaggc    780
gatgccgaat gggcggcaga cggcgcggcg gcgaaagcaa tgtggagtac gatgcttgca    840
gcaaacggct acacggcgaa tgaaaaagcc cgcgttaaaa tcgttacgcc tgagtctttg    900
tccgtacacg gtatgtacaa agtgtccgat aaagccgacc tgttcggcga cgtaacttgg    960
acgcgccaca gccgcttcga taaggcggaa ctggttttg aaaagaaaa aaccgtcgtc   1020
aaaggcaaat ccgaccgcac caccatcacc cccaactggc gcaacaccta caagtcggc   1080
ttcggcggtt cttatcaaat cagcgaaccg ctgcaactgc gcgccggcat cgcttttgac   1140
aaatcgcccg tccgcaacgc cgactaccgc atgaacagcc tgcccgacgg caaccgcatc   1200
tggttctccg ccggtatgaa ataccatatc ggtaaaaacc acgtcgtcga tgccgcctac   1260
acccacatcc acatcaacga caccacctac cgcacggcga aggcaagcgg caacgatgtg   1320
gacagcaaag gcgcgtcttc cgcacgtttc aaaaaccacg ccgacatcat cggcctgcaa   1380
tacacctaca aattcaaata a                                            1401
```

<210> SEQ ID NO 18
<211> LENGTH: 466
<212> TYPE: PRT
<213> ORGANISM: Neisseria meningitidis

```
<400> SEQUENCE: 18

Met Thr Pro Ser Ala Leu Lys Lys Thr Val Leu Leu Leu Gly Thr Ala
 1               5                  10                  15

Phe Ala Ala Ala Ser Ala Gln Ala Ser Gly Tyr His Phe Gly Thr Gln
             20                  25                  30

Ser Val Asn Ala Gln Ser Thr Ala Asn Ala Ala Ala Glu Ala Ala
         35                  40                  45

Asp Ala Ser Thr Ile Phe Tyr Asn Pro Ala Gly Leu Thr Lys Leu Asp
     50                  55                  60

Ser Ser Gln Ile Ser Val Asn Ala Asn Ile Val Leu Pro Ser Ile His
65                  70                  75                  80

Tyr Glu Ala Asp Ser Ala Thr Asp Phe Thr Gly Leu Pro Val Gln Gly
                 85                  90                  95

Ser Lys Ser Gly Lys Ile Thr Lys Thr Thr Val Ala Pro His Ile Tyr
            100                 105                 110

Gly Ala Tyr Lys Val Asn Asp Asn Leu Thr Val Gly Leu Gly Val Tyr
            115                 120                 125

Val Pro Phe Gly Ser Ala Thr Glu Tyr Glu Lys Asp Ser Val Leu Arg
        130                 135                 140

His Asn Ile Asn Lys Leu Gly Leu Thr Ser Ile Ala Val Glu Pro Val
145                 150                 155                 160

Ala Ala Trp Lys Leu Asn Asp Arg His Ser Phe Gly Ala Gly Ile Ile
                165                 170                 175

Ala Gln His Thr Ser Ala Glu Leu Arg Lys Tyr Ala Asp Trp Gly Ile
            180                 185                 190

Lys Ser Lys Ala Glu Ile Leu Thr Ala Lys Pro Pro Lys Pro Asn Gly
        195                 200                 205

Val Ala Glu Ala Ala Lys Ile Gln Ala Asp Gly His Ala Asp Val Lys
    210                 215                 220

Gly Ser Asp Trp Gly Phe Gly Tyr Gln Leu Ala Trp Met Trp Asp Ile
225                 230                 235                 240

Asn Asp Arg Ala Arg Val Gly Val Asn Tyr Arg Ser Lys Val Ser His
                245                 250                 255

Thr Leu Lys Gly Asp Ala Glu Trp Ala Ala Asp Gly Ala Ala Ala Lys
            260                 265                 270

Ala Met Trp Ser Thr Met Leu Ala Ala Asn Gly Tyr Thr Ala Asn Glu
        275                 280                 285

Lys Ala Arg Val Lys Ile Val Thr Pro Glu Ser Leu Ser Val His Gly
    290                 295                 300

Met Tyr Lys Val Ser Asp Lys Ala Asp Leu Phe Gly Asp Val Thr Trp
305                 310                 315                 320

Thr Arg His Ser Arg Phe Asp Lys Ala Glu Leu Val Phe Glu Lys Glu
                325                 330                 335

Lys Thr Val Val Lys Gly Lys Ser Asp Arg Thr Thr Ile Thr Pro Asn
            340                 345                 350

Trp Arg Asn Thr Tyr Lys Val Gly Phe Gly Gly Ser Tyr Gln Ile Ser
        355                 360                 365

Glu Pro Leu Gln Leu Arg Ala Gly Ile Ala Phe Asp Lys Ser Pro Val
    370                 375                 380

Arg Asn Ala Asp Tyr Arg Met Asn Ser Leu Pro Asp Gly Asn Arg Ile
385                 390                 395                 400

Trp Phe Ser Ala Gly Met Lys Tyr His Ile Gly Lys Asn His Val Val
                405                 410                 415
```

```
Asp Ala Ala Tyr Thr His Ile His Ile Asn Asp Thr Thr Tyr Arg Thr
            420                 425                 430

Ala Lys Ala Ser Gly Asn Asp Val Asp Ser Lys Gly Ala Ser Ser Ala
        435                 440                 445

Arg Phe Lys Asn His Ala Asp Ile Ile Gly Leu Gln Tyr Thr Tyr Lys
    450                 455                 460

Phe Lys
465
```

<210> SEQ ID NO 19
<211> LENGTH: 1329
<212> TYPE: DNA
<213> ORGANISM: Neisseria meningitidis

<400> SEQUENCE: 19

```
tccggctacc acttcggcac acagtcggtc aacgcgcaaa gcacggcaaa tgccgccgcc      60
gcagaagccg ccgacgcatc gaccatcttc tacaaccctg ccggcctgac caaactcgac     120
agcagccaga tttccgtcaa cgccaacatc gtgctgccca gcattcatta tgaggcggat     180
tccgccaccg actttaccgg gcttcccgtc aaggttcga aaagcggcaa atcaccaaa       240
accacggtcg cgccccacat ctacggcgca tacaaagtca cgacaatct gaccgtgggc      300
ttgggcgtgt acgtcccctt cggctctgcc accgaatacg aaaaagattc cgtgttgcgc     360
cacaacatca caaaactcgg tctgaccagc atccgtcg aacctgtcgc cgcgtggaaa       420
ctcaacgacc gccattcctt cggcgcaggc atcatcgccc aacatacttc cgccgaactg     480
cgcaaatatg ccgactgggg gattaagagt aaagcagaga tattgacggc aaaaccgccc    540
aaacctaacg gtgtagccga agctgcaaaa attcaggccg acggacacgc cgatgtcaaa    600
ggcagcgatt ggggcttcgg ctaccaactg gcgtggatgt gggacatcaa cgaccgtgcg     660
cgcgtgggcg tgaactaccg ttccaaagtc tcgcacacgc tcaaaggcga tgccgaatgg    720
gcggcagacg gcgcggcggc gaaagcaatg tggagtacga tgcttgcagc aaacggctac     780
acggcgaatg aaaaagcccg cgttaaaatc gttacgcctg agtctttgtc cgtacacggt     840
atgtacaaag tgtccgataa agccgacctg ttcggcgacg taacttggac gcgccacagc    900
cgcttcgata aggcggaact ggttttttgaa aagaaaaaaa ccgtcgtcaa aggcaaatcc     960
gaccgcacca ccatcacccc caactggcgc aacacctaca aagtcggctt cggcggttct    1020
tatcaaatca gcgaaccgct gcaactgcgc gccggcatgc cttttgacaa atcgcccgtc    1080
cgcaacgccg actaccgcat gaacagccta cccgacggca accgcatctg gttctccgcc   1140
ggtatgaaat accatatcgg taaaaaccac gtcgtcgatg ccgcctacac ccacatccac     1200
atcaacgaca ccagctaccg cacggcgaag gcaagcggca cgatgtgga cagcaaaggc     1260
gcgtcttccg cacgttttcaa aaaccacgcc gacatcatcg gtctgcaata cacctacaaa    1320
ttcaaataa                                                             1329
```

<210> SEQ ID NO 20
<211> LENGTH: 442
<212> TYPE: PRT
<213> ORGANISM: Neisseria meningitidis

<400> SEQUENCE: 20

```
Ser Gly Tyr His Phe Gly Thr Gln Ser Val Asn Ala Gln Ser Thr Ala
1               5                   10                  15

Asn Ala Ala Ala Ala Glu Ala Ala Asp Ala Ser Thr Ile Phe Tyr Asn
```

-continued

```
                    20                  25                  30
Pro Ala Gly Leu Thr Lys Leu Asp Ser Ser Gln Ile Ser Val Asn Ala
                35                  40                  45
Asn Ile Val Leu Pro Ser Ile His Tyr Glu Ala Asp Ser Ala Thr Asp
             50                  55                  60
Phe Thr Gly Leu Pro Val Gln Gly Ser Lys Ser Gly Lys Ile Thr Lys
 65                  70                  75                  80
Thr Thr Val Ala Pro His Ile Tyr Gly Ala Tyr Lys Val Asn Asp Asn
                 85                  90                  95
Leu Thr Val Gly Leu Gly Val Tyr Val Pro Phe Gly Ser Ala Thr Glu
                100                 105                 110
Tyr Glu Lys Asp Ser Val Leu Arg His Asn Ile Asn Lys Leu Gly Leu
                115                 120                 125
Thr Ser Ile Ala Val Glu Pro Val Ala Trp Lys Leu Asn Asp Arg
    130                 135                 140
His Ser Phe Gly Ala Gly Ile Ile Ala Gln His Thr Ser Ala Glu Leu
145                 150                 155                 160
Arg Lys Tyr Ala Asp Trp Gly Ile Lys Ser Lys Ala Glu Ile Leu Thr
                165                 170                 175
Ala Lys Pro Pro Lys Pro Asn Gly Val Ala Glu Ala Ala Lys Ile Gln
                180                 185                 190
Ala Asp Gly His Ala Asp Val Lys Gly Ser Asp Trp Gly Phe Gly Tyr
                195                 200                 205
Gln Leu Ala Trp Met Trp Asp Ile Asn Asp Arg Ala Arg Val Gly Val
    210                 215                 220
Asn Tyr Arg Ser Lys Val Ser His Thr Leu Lys Gly Asp Ala Glu Trp
225                 230                 235                 240
Ala Ala Asp Gly Ala Ala Lys Ala Met Trp Ser Thr Met Leu Ala
                245                 250                 255
Ala Asn Gly Tyr Thr Ala Asn Glu Lys Ala Arg Val Lys Ile Val Thr
                260                 265                 270
Pro Glu Ser Leu Ser Val His Gly Met Tyr Lys Val Ser Asp Lys Ala
                275                 280                 285
Asp Leu Phe Gly Asp Val Thr Trp Thr Arg His Ser Arg Phe Asp Lys
    290                 295                 300
Ala Glu Leu Val Phe Glu Lys Glu Lys Thr Val Lys Gly Lys Ser
305                 310                 315                 320
Asp Arg Thr Thr Ile Thr Pro Asn Trp Arg Asn Thr Tyr Lys Val Gly
                325                 330                 335
Phe Gly Gly Ser Tyr Gln Ile Ser Glu Pro Leu Gln Leu Arg Ala Gly
                340                 345                 350
Ile Ala Phe Asp Lys Ser Pro Val Arg Asn Ala Asp Tyr Arg Met Asn
                355                 360                 365
Ser Leu Pro Asp Gly Asn Arg Ile Trp Phe Ser Ala Gly Met Lys Tyr
    370                 375                 380
His Ile Gly Lys Asn His Val Val Asp Ala Ala Tyr Thr His Ile His
385                 390                 395                 400
Ile Asn Asp Thr Ser Tyr Arg Thr Ala Lys Ala Ser Gly Asn Asp Val
                405                 410                 415
Asp Ser Lys Gly Ala Ser Ser Ala Arg Phe Lys Asn His Ala Asp Ile
                420                 425                 430
Ile Gly Leu Gln Tyr Thr Tyr Lys Phe Lys
    435                 440
```

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
tgagtggaaa atgccgtctg aagt                                            24

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
tgcaccccgt cattcctgtc t                                               21

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
catagcacca tggccggcta ccacttcg                                        28

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
ctagtctaga ttatttgaat ttgtaggtgt at                                   32

<210> SEQ ID NO 25
<211> LENGTH: 1404
<212> TYPE: DNA
<213> ORGANISM: Neisseria meningitidis

<400> SEQUENCE: 25
atgacattgc tcaatctaat gataatgcaa gattacggta tttccgtttg cctgacactg 60
acgccctatt tgcaacatga actattttcg gctatgaaat cctatttttc caaatatatc 120
ctacccgttt cactttttac cttgccacta tccctttccc catccgtttc ggcttttacg 180
ctgcctgaag catggcgggc ggcgcagcaa cattcggctg attttcaagc gtcccattac 240
cagcgtgatg cagtgcgcgc acggcaacaa caagccaagg ccgcattcct tccccatgta 300
tccgccaatg ccagctacca gcgccagccg ccatcgattt cttccacccg cgaaacacag 360
ggatggagcg tgcaggtggg acaaacctta tttgacgctg ccaaatttgc acaataccgc 420
caaagcaggt tcgatacgca ggctgcagaa cagcgtttcg atgcggcacg cgaagaattg 480
ctgttgaaag ttgccgaaag ttatttcaac gttttactca gccgagacac cgttgccgcc 540
catgcggcgg aaaaagaggc ttatgcccag caggtaaggc aggcgcaggc tttattcaat 600
aaaggtgctg ccaccgcgct ggatattcac gaagccaaag ccggttacga caatgccctg 660

```
gcccaagaaa tcgccgtatt ggctgagaaa caaacctatg aaaaccagtt gaacgactac    720
accggcctgg acagcaaaca aatcgaggcc atagataccg ccaacctgtt ggcacgctat    780
ctgcccaagc tgaacgtta cagtctggat gaatggcagc gcattgcctt atccaacaat    840
catgaatacc ggatgcagca gcttgccctg caaagcagcg acaggcgct tcgggcagca    900
cagaacagcc gctatcccac cgtttctgcc catgtcggct atcagaataa cctctacact    960
tcatctgcgc agaataatga ctaccactat cggggcaaag ggatgagcgt cggcgtacag   1020
ttgaatttgc cgctttatac cggcggagaa ttgtcgggca aaatccatga agccgaagcg   1080
caatacgggg ctgccgaagc acagctgacc gcaaccgagc ggcacatcaa actcgccgta   1140
cgccaggctt ataccgaaag cggtgcggcg cgttaccaaa tcatggcgca agaacgggtt   1200
ttggaaagca gccgtttgaa actgaaatcg accgaaaccg ccaacaata cggcatccgc   1260
aaccggctgg aagtaatacg ggcgcggcag gaagtcgccc aagcagaaca gaaactggct   1320
caagcacggt ataaattcat gctggcttat ttgcgcttgg tgaaagagag cgggttaggg   1380
ttggaaacgg tatttgcgga ataa                                          1404
```

<210> SEQ ID NO 26
<211> LENGTH: 467
<212> TYPE: PRT
<213> ORGANISM: Neisseria meningitidis

<400> SEQUENCE: 26

```
Met Thr Leu Leu Asn Leu Met Ile Met Gln Asp Tyr Gly Ile Ser Val
 1               5                   10                  15

Cys Leu Thr Leu Thr Pro Tyr Leu Gln His Glu Leu Phe Ser Ala Met
                20                  25                  30

Lys Ser Tyr Phe Ser Lys Tyr Ile Leu Pro Val Ser Leu Phe Thr Leu
            35                  40                  45

Pro Leu Ser Leu Ser Pro Ser Val Ser Ala Phe Thr Leu Pro Glu Ala
        50                  55                  60

Trp Arg Ala Ala Gln Gln His Ser Ala Asp Phe Gln Ala Ser His Tyr
65                  70                  75                  80

Gln Arg Asp Ala Val Arg Ala Gln Gln Ala Lys Ala Ala Phe
                85                  90                  95

Leu Pro His Val Ser Ala Asn Ala Ser Tyr Gln Arg Gln Pro Pro Ser
            100                 105                 110

Ile Ser Ser Thr Arg Glu Thr Gln Gly Trp Ser Val Gln Val Gly Gln
        115                 120                 125

Thr Leu Phe Asp Ala Ala Lys Phe Ala Gln Tyr Arg Gln Ser Arg Phe
    130                 135                 140

Asp Thr Gln Ala Ala Glu Gln Arg Phe Asp Ala Ala Arg Glu Glu Leu
145                 150                 155                 160

Leu Leu Lys Val Ala Glu Ser Tyr Phe Asn Val Leu Leu Ser Arg Asp
                165                 170                 175

Thr Val Ala Ala His Ala Ala Glu Lys Glu Ala Tyr Ala Gln Gln Val
            180                 185                 190

Arg Gln Ala Gln Ala Leu Phe Asn Lys Gly Ala Ala Thr Ala Leu Asp
        195                 200                 205

Ile His Glu Ala Lys Ala Gly Tyr Asp Asn Ala Leu Ala Gln Glu Ile
    210                 215                 220

Ala Val Leu Ala Glu Lys Gln Thr Tyr Glu Asn Gln Leu Asn Asp Tyr
225                 230                 235                 240
```

-continued

```
Thr Gly Leu Asp Ser Lys Gln Ile Glu Ala Ile Asp Thr Ala Asn Leu
            245                 250                 255

Leu Ala Arg Tyr Leu Pro Lys Leu Glu Arg Tyr Ser Leu Asp Glu Trp
            260                 265                 270

Gln Arg Ile Ala Leu Ser Asn Asn His Glu Tyr Arg Met Gln Gln Leu
            275                 280                 285

Ala Leu Gln Ser Ser Gly Gln Ala Leu Arg Ala Ala Gln Asn Ser Arg
            290                 295                 300

Tyr Pro Thr Val Ser Ala His Val Gly Tyr Gln Asn Asn Leu Tyr Thr
305                 310                 315                 320

Ser Ser Ala Gln Asn Asn Asp Tyr His Tyr Arg Gly Lys Gly Met Ser
            325                 330                 335

Val Gly Val Gln Leu Asn Leu Pro Leu Tyr Thr Gly Gly Glu Leu Ser
            340                 345                 350

Gly Lys Ile His Glu Ala Glu Ala Gln Tyr Gly Ala Ala Glu Ala Gln
            355                 360                 365

Leu Thr Ala Thr Glu Arg His Ile Lys Leu Ala Val Arg Gln Ala Tyr
    370                 375                 380

Thr Glu Ser Gly Ala Ala Arg Tyr Gln Ile Met Ala Gln Glu Arg Val
385                 390                 395                 400

Leu Glu Ser Ser Arg Leu Lys Leu Lys Ser Thr Glu Thr Gly Gln Gln
            405                 410                 415

Tyr Gly Ile Arg Asn Arg Leu Glu Val Ile Arg Ala Arg Gln Glu Val
            420                 425                 430

Ala Gln Ala Glu Gln Lys Leu Ala Gln Ala Arg Tyr Lys Phe Met Leu
            435                 440                 445

Ala Tyr Leu Arg Leu Val Lys Glu Ser Gly Leu Gly Leu Glu Thr Val
    450                 455                 460

Phe Ala Glu
465
```